(12) United States Patent
McMurray et al.

(10) Patent No.: US 8,841,257 B2
(45) Date of Patent: Sep. 23, 2014

(54) INHIBITORS OF STAT3 AND USES THEREOF

(75) Inventors: John S. McMurray, Houston, TX (US); Pijus K. Mandal, Houston, TX (US); Warren S. Liao, Houston, TX (US); Fredika Robertson, Houston, TX (US); Xiaomin Chen, Houston, TX (US); Ramesh Rajaopal, Sugarland, TX (US); Zhiyong Ren, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 182 days.

(21) Appl. No.: 13/263,815

(22) PCT Filed: Apr. 9, 2010

(86) PCT No.: PCT/US2010/030522
§ 371 (c)(1),
(2), (4) Date: Oct. 10, 2011

(87) PCT Pub. No.: WO2010/118309
PCT Pub. Date: Oct. 14, 2010

(65) Prior Publication Data
US 2012/0035114 A1  Feb. 9, 2012

Related U.S. Application Data

(60) Provisional application No. 61/168,454, filed on Apr. 10, 2009.

(51) Int. Cl.
*A61K 38/05* (2006.01)
*A61P 35/00* (2006.01)
*C07K 1/00* (2006.01)
*C07F 9/40* (2006.01)
*C07F 9/553* (2006.01)
*C07F 9/572* (2006.01)
*C07F 9/12* (2006.01)
*A61K 31/66* (2006.01)
*C07F 9/6539* (2006.01)
*C07F 9/6561* (2006.01)
*A61K 31/437* (2006.01)

(52) U.S. Cl.
CPC .............. *C07F 9/5721* (2013.01); *C07F 9/5532* (2013.01); *C07F 9/12* (2013.01); *A61K 31/66* (2013.01); *C07F 9/6539* (2013.01); *C07F 9/5728* (2013.01); *C07F 9/6561* (2013.01); *A61K 31/437* (2013.01)
USPC ......... 514/19.3; 514/21.91; 514/21; 540/487; 548/414; 548/413; 530/402

(58) Field of Classification Search
None
See application file for complete search history.

(56) References Cited

U.S. PATENT DOCUMENTS 6,426,331 B1  7/2002  McKinney et al.
2007/0010428 A1  1/2007  McMurray et al.

FOREIGN PATENT DOCUMENTS

| WO | 00/44774 A2 | 8/2000 |
|----|-------------|--------|
| WO | 00/61602 | 10/2000 |
| WO | 01/83517 A1 | 11/2001 |
| WO | 02/20032 A1 | 3/2002 |
| WO | 02/078617 A2 | 10/2002 |

OTHER PUBLICATIONS

Aggarwal, B.B., et al., Targeting Signal-Transducer-And-Activator-Of-Transcription-3 for Prevention and Therapy of Cancer, Modern Target But Ancient Solution, Annals New York Acad. Sci., 1091 (Signal Transduction Pathways, Part B), 151-169 (2006).
Akira, S., et al., Molecular Cloning of APRF, A Novel IFN-Stimulated Gene Factor 3 P91-Related Transcription Factor Involved in the Gp130-Mediated Signaling Pathway, Cell, 77, 63-71 (1994).
Alonso, M.M., et al., New Cytotoxic Benzo(B)Thiophenilsulfonamide 1,1-Dioxide Derivatives Inhibit A NADH Oxidase Located in Plasma Membranes of Tumour Cells, Brit J. Cancer, 85, 1400-1402 (2001).
Alonso, Ku, et al., New Benzo(B)Thiophenesulphonamide 1,1-Dioxide Derivatives Induce a Reactive Oxygen Species-Mediated Process of Apoptosis in Tumour Cells, Oncogene, 22, 3759-3769 (2003).
Amblard, M., et al., Synthesis and Characterization of Bradykinin B2 Receptor Agonists Containing Constrained Dipeptide Mimics, J. Med. Chem., 42, 4193-4201 (1999).
Andrews, N.C., et al., A Rapid Micropreparation Technique for Extraction of DNA-Binding Proteins From Limiting Numbers of Mammalian Cells, Nuci. Acids. Res., 19:2499 (1991).
Arshady, R., et al., Peptide Synthesis. Part 1. Preparation and Use of Polar Supports Based on Polydimethylacrylamide, J. Chem. Soc. Perkin Trans. I., 529-537 (1981).
Becker, S., et al., Three-Dimensional Structure of the Stat3B Homodimer Bound to DNA, Nature, 394, 145-151 (1998).
Benekti, M., et al., Signal Transducer and Activator of Transcription Proteins in Leukemias, Blood, 101, 2940-2954 (2003).
Bhardwaj, A., et al., Resveratrol Inhibits Proliferation, Induces Apoptosis, and Overcomes Chemoresistance Through Down-Regulation of STAT3 and Nuclear Factor-•B-RegulatedAntiapoptotic and Cell Survival Gene Products in Human Multiple Myeloma Cells, Blood, 109, 2293-2302 (2007).

(Continued)

*Primary Examiner* — James H Alstrum Acevedo
*Assistant Examiner* — Tara Martinez
(74) *Attorney, Agent, or Firm* — Parker Highlander PLLC

(57) ABSTRACT

Compounds which inhibit the activity of signal transducer and activator of transcription 3 (STAT3) are provided together with methods of making and using the same. The compounds are designed to bind to the SH2 domain of STAT3, preventing STAT3 from binding to receptors for interleukin-6 family cytokines, growth factors such as the platelet-derived growth factor, the epidermal growth factor, vascular endothelial growth factor, and other signaling molecules such as leptin. Blocking these interactions prevents STAT3 from being phosphorylated on Tyr705, which is required for the dimerization of STAT3, translocation to the nucleus, binding to STAT3 response elements on promotors, and transcription of genes. In addition to these activities, binding to the SH2 domain of STAT3 breaks up pre-formed dimmers, thereby preventing the transcriptional activity of the inhibitor.

17 Claims, 25 Drawing Sheets

(56) References Cited

OTHER PUBLICATIONS

Bharti, A.C., et al., Curcumin (Diferuloylmethane) Inhibits Constitutive and IL-6-Inducible STAT3 Phosphorylation in Human Multiple Myeloma Cells, J. Immunol., 171, 3863-3871 (2003).
Bhasin, D., et al., Design, Synthesis, and Studies of Small Molecule STAT3 Inhibitors, Bioorg. Med. Chem. Letters, 18, 391-395 (2008).
Blaskovich, M.A., et al. Discovery of JSI-124 (Cucurbitacin I), A Selective Janus Kinase/Signal Transducer and Activator of Transcription 3 Signaling Pathway Inhibitor With Potent Antitumor Activity Against Human and Murine Cancer Cells in Mice, Cancer Res, 63, 1270-1279 (2003).
Bowman, T., et al., STATs in Oncogenesis, Oncogene, 19, 2474-2488 (2000).
Bromberg, J., et al., The Role of STATs in Transcriptional Control and Their Impact on Cellular Function, Oncogene, 19, 2468-2473 (2000).
Bromberg, J., Stat Proteins and Oncogenesis, J. Clin. Invest., 109, 1139-1142 (2002).
Buettner, R., et al., Activated STAT Signaling in Human Tumors Provides Novel Molecular Targets for Therapeutic Intervention, Clin. Cancer Res., 8, 945-954 (2002).
Burke, T.R. Jr., et al., Nonhydrolyzable Phosphotyrosyl Mimetics for the Preparation of Phosphatase-Resistant SH2 Domain Inhibitors, Biochemistry, 33, 6490-4 (1994).
Burke, W.M., et al., Inhibition of Constitutively Active Stat3 Suppresses Growth of Human Ovarian and Breast Cancer Cells, Oncogene, 20, 7925-7934 (2001).
Catlett-Falcone, R., et al., Constitutive Activation of Stat3 Signaling Confers Resistance to Apoptosis in Human U266 Myeloma Cells, Immunity, 10, 105-115 (1999).
Chan, K.S., et al., Disruption of Stat3 Reveals a Critical Role in Both the Initiation and the Promotion Stages of Epithelial Carcinogenesis, J. Clin. Invest., 114, 720-728 (2004).
Chen, J., et al., Design and Synthesis of a New, Conformationally Constrained, Macrocyclic Small-Molecule Inhibitor of STAT3 Via 'Click Chemistry', Bioorg. Med. Chem. Letters, 17, 3939-3942 (2007).
Chiba, J., et al., Synthesis, Biological Evaluation, and Pharmacokinetic Study of Prolyl-1-Piperazinylacetic Acid and Prolyl-4-Piperidinylacetic Acid Derivatives As VLA-4 Antagonists, Bioorg. Med. Chem., 14, 2725-2746 (2006).
Coffer, P., et al., EGF Receptor Deletions Define a Region Specifically Mediating STAT Transcription Factor Activation, Biochem. Biophys. Res. Commun., 210, 74-81 (1995).
Coleman, IV, D.R., et al., Investigation of the Binding Determinants of Phosphopeptides Targeted to the SH2 Domain of Stat3. Development of a High Affinity Peptide Inhibitor., J. Med. Chem., 48, 6661-6670 (2005).
Coleman, IV, D.R., et al., Solid Phase Synthesis of Phosphopeptides Incorporating 2,2-Dimethyloxazolidine Pseudoproline Analogues: Evidence for Trans Leu-Pro Peptide Bonds in Stat3 Inhibitors, Int. J. Pept. Res. Ther., 14, 1-9 (2008).
Darnell, J.E., Jr., Transcription Factors As Targets for Cancer Therapy, Nature Rev. Cancer, 2, 740-749 (2002).
Demange, L., et al., Practical Synthesis of Boc and Fmoc protected 4-Fluoro and 4-Difluoroprolines From Trans-4-Hydroxyproline, Tetrahedron Lett., 39, 1169-1172 (1998).
Deng, J., et al., Small Molecule Inhibitors of Stat3 Signaling Pathway, Current Cancer Drug Targets, 7, 91-107 (2007).
Dhir, R., et al., Stat3 Activation in Prostatic Carcinomas, Prostate, 51, 241-246 (2002).
Dourlat, J., et al., New Syntheses of Tetrazolylmethylphenylalanine and O-Malonyltyrosine As pTyr Mimetics for the Design of STAT3 Dimerization Inhibitors, Bioorg. Med. Chem. Letters, 17, 3943-3946 (2007).
Dowlatia, A., et al., SCH66336, Inhibitor of Protein Farnesylation, Blocks Signal Transducer and Activators of Transcription 3 Signaling in Lung Cancer and Interacts With a Small Molecule Inhibitor of Epidermal Growth Factor Receptor/Human Epidermal Growth Factor Receptor 2, Anti-Cancer Drugs, 19, 9-16 (2008).
Duan, Z., et al., SD-1029 Inhibits Signal Transducer and Activator of Transcription 3 Nuclear Translocation, Clin Cancer Res., 12, 6844-6852 (2006).
Encio, I., et al., Benzo[b]thiophenesulphonamide 1,1-dioxide derivatives Inhibit tNOX Activity in a Redox State-Dependent Manner, British J. Cancer, 92, 690-695 (2005).
Ezquerra, J., et al., Stereoselective Double Alkylation of Ethyl N-Boc-pyroglutamate, J. Org. Chem., 59, 4327-31 (1994).
Faderl, S., et al., WP-1034, A Novel JAK-STAT Inhibitor, With Proapoptotic and Antileukemic Activity in Acute Myeloid Leukemia (AML), Anticancer Res., 25, 1841-50 (2005).
Farquhar, D., et al., Synthesis and Antitumor Evaluation of Bis[(pivaloyloxy)methyl] 2'-Deoxy-5-fluorouridine 5'-Monophosphate (FdUMP): A Strategy to Introduce Nucleotides Into Cells, J. Med Chem., 37, 3902-9 (1994).
Garcia, R. et al., Constitutive Activation of Stat3 in Fibroblasts Transformed by Diverse Oncoproteins and in Breast Carcinoma Cells, Cell and Growth & Differentiation vol. 8 , 1267-1276, (1997).
Garcia, R., et al., Constitutive Activation of Stat3 by the Src and JAK Tyrosine Kinases Participates in Growth Regulation of Human Breast Carcinoma Cells, Oncogene, 20, 2499-2513 (2001).
Gerhartz, C., et al., Differential Activation of Acute Phase Response Factor/STAT3 and STAT1 via the Cytoplasmic Domain of the Interleukin 6 Signal Transducer gp130. I. Definition of a Novel Phosphotyrosine Motif Mediating STAT1 Activation, J. Biol. Chem., 271, 12991-12998 (1996).
Gillespie, P., et al., Conformational Analysis of Dipeptide Mimetics, Biopolymers, 43, 191-217 (1997).
Grandis, J.R., et al., Constitutive Activation of Stat3 Signaling Abrogates Apoptosis in Squamous Cell Carcinogenesis in Vivo, Proc Natl Acad Sci USA., 97, 4227-4232 (2000).
Grandis, J.R. et al., Requirement of Stat3 But Not Stat1 Activation for Epidermal Growth Factor Receptor-Mediated Cell Growth in Vitro, J. Clin. Invest., 102, 1385-1392 (1998).
Gunning, P.T., et al., Isoform Selective Inhibition of STAT1 or STAT3 Homo-Dimerization Via Peptidomimetic Probes: Structural Recognition of STAT SH2 Domains, Bioorg Med Chem Lett., 17, 1875-1878 (2007).
Honda, T., et al., A Novel Dicyanotriterpenoid, 2-cyano-3,12-dioxooleana-1,9(11)-dien-28-onitrile, Active At Picomolar Concentrations for Inhibition of Nitric Oxide Production, Bioorg. Med. Chem. Letters, 12, 1027-1030 (2002).
Huang, M., et al., Constitutive Activation of Stat 3 Oncogene Product in Human Ovarian Carcinoma Cells, Gynecol. Oncol., 79, 67-73 (2000).
Iwamaru, A., et al., A Novel Inhibitor of the STAT3 Pathway Induces Apoptosis in Malignant Glioma Cells Both in Vitro and in Vivo, Oncogene, 26, 2435-2444 (2007).
Jing, N., et al., Targeting Stat3 With G-Quartet Oligodeoxynucleotides in Human Cancer Cells, DNA Cell Biology, 22, 685-696 (2003).
Jing, N., et al., G-Quartet Oligonucleotides: A New Class of Signal Transducer and Activator of Transcription 3 Inhibitors That Suppresses Growth of Prostate and Breast Tumors Through Induction of Apoptosis, Cancer Res., 64, 6603-6609 (2004).
Jing, N., et al., Targeting Signal Transducer and Activator of Transcription 3 With G-Quartet Oligonucleotides: A Potential Novel Therapy for Head and Neck Cancer, Mol. Cancer Ther. 5, 279-286. (2006).
Karras, J.G., et al., STAT3 Regulates the Growth and Immunoglobulin Production of BCL1 B Cell Lymphoma Through Control of Cell Cycle Progression, Cellular Immunology, 202, 124-135 (2000).
Kotha, A., et al., Resveratrol Inhibits Src and Stat3 Signaling and Induces the Apoptosis of Malignant Cells Containing Activated Stat3 Protein, Mol. Cancer Ther., 5, 621-629 (2006).
Lee, Y.K., et al., Flavopiridol Disrupts STAT3/DNA Interactions, Attenuates STAT3-directed Transcription, and Combines With the Jak Kinase Inhibitor AG490 to Achieve Cytotoxic Synergy, Mol. Cancer Ther., 5, 138-148 (2006).
Leong, P.L., et al., Targeted Inhibition of Stat3 With a Decoy Oligonucleotide Abrogates Head and Neck Cancer Cell Growth, Proc. Natl Acad. Sci. USA, 100, 4138-4143 (2003).
Levy, D.E., et al., Stats: Transcriptional Control and Biological Impact, Nature Rev. Mol. Cell. Blot., 3, 651-662 (2002).
Liby, K., et al., The Synthetic Triterpenoid CDDO-Imidazolide Suppresses STAT Phosphorylation and Induces Apoptosis in Myeloma and Lung Cancer Cells, Clin Cancer Res., 12, 4288-4293 (2006).

(56) References Cited

OTHER PUBLICATIONS

Liu, X., et al., STAT3-decoy ODN Inhibits Cytokine Autocrine Expression by Murine Tumor Cells, Cell. Mol. Immunol., 4, 309-313 (2007).
Maloney, K.N., et al., Phaeosphaeride A, an Inhibitor of STAT3-Dependent Signaling Isolated From an Endophytic Fungus, Org. Lett., 8, 4067-4070 (2006).
Mandal, P.K., et al., Solid Phase Synthesis of Stat3 Inhibitors Incorporating O-Carbamoylserine and O-Carbamoylthreonine as Glutamine Mimics, Bioorg. Med. Chem. Lett., 17, 654-656 (2007a).
Mandal, P.K., et al., Pd-C Induced Catalytic Transfer Hydrogenation With Triethylsilane, J. Org. Chem, 72, 6599-660 (2007b).
McMurray, J.S., Structural Basis for the Binding of High Affinity Phosphopeptides to Stat3, Biopolymers, 90, 69-79 (2008).
Nasir, M.S., et al., Fluorescence Polarization: An Analytical Tool for Immunoassay and Drug Discovery, Comb. Chem. High T. Scr, 2, 177-190 (1999).
Niu, G., et al., Constitutive Stat3 Activity Up-Regulates VEGF Expression and Tumor Angiogenesis, Oncogene, 21, 2000-2008 (2002a).
Niu, G., et al., Gene Therapy With Dominant-Negative Stat3 Suppresses Growth of the Murine Melanoma B16 Tumor in Vivo, Cancer Res., 59, 5059-5063 (1999).
Niu, G., et al., Roles of Activated Src and Stat3 Signaling in Melanoma Tumor Cell Growth, Oncogene, 21, 7001-7010 (2002b).
Owicki, J.C., Fluorescence Polarization and Anisotropy in High Throughput Screening: Perspectives and Primer, J. Biomol. Screen., 5, 297-306 (2000).
Qabar, M.N., et al., A Facile Solution and Solid Phase Synthesis of Phosphotyrosine Mimetic L-4-[diethylphosphono(difluoromethyl)]phenylalanine (F2Pmp(EtO)2) DERivatives,. Tetrahedron, 53, 11171-11178 (1997).
Real, P.J., et al., Resistance to Chemotherapy Via Stat3-Dependent Overexpression of Bcl-2 in Metastatic Breast Cancer Cells, Oncogene, 21, 7611-761 8 (2002).
Ren, Z., et al., Identification of a High Affinity Phosphopeptide Inhibitor of Stat3, Bioorg. Med. Chem. Lett., 13, 633-636 (2003).
Ren, Z., et al., ErbB-2 Activates Stat3•in a Src- and JAK2-Dependent Manner, J. Biol. Chem., 277, 38486-38493 (2002).
Rojas, M., et al., Genetic Engineering of Proteins With Cell Membrane Permeability, Nature Biotechnol., 16, 370-375 (1998).
Schaefer, L.K., et al., Constitutive Activation of Stat3.altpha. In Brain Tumors: Localization to Tumor Endothelial Cells and Activation by the Endothelial Tyrosine Kinase Receptor (VEGFR-2), Oncogene, 21, 2058-2065 (2002).
Scholz, A., et al., Activated Signal Transducer and Activator of Transcription 3 (STAT3) Supports the Malignant Phenotype of Human Pancreatic Cancer, Gastroenterology, 125, 891-905 (2003).
Schreiner, S.J., et al., Activation of STAT3 by the Src Family Kinase Hck Requires a Functional Sh3 Domain, J. Biol. Chem., 277, 45680-45687 (2002).
Schust, J., et al., Stattic: A Small-Molecule Inhibitor of STAT3 Activation and Dimerization, Chem. Biol., 13, 1235-1242 (2006).
Schust, J., et al., A High-Throughput Fluorescence Polarization Assay for Signal Transducer and Activator of Transcription 3, Anal. Biochem., 330, 114-118 (2004).
Seki Y.; et al., STAT3 and MAPK in Human Lung Cancer Tissues and Suppression of Oncogenic Growth by JAB and Dominant Negative STAT3, Int. J. Oncology, 24, 931-934 (2004).
Shahripour, A., et al., Novel Phosphotyrosine Mimetics in the Design of Peptide Ligands for pp60src SH2 Domain, Bioorg. Med. Chem. Left, 6, 1209-1214 (1996).
Shao, H.; et al., Identification and Characterization of Signal Transducer and Activator of Transcription 3 Recruitment Sites Within the Epidermal Growth Factor Receptor, Cancer Res., 63, 3923-3930 (2003).
Siddiquee K.A., et al., An Oxazole-Based Small-Molecule Stat3 Inhibitor Modulates Stat3 Stability and Processing and Induces Antitumor Cell Effects, Chem Biol., 2, 787-798 (2007).

Song, J.I., et al., STAT Signaling in Head and Neck Cancer, Oncogene, 19, 2489-2495 (2000).
Song, H., A Low-Molecular-Weight Compound Discovered Through Virtual Database Screening Inhibits Stat3 Function in Breast Cancer Cells, Proc Natl Acad Sci U S A., 102, 4700-4705 (2005).
Stahl, N., et al., Choice of STATs and Other Substrates Specified by Modular Tyrosine-Based Motifs in Cytokine Receptors, Science, 267, 1349-1353 (1995).
Stankovic, C.L., et al., The Role of 4-Phosphonodifluoromethyl- and 4-Phosphono-Phenylalanine in the Selectivity and Cellular Uptake of SH2 Domain Ligands, Bioorganic & Medicinal Chemistry Letters, 7, 1909-1914 (1997).
Stark, G.R., et al., How Cells Respond to Interferons, Ann. Rev. Biochem., 67, 227-264 (1998).
Sun, J., et al., Cucurbitacin Q: A Selective STAT3 Activation Inhibitor With Potent Antitumor Activity, Oncogene, 24, 3236-3245 (2005).
Taylor, C.M., et al., The Impact of Pyrrolidine Hydroxylation on the Conformation of Proline-Containing Peptides, J. Org. Chem., 70, 1306-1315 (2005).
Turkson J., et al., Phosphotyrosyl Peptides Block Stat3-Mediated DNA-Binding Activity, Gene Regulation and Cell Transformation, J. Biol. Chem., 276, 45443-45455 (2001).
Turkson, J., et al., Novel Peptidomimetic Inhibitors of Signal Transducer and Activator of Transcription 3 Dimerization and Biological Activity, Mol. Cancer Ther., 3, 261-269 (2004).
Verstovsek, S., et al., WP1066 , A Novel JAK2 Inhibitor, Suppresses Proliferation and Induces Apoptosis in Erythroid Human Cells Carrying the JAK2 V617F Mutation, Clin. Cancer Res., 14, 788-796 (2008).
Vu, C.B., et al., Nonpeptidic SH2 Inhibitors of the Tyrosine Kinase ZAP-70, Bioorg. Med. Chem. Lett, 9, 3009-3014 (1999).
Weber-Nordt, R.M., et al., Constitutive Activation of Stat Proteins in Primary Lymphoid and Myeloid Leukemia Cells and in Epstein-Barr Virus (EBV)-Related Lymphoma Cell Lines, Blood, 88, 809-816 (1996a).
Wrobel, J., et al., Preparation of L-(phosphodifluoromethyl) Phenylalanine Derivatives As Non-Hydrolyzable Mimetics of O-phosphotyrosine, Tetrahedron Lett., 34, 3543-3546 (1993).
Xi, S., et al., In Vivo Antitumor Efficacy of STAT3 Blockade Using a Transcription Factor Decoy Approach: Implications for Cancer Therapy, Oncogene, 24, 970-979 (2005).
Yu, H., et al., The Status of Cancer—New Molecular Targets Come of Age, Nature Rev. Cancer. 4, 97-105 (2004).
Zhang, T., et al., Grb2 Regulates Stat3 Activation Negatively in Epidermal Growth Factor Signaling, Biochemical J., 376, 457-464 (2003).
Zhang, X., et al., STAT3-decoy Oligodeoxynucleotide Inhibits the Growth of Human Lung Cancer Via Down-Regulating Its Target Genes, Oncol. Rep., 17, 1377-1382 (2007a).
Zhang X., et al., Therapeutic Effects of STAT3 Decoy Oligodeoxynucleotide on Human Lung Cancer in Xenograft Mice, BMC Cancer, 7, 149 (2007b).
Zhong; Z., et al., Stat3: A STAT Family Member Activated by Tyrosine Phosphorylation in Response to Epidermat Growth Factor and Interleukin-6, Science, 264, 95-98 (1994a).
Zhong; Z., et al., Stat3 and Stat4: Members of the Family of Signal Transducers and Activators of Transcription, Proc. Nat. Acad. Sci., U.S.A., 91, 4806-4810 (1994b).
Mandal, et al., "Potent and Selective Phosphopeptide Mimetic Prodrugs Targeted to the Src Homology 2 (SH2) Domain of Signal Transducer and Activator of Transcription 3," J. Med. Chem., 54:3549-5463, 2011.
Mandal, et al., "Structure-Activity Studies of Phosphopeptidomimetic Prodrugs Targeting the Src Homology 2 (SH2) Domain of Signal Transducer and Activator of Transcription 3 (Stat3)," Int. J. Pept. Res. Ther., 19:3-12, 2013.
Mandal, et al., "Synthesis of phosphatase-stable, cell-permeable peptidomimetic prodrugs that target the SH2 domain of Stat3," Org. Lett., 11:3394-3397, 2009.

pβMCinn-Leu-Pro-Gln-NHBn
IC$_{50}$ = 70 ± 15 nM pβMCinn-Nle-mPro-Gln-NHBn
IC$_{50}$ = 35 ± 4 nM pβMCinn-Leu-mPro-Gln-NHBn
IC$_{50}$ = 46 ± 5 nM pβMCinn-Haic-Gln-NHBn
IC$_{50}$ = 61 ± 8 nM pβMCinn = 3-(4-phosphoryloxyphenyl)-but-2-enoate

| EGF       | − | + | +   | − | +   | +   |
| EXAMPLE 1 | − | − | −   | + | +   | +   |
|           |   |   | 20' | 45' |   | 20' | 45' | pStat3

Total Stat3

| IFNγ      | − | + | +   | − | +   | +   |
| EXAMPLE 1 | − | − | −   | + | +   | +   |
|           |   |   | 20' | 45' |   | 20' | 45' | pStat1

Total Stat1

| EGF       | − | + | +   | − | +   | +   |
| EXAMPLE 1 | − | − | −   | + | +   | +   |
|           |   |   | 20' | 45' |   | 20' | 45' | pAkt

Total Akt

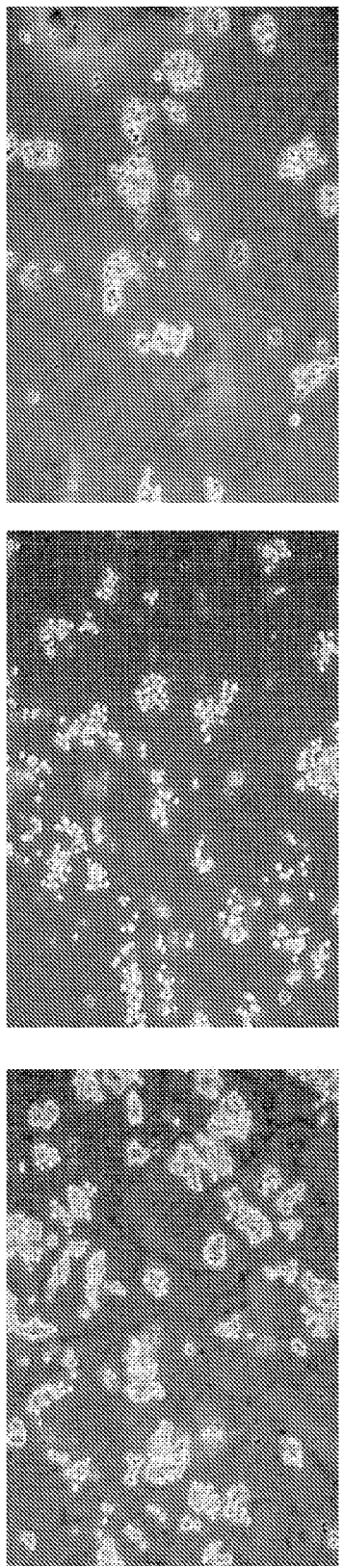
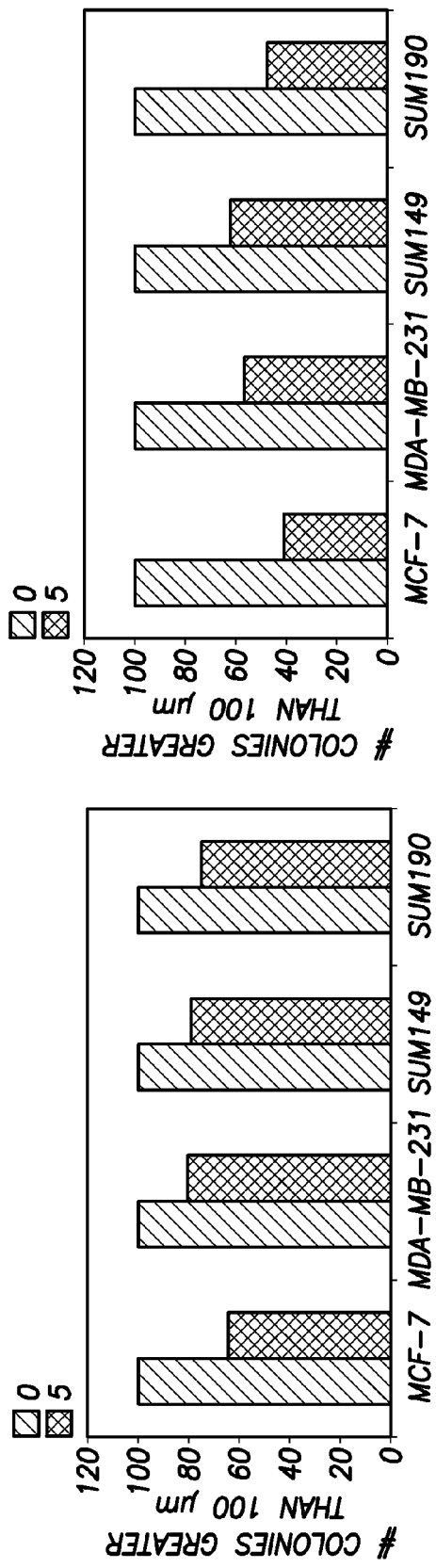
FIG. 12A
FIG. 12B
FIG. 12C

EXAMPLE 18

EXAMPLE 23

EXAMPLE 25

EXAMPLE 24

0    .01   .05   .1    .5   1.0   5.0  (μM)

EXAMPLE 16

FAK Y861

FAK

EXAMPLE 18

FAK Y861

FAK

EXAMPLE 1

FAK Y861

FAK

INHIBITORS OF STAT3 AND USES THEREOF

CROSS-REFERENCE TO RELATED APPLICATIONS

This application claims priority to U.S. Pat. App. Ser. No. 61/168,454 filed Apr. 10, 2010. The application is incorporated by reference herein in its entirety.

STATEMENT REGARDING FEDERALLY SPONSORED RESEARCH OR DEVELOPMENT

This invention was made with government support under CA096652 and CA070907 awarded by The National Institutes of Health. The government has certain rights in the invention.

FIELD OF THE INVENTION

The present invention is directed to compounds that inhibit or modulation STAT3, their synthesis, and their application as a pharmaceutical for the treatment of disease.

THE NAMES OF THE PARTIES TO A JOINT RESEARCH AGREEMENT

None.

REFERENCE TO SEQUENCE LISTING

None.

BACKGROUND OF THE INVENTION

Signal transducer and activator of transcription 3 ("STAT3") is a member of the STAT family of transcription factors that relate signals from extracellular signaling protein receptors on the plasma membrane directly to the nucleus. See e.g., Bromberg, J., et al., *The Role of STATs in Transcriptional Control and their Impact on Cellular Function*, Oncogene, 19, 2468-2473 (2000).

STAT3 has been shown to be constitutively activated in cancer including, but not limited to, cancers of the brain, head, neck, breast, prostate, lung, ovary, pancreas, leukemia, multiple myeloma, and lymphoma. See e.g., Song, J. I., et al., *STAT Signaling in Head and Neck Cancer*, Oncogene, 19, 2489-2495 (2000); Garcia, R., et al., *Constitutive Activation of STAT3 in Fibroblasts Transformed By Diverse Oncoproteins and in Breast Carcinoma Cells*, Cell Growth Duff., 812, 1267-76 (1997); Schaefer, L. K., et al., *Constitutive Activation of STAT3 in Brain Tumors: Localization to Tumor Endothelial Cells and Activation by the Endothelial Tyrosine Kinase Receptor (VEGFR-2)*, Oncogene, 21, 2058-2065 (2002); Dhir, R., et al., *STAT3 Activation in Prostatic Carcinomas*, Prostate, 51, 241-246 (2002); Seki Y.; et al., *STAT3 and MAPK in Human Lung Cancer Tissues and Suppression Of Oncogenic Growth by JAB and Dominant Negative STAT3*, Int. J. Oncology, 24, 931-934 (2004); Huang, M., et al., *Constitutive Activation of STAT3 Oncogene Product in Human Ovarian Carcinoma Cells*, Gynecol. Oncol., 79, 67-73 (2000); Scholz, A., et al., *Activated Signal Transducer and Activator of Transcription 3 (STAT3) Supports the Malignant Phenotype of Human Pancreatic Cancer*, Gastroenterology, 125, 891-905 (2003); Benekti, M., et al., *Signal Transducer and Activator of Transcription Proteins in Leukemias*, Blood, 101, 2940-2954 (2003); Weber-Nordt, R. M., et al., *Constitutive Activation of STAT Proteins in Primary Lymphoid and Myeloid Leukemia Cells and in Epstein-Barr Virus (EBV)-Related Lymphoma Cell Lines*, Blood, 88, 809-816 (1996a); Bowman, T., et al., *STATs In Oncogenesis*, Oncogene, 19, 2474-2488 (2000); Yu, H.; Jove, R. *The STATs of cancer—new molecular targets come of age*. Nat Rev Cancer 4, 97-105, (2004).

Certain small molecules have been designed to inhibit STAT3, but are poor inhibitors of STAT3 because the molecule is either not selective and/or have low affinity for binding, or low potency as a potential drug product. For example, small molecules have been designed around a portion of the STAT3 molecule but have reported a low binding affinity. Dourlate et al 2007. Similarly, several small molecules have been reported to inhibit Stat3 phosphorylation in cells but they are not selective for Stat3 and impact other pathways and processes in cells. For example, cryptotanshinone, a known COX-2 inhibitor, was recently reported to inhibit STAT3 activity in tumor cells. D. S.; Kim, et al., *Cryptotanshinone Inhibits Constitutive Signal Transducer And Activator Of Transcription 3 Function Through Blocking The Dimerization In DU145 Prostate Cancer Cells*, Cancer Res, 69, 193-202 (2009). According to the reported model, it binds to the phosphotyrosine site on STAT3. While cryptotanshinone inhibits NF-kB inhibition and activation of the PI3K/Akt pathway, it is it is unlikely that cryptotanshinone binds to the SH2 domain of STAT3 in cultured cells.

Another example of a compound that reportedly inhibits constitutive phosphorylation of STAT3 and is potentially useful to treat hematopoietic malignancies is CDDO-Me. Ahmad, R., et al., *Triterpenoid CDDO-Methyl Ester Inhibits the Janus-Activated Kinase-1 (JAK1)→Signal Transducer and Activator of Transcription-3 (STAT3) Pathway By Direct Inhibition Of JAK1 And STAT3*, Cancer Res, 68, 2920-6 (2008); Ling, X., et al., *The Novel Triterpenoid C-28 Methyl Ester of 2-Cyano-3,12-Dioxoolen-1,9-Dien-28-Oic Acid Inhibits Metastatic Murine Breast Tumor Growth Through Inactivation Of STAT3 Signaling*, Cancer Res, 67, 4210-8 (2007). However, this compound also inhibits NF-κB, and targets mitochondrial glutathione Ahmad, R., et al., D. *Triterpenoid Cddo-Me Blocks the NF-Kappab Pathway by Direct Inhibition of Ikkbeta on Cys-179*, J Biol Chem, 281, 35764-9 (2006); Samudio, I. et al, *2-Cyano-3,12-dioxooleana-1,9-dien-28-imidazolide (CDDO-Im) Directly Targets Mitochondrial Glutathione To Induce Apoptosis In Pancreatic Cancer*, J Biol Chem, 280, 36273-82 (2005). It also induces apoptosis by interfering with the redox potential of the cell. Ikeda, T., et al, *The Novel Triterpenoid CDDO and its Derivatives Induce Apoptosis by Disruption of Intracellular Redox Balance* Cancer Res, 63, 5551-8 (2008). In short, the compound is not a selective inhibitor of STAT3 activation or phosphorylation.

A need exists therefore for selective, potent STAT3 inhibitors useful in treating cancer and other STAT3-mediated diseases.

BRIEF SUMMARY OF THE INVENTION

Novel compounds and pharmaceutical compositions that inhibit STAT3 have been found together methods of synthesizing and methods of using the compounds including methods for of inhibiting STAT3 disorders in a patient by administering a therapeutically effective amount of one or more of the compounds.

The present invention discloses a class of compounds useful in treating STAT3-mediated disorders and conditions, defined by the structural Formula I:

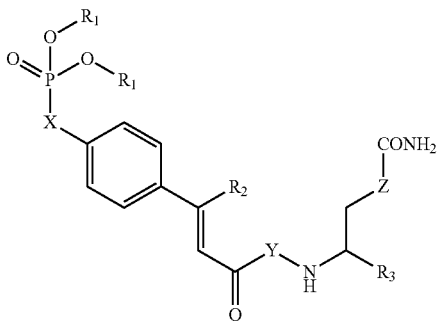

wherein X is O, CH$_2$, CF$_2$;
  Y is a dipeptide mimic such as Haic (5-(amino)-1,2,4,5,6,7-hexahydro-4-oxo-(2S,5S)-azepino[3,2,1-hi]indole-2-carboxylic acid), or a dipeptide of the structure Aaa-Bbb in which Aaa is norleucine, leucine, or homophenylalanine and Bbb is proline, (2S,3R,4S)-cis-3,4-methanoproline, 4,4-difluoroproline, 4,4-dimethylproline, 4-hydroxyproline;
  Z is CH$_2$, NH, or O;
  R$_1$ is H; a phenyl substituted group with one or more of the following; H, CH$_3$, F, Cl, Br, OCOCH$_3$, NO$_2$, or CN; pivaloyloxymethyl; benzoyloxymethyl; benzoyloxymethyl in which the phenyl group is substituted with one or more of the following, H, CH$_3$, F, Cl, Br, OCOCH$_3$, or NO$_2$; acetoxybenzyl; 2-pyridyl; 3-pyridyl; 4-pyridyl; or acyloxymethyl in which the acyl group possesses aliphatic or polyethylene glycol groups, CH$_2$OCO(CH$_2$CH$_2$O)$_n$CH$_2$CH$_3$ in which in which n≥1, CH$_2$OCO(CH$_2$CH$_2$O)$_n$CH$_3$ in which in which n≥1;
  R$_2$ is H or CH$_3$, and
  R$_3$ is H, CH$_3$, CH(CH$_3$)$_2$, CH$_2$CH(CH$_3$)$_2$, CH$_2$CH$_2$CH$_2$CH$_3$, CH$_2$C$_6$C$_4$OH(para), CH$_2$OCH$_2$C$_6$H$_5$, CH(CH$_3$)OCH$_2$C$_6$H$_5$, CH$_2$OH, CH$_2$OCOCH$_3$, CH(CH$_3$)OH, CH$_2$OCO(CH$_2$CH$_2$O)$_n$CH$_3$ n=1-50, 1-piperidinomethyl, 4-morpholinomethyl, 1-methyl-4-piperazinomethyl, CH$_2$NH$_3$, CH$_2$NHCOCH$_3$, CONHCH$_2$C$_6$H$_5$.
  when R$_1$ is pivaloyloxymethyl, R$_2$ is not H and/or R$_3$ is not CONHCH$_2$C$_6$H$_5$ Compounds according to the present invention possess useful STAT3 inhibiting or modulating activity and may be used in the treatment or prophylaxis of a disease or condition in which STAT3 plays an active role. Thus, in the broad aspect, the present invention provides for pharmaceutical compositions comprising one or more compounds of the present invention together with a pharmaceutically acceptable carrier as well as methods of making and using the compounds and compositions. The present invention provides methods for treating a STAT3-mediated disorder in a patient in need of such treatment comprising administering to said patient a therapeutically effective amount of a compound or composition according to the subject invention. The present invention also contemplates the use of compounds disclosed herein for use in the manufacture of a medicament for the treatment of a diseases or condition ameliorated by the inhibition of STAT3.

BRIEF DESCRIPTION OF THE SEVERAL VIEWS OF THE DRAWINGS

In FIG. 8G, the compound of Example 16 has negligible effect on normal cells compared to the vehicle, DMSO.

FIG. 12 provides data showing inhibition of anchorage dependent growth of breast tumor cells. FIG. 12A is micrographs of SUM149 inflammatory breast tumor cells by the compounds of Examples 1 and 8. FIG. 12B is a graph of the inhibition of a panel of breast tumor lines by compound of Example 8. FIG. 12C is a graph of the inhibition of a panel of breast tumor cell lines by the compound of Example 1.

DETAILED DESCRIPTION OF THE INVENTION

Figure 1:
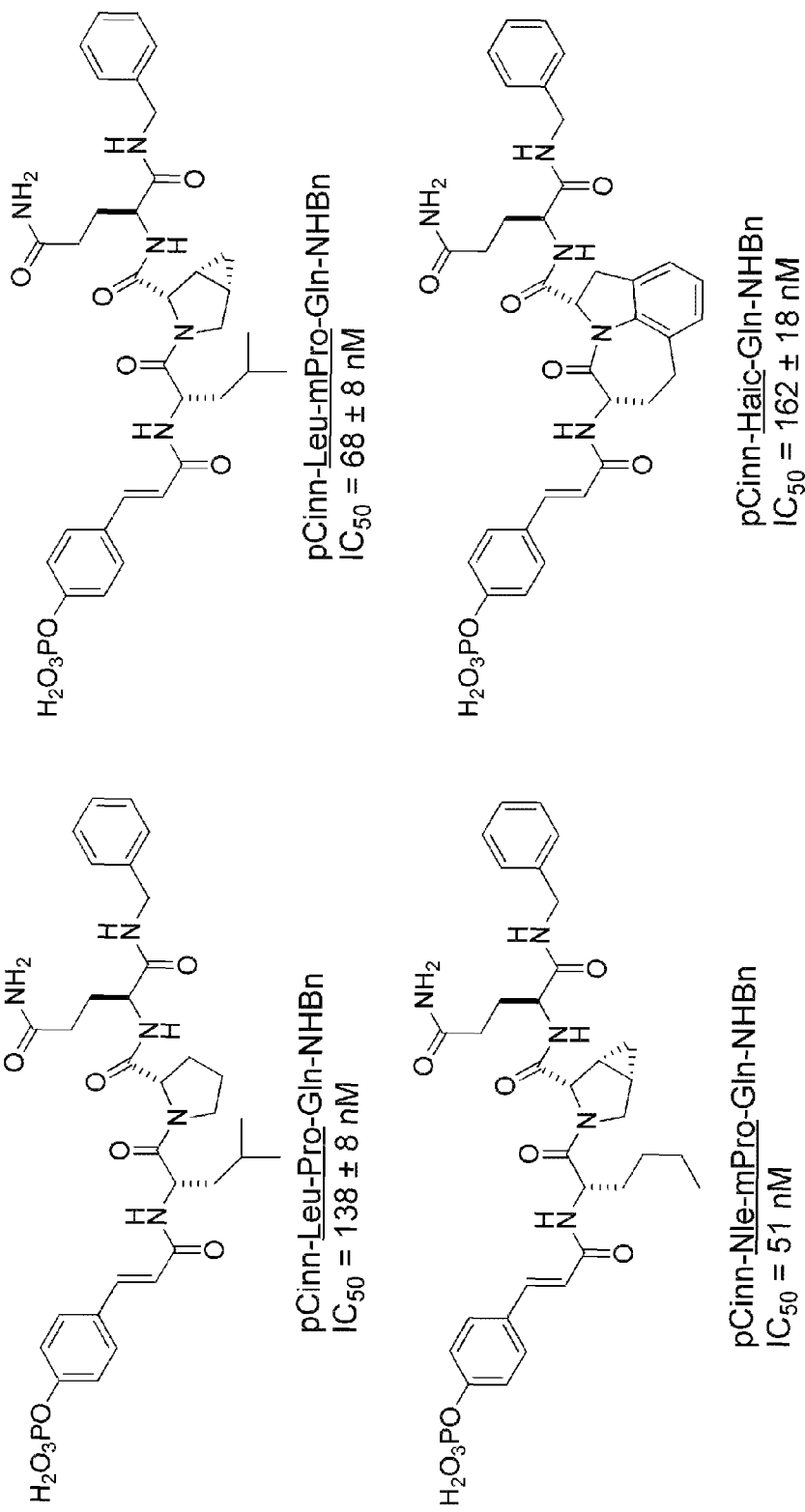
FIG. 1 shows the general basis for the four scaffolds of STAT3 inhibitors presented herein: Leu-Pro, Leu-mPro, Nle-mPro, and Haic.

Certain compounds of the present invention may have the structural Formula I above. Also, certain compounds may have the structural Formula II as follows:

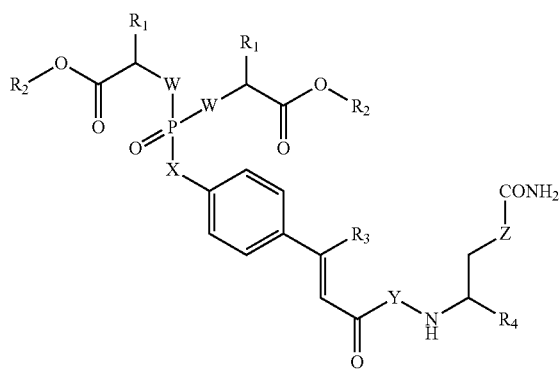

wherein X is O, $CH_2$, or $CF_2$;
Y is a dipeptide mimic such as Haic (5-(amino)-1,2,4,5,6,7-hexahydro-4-oxo-(2S,5S)-azepino[3,2,1-hi]indole-2-carboxylic acid), or a dipeptide of the structure Aaa-Bbb in which Aaa is norleucine, leucine, or homophenylalanine and Bbb is proline, (2S,3R,4S)-cis-3,4-methanoproline, 4,4-difluoroproline, 4,4-dimethylproline, 4-hydroxyproline;
Z is $CH_2$, NH, or O;
W is O, NH, or $NH_2$
$R_1$ is H; $CH_3$, $CH_2C_6H_5$, $CH_2$-2-pyridyl, $CH_2$-3-pyridyl, $CH_2$-4-pyridyl
$R_2$ is $CH_3$, $CH_2CH_3$, $CH(CH_3)_2$, $C_6H_5$, $(CH_2CH_2O)_nCH_3$ in which n≥1, $CH_2OCO(CH_2CH_2O)_nCH_2CH_3$ in which in which n≥1.
$R_3$ is H or $CH_3$; and
$R_4$ is H, $CH_3$, $CH(CH_3)_2$, $CH_2CH(CH_3)_2$, $CH_2CH_2CH_2CH_3$, $CH_2C_6C_4OH$(para), $CH_2OCH_2C_6H_5$, $CH(CH_3)OCH_2C_6H_5$, $CH_2OH$, $CH_2OCOCH_3$, $CH(CH_3)OH$, $CH_2OCO(CH_2CH_2O)_nCH_3$ n=1-50, $CH_2OCO(CH_2CH_2O)nCH_2CH_3$ n=1-50, 1-piperidinomethyl, 4-morpholinomethyl, 1-methyl-4-piperazinomethyl, $CH_2NH_3$, $CH_2NHCOCH_3$, $CONHCH_2C_6H_5$.

Further, certain compounds of the present invention may have the structural Formula III:

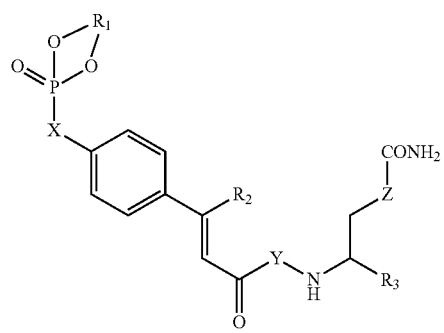

wherein X is O, $CH_2$, $CF_2$;
Y is a dipeptide mimic such as Haic (5-(amino)-1,2,4,5,6,7-hexahydro-4-oxo-(2S,5S)-azepino[3,2,1-hi]indole-2-carboxylic acid), or a dipeptide of the structure Aaa-Bbb in which Aaa is norleucine, leucine, or homophenylalanine and Bbb is proline, (2S,3R,4S)-cis-3,4-methanoproline, 4,4-difluoroproline, 4,4-dimethylproline, 4-hydroxyproline;
Z is $CH_2$, NH, or O;
$R_1$ is bis methyleneoxy-1,2-phthaloyl, in which the phthaloyl can be substituted with one or more halogens, nitro groups, OH, $OCH_3$, $OCOR_4$ in which $R_4$ can be an aliphatic, aromatic, or heterocyclic group, $O(CH_2CH_2O)$nOCH_3 n=1-50, $O(CH_2CH_2O)nOCH_2CH_3$ n=1-50
$R_2$ is H or $CH_3$; and
$R_3$ is H, $CH_3$, $CH(CH_3)_2$, $CH_2CH(CH_3)_2$, $CH_2CH_2CH_2CH_3$, $CH_2C_6C_4OH$(para), $CH_2OCH_2C_6H_5$, $CH(CH_3)OCH_2C_6H_5$, $CH_2OH$, $CH_2OCOCH_3$, $CH(CH_3)OH$, $CH_2OCO(CH_2CH_2O)_nCH_3$ n=1-50, 1-piperidinomethyl, 4-morpholinomethyl, 1-methyl-4-piperazinomethyl, $CH_2NH_3$, $CH_2NHCOCH_3$, $CONHCH_2C_6H_5$.

Specific compounds of particular interest consist of compounds and pharmaceutically-acceptable salts, esters and prodrugs thereof as follows:
(2E)-3-[4-[[bis[(2,2-dimethyl-1-oxopropoxy)methoxy] phosphinyl]difluoromethyl]phenyl]-but-2-enoyl-Haic-(R)-4-aminopentamide (2E)-3-[4-[[bis[(2,2-dimethyl-1-oxopropoxy)methoxy]
   phosphinyl]difluoromethyl]phenyl]-but-2-enoyl-Haic-
   glutaminyl-benzylamide
(2E)-3-[4-[[bis[(2,2-dimethyl-1-oxopropoxy)methoxy]
   phosphinyl]difluoromethyl]phenyl]-but-2-enoyl-Haic-2-
   aminoethylcarbamate
(2E)-3-[4-[[bis[(2,2-dimethyl-1-oxopropoxy)methoxy]
   phosphinyl]difluoromethyl]phenyl]-but-2-enoyl-Haic-2-
   aminoethylurea
(2E)-3-[4-[[bis[(2,2-dimethyl-1-oxopropoxy)methoxy]
   phosphinyl]difluoromethyl]phenyl]-propenoyl-Haic-(R)-
   4-aminopentamide
(2E)-3-[4-[[bis[(2,2-dimethyl-1-oxopropoxy)methoxy]
   phosphinyl]oxy]phenyl]-but-2-enoyl-Haic-(R)-4-amino-
   pentamide
(2E)-3-[4-[(Diethoxyphosphinyl)difluoromethyl]phenyl]-
   but-2-enoyl-Haic-(R)-4-aminopentamide
(E)-3-[4-[(Diphenoxyphosphinyl)difluoromethyl]phenyl]-
   but-2-enoyl-Haic-(R)-4-aminopentamide
(2E)-3-[4-[[Bis[(4-fluorobenzoyloxy)methoxy]phosphinyl]
   difluoromethyl]phenyl]-but-2-enoyl-Haic-(R)-4-amino-
   pentamide
(2E)-3-[4-[[Bis[(benzoyloxy)methoxy]phosphinyl]difluo-
   romethyl]phenyl]-but-2-enoyl-Haic-(R)-4-aminopentam-
   ide
(2E)-3-[4-[[phthaloylbis(oxymethoxy)]phosphinyl]difluo-
   romethyl]phenyl]-but-2-enoyl-Haic-(R)-4-aminopentam-
   ide
(2E)-3-[4-[[Bis[(piperonyloxy)methoxy]phosphinyl]difluo-
   romethyl]phenyl]-but-2-enoyl-Haic-(R)-4-aminopentam-
   ide
(E)-3-[4-[[Bis[(2-methylbenzoyloxy)methoxy]phosphinyl]
   difluoromethyl]phenyl]-but-2-enoyl-Haic-(R)-4-amino-
   pentamide
(2E)-3-[4-[[Bis[(2-chlorobenzoyloxy)methoxy]phosphinyl]
   difluoromethyl]phenyl]-but-2-enoyl-Haic-(R)-4-amino-
   pentamide
(E)-3-(4-(dipivaloyloxymethylphosphinyldifluoromethyl)
   phenyl)-but-2-enoyl-norleucinyl-(2S,3R,4S)-methano-
   prolinyl-glutaminyl-benzylamide
(2E)-3-[4-[[bis[(2,2-dimethyl-1-oxopropoxy)methoxy]
   phosphinyl]difluoromethyl]phenyl]-but-2-enoyl-nor-
   leucinyl-(2S,3R,4S)-methanoprolinyl-(4S,5R)-4-amino-
   5-benzyloxyhexamide
(2E)-3-[4-[[bis[(2,2-dimethyl-1-oxopropoxy)methoxy]
   phosphinyl]difluoromethyl]phenyl]-but-2-enoyl-nor-
   leucinyl-(2R,3S,4R)-methanoprolinyl-(4S,5R)-4-amino-
   5-benzyloxyhexamide
(2E)-3-[4-[[bis[(2,2-dimethyl-1-oxopropoxy)methoxy]
   phosphinyl]difluoromethyl]phenyl]-but-2-enoyl-nor-
   leucinyl-(2S,3R,4S)-methanoprolinyl-(R)-4-aminopenta-
   mide
(2E)-3-[4-[[bis[(2,2-dimethyl-1-oxopropoxy)methoxy]
   phosphinyl]difluoromethyl]phenyl]-but-2-enoyl-nor-
   leucinyl-(2R,3S,4R)-methanoprolinyl-(R)-4-aminopenta-
   mide
(2E)-3-[4-[[bis[(2,2-dimethyl-1-oxopropoxy)methoxy]
   phosphinyl]difluoromethyl]phenyl]-but-2-enoyl-nor-
   leucinyl-(Rac)-methanoprolinyl-2-aminoethylurea
(2E)-3-[4-[[bis[(2,2-dimethyl-1-oxopropoxy)methoxy]
   phosphinyl]difluoromethyl]phenyl]-but-2-enoyl-nor-
   leucinyl-(2S,3R,4S)-methanoprolinyl-2-aminoethylcar-
   bamate
(2E)-3-[4-[(Diphenoxyphosphinyl)difluoromethyl]phenyl]-
   but-2-enoyl-norleucinyl-(2S,3R,4S)-methanoprolinyl-
   (2S,3R,4S)-methanoprolinyl-(4S, 5R)-4-amino-5-benzy-
   loxyhexamide
(2E)-3-[4-[[bis[(2,2-dimethyl-1-oxopropoxy)methoxy]
   phosphinyl]difluoromethyl]phenyl]-but-2-enoyl-nor-
   leucinyl-prolinyl-(R)-4-aminopentamide
(2E)-3-[4-[[bis[(2,2-dimethyl-1-oxopropoxy)methoxy]
   phosphinyl]difluoromethyl]phenyl]-but-2-enoyl-nor-
   leucinyl-4,4-difluoroprolinyl-(R)-4-aminopentamide
(2E)-3-[4-[[bis[(2,2-dimethyl-1-oxopropoxy)methoxy]
   phosphinyl]difluoromethyl]phenyl]-but-2-enoyl-nor-
   leucinyl-4,4-dimethylprolinyl-(R)-4-aminopentamid As used herein, the terms below have the meanings indicated:

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon.

An "acetyl" group refers to a —C(O)CH$_3$ group.

An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20, preferably 2 to 6, carbon atoms.

Alkenylene refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like.

The term "alkylene," as used herein, alone or in combination, refers to a saturated aliphatic group derived from a straight or branched chain saturated hydrocarbon attached at two or more positions, such as methylene (—CH$_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). Examples of alkynyl radicals include ethynyl, propynyl, hydroxypropynyl, Butyn-1-yl, butyn-2-yl, pentyn-1-yl, 3-methylbutyn-1-yl, hexyn-2-yl, and the like.

The terms "amido" and "carbamoyl,"as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl,"as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR' group, with R and R' as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cycloalkyl," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multi-centered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groupsinclude carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR' group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

The term "pCinn" means 4-phosphoryloxycinnamate.

The term "pβMcinn" means 3-(4-phosphoryloxyphenyl)-but-2-enoate.

As used herein, the term "Haic" is a dipeptide mimic and is an abbreviation of ((2S,5S)-5-amino-1,2,4,5,6,7-hexahydro-4-oxo-azepino[3,2,1-hi]indole-2-carboxylic acid).

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-menbered carbocyclic or heterocyclic ring consisting of zero to three heteroatoms, for example forming methylenedioxy or ethylenedioxy. An optionally substituted group may be unsubstituted (e.g., $—CH_2CH_3$), fully substituted (e.g., $—CF_2CF_3$), monosubstituted (e.g., $—CH_2CH_2F$) or substituted at a level anywhere in-between fully substituted and monosubstituted (e.g., $—CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particuar moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as $—C(O)N(R)—$ may be attached to the parent moiety at either the carbon or the nitrogen.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "bond" refers to a covalent linkage between two atoms, or two moieties when the atoms joined by the bond are considered to be part of larger substructure. A bond may be single, double, or triple unless otherwise AS specified. A dashed line between two atoms in a drawing of a molecule indicates that an additional bond may be present or absent at that position.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder. As used herein, reference to "treatment" of a patient is intended to include prophylaxis.

The term "patient" means all mammals including humans. Examples of patients include humans, cows, dogs, cats, goats, sheep, pigs, and rabbits. Preferably, the patient is a human.

The term "prodrug" refers to a compound that is made more active in vivo. The present compounds can also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

STAT3 was discovered as a major component in the acute phase response to inflammation and as a key mediator of interleukin 6 (IL-6) and epidermal growth factor signaling. Akira, S., et al., *Molecular Cloning of APRF, A Novel IFN-Stimulated Gene Factor 3 P91-Related Transcription Factor Involved in the Gp130-Mediated Signaling Pathway*, Cell, 77, 63-71 (1994); Zhong; Z., et al., *STAT3: A STAT Family Member Activated By Tyrosine Phosphorylation in Response to Epidermal Growth Factor And Interleukin-6*, Science, 264, 95-98 (1994a); Zhong; Z., et al., *STAT3 And STAT4: Members of the Family of Signal Transducers and Activators of Transcription*, Proc. Nat. Acad. Sci., U.S.A., 91, 4806-4810 (1994b). Like all STATS, STAT3 is composed of an amino-terminal oligomerization domain, a coiled coil domain, a DNA binding domain, a linker domain, a Src homology 2 (SH2) domain, and a C-terminal transactivation domain.

Figure 2:
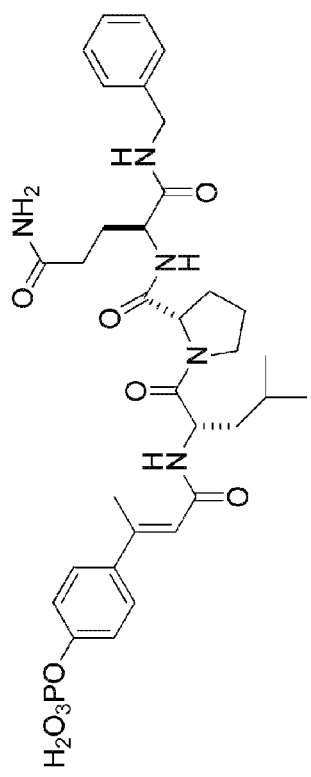
FIG. 2 shows the structure of inhibitors possessing β-methyl cinnamide and the four scaffolds.
Figure 2:
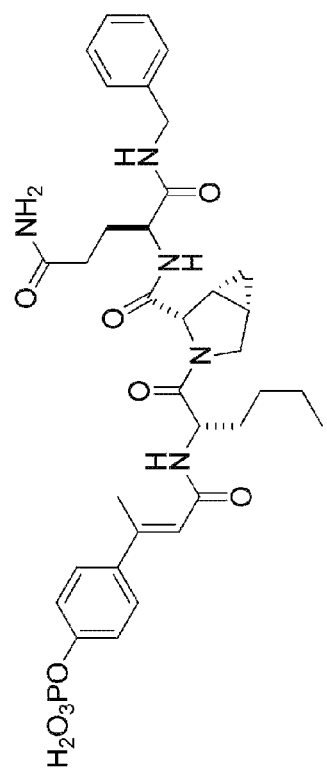
Figure 2:
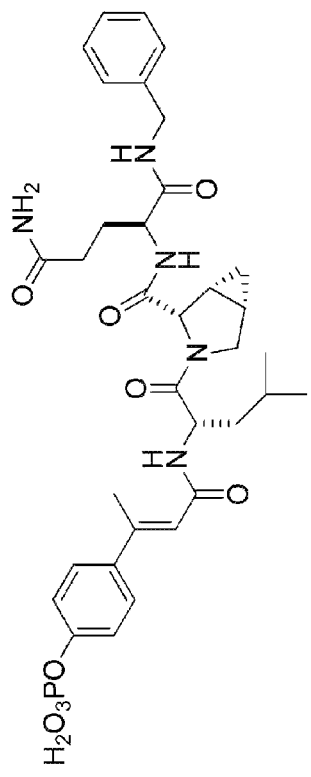
Figure 2:
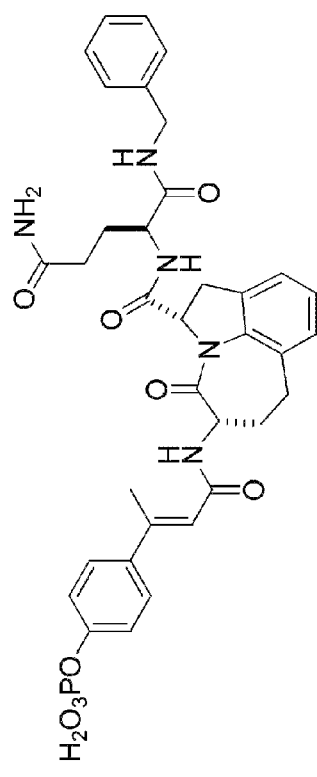

In IL-6 signaling, on binding of the cytokine to its receptor, JAK kinases are recruited to the co-receptor, gp130, which becomes phosphorylated on several tyrosine residues (FIG. 2). Stahl, N., et al., *Choice of STATs and Other Substrates Specified by Modular Tyrosine-Based Motifs In Cytokine Receptors*, Science, 267, 1349-1353 (1995), Gerhartz, C., et al., *Differential Activation of Acute Phase Response Factor/STAT3 and STAT1 via the Cytoplasmic Domain of the Interleukin 6 Signal Transducer gp130. I. Definition Of A Novel Phosphotyrosine Motif Mediating STAT1 Activation*, J. Biol. Chem., 271, 12991-12998 (1996). STAT3, via its SH2 domain, binds to the phosphotyrosine residues on gp130 and is then phosphorylated on Tyr705, a conserved tyrosine just C-terminal to the SH2 domain, by JAK2. Upon phosphorylation, termed activation, STAT3 forms homodimers and/or heterodimers with STAT1 via reciprocal interactions between the SH2 domains and the phosphotyrosine residue. The dimers then translocate to the nucleus and bind specific DNA sequences where they, in cooperation with other transcription factors, regulate gene expression. Bromberg, J., et al., *The Role of STATs in Transcriptional Control and Their Impact on Cellular Function*, Oncogene, 19, 2468-2473 (2000); Levy, D. E., et al., *STATs: Transcriptional Control and Biological Impact*, Nature Rev. Mol. Cell. Blot., 3, 651-662 (2002); Stark, G. R., et al., *How Cells Respond to Interferons*, Ann. Rev. Biochem., 67, 227-264 (1998).

Downstream targets of STAT3 include Bcl-$x_L$, a member of the bcl-2 family of anti-apoptotic proteins, cell cycle regulators such as cyclin D1 and p21$^{WAF1/CIP1}$ and other transcription factors including c-myc and c-fos. In EGF signaling, STAT3 has been reported to bind directly to phosphotyrosine residues on the EGFR and to be activated by the kinase activity of the receptor. Zhong; Z., et al., *STAT3 and STAT4: Members of the Family of Signal Transducers and Activators of Transcription*, Proc. Nat. Acad. Sci., U.S.A., 91, 4806-4810 (1994b); Zhang, T., et al., *Grb2 Regulates STAT3 Activation Negatively in Epidermal Growth Factor Signaling*, Biochemical J., 376, 457-464 (2003). Src kinases first bind to EGFR via their SH2 domains and recruit STAT3 via SH3 domain interactions with polyproline helices. Schreiner, S. J., et al., *Activation of STAT3 by The Src Family Kinase Hck Requires a Functional SH3 Domain*, J. Biol. Chem., 277, 45680-45687 (2002).

STAT3 transmits signals from other IL-6-type cytokines that utilize gp130 such as ciliary neurotrophic factor, leukemia inhibitory factor, oncostatin M, IL-10, and granulocyte colony-stimulating factor. Weber-Nordt, R. M., et al., *Constitutive Activation of STAT Proteins In Primary Lymphoid And Myeloid Leukemia Cells and in Epstein-Barr Virus (EBV)-Related Lymphoma Cell Lines*, Blood, 88, 809-816 (1996a). In addition to cytokines, it has also been shown to be involved in signaling from the epidermal growth factor, platelet derived growth factor, and vascular endothelial growth factor. STAT3 has also been shown to upregulate VEGF expression and thus has a potential role in angiogenesis. Niu, G., et al., *Constitutive STAT3 Activity Up-Regulates VEGF Expression and Tumor Angiogenesis*, Oncogene, 21, 2000-2008 (2002a).

The compounds of the subject invention include prodrugs that can bind with relatively high affinity to STAT3 protein and as such disrupt STAT3 signaling activity and block signaling in tumor cells or other tissues in which STAT3 is constitutively expressed. However, affinity for STAT3 is not the final parameter as some less avid compounds have been shown to be more potent in biological assays and have been shown to passively diffuse through a cell membrane in physiological conditions.

As such, a series of compounds that may inhibit dimerization and subsequent transcription of STAT3 are described herein. Such compounds were designed and/or derived from the amino acid sequence surrounding tyrosine 904 of the receptor molecule, gp130:pTyr$^{904}$-Leu-Pro-Gln. Substitutions to the tyrosine residue, such as replacing the Leu-Pro dipeptide unit with fused ring heterocycles such as Haic, and to the C-terminus were analyzed. Compounds were assayed for their ability to bind to STAT3 by competition with a fluorescein-labeled phosphopeptide and measurement of the fluorescence polarization. Several of the disclosed inhibitors possess IC$_{50}$ values in the range of 35-200 nM. Certain compounds were then converted to phosphatase-stable, cell permeable prodrugs that inhibit STAT3 phosphorylation at concentrations as low as 100 nM.

More specifically, the Tyr-Xxx-Xxx-Gln motif that was determined to be the receptor binding determinant for STAT3. Based on this discovery four scaffolds were developed, Leu-Pro, Leu-mPro, Nle-mPro, and Haic, that were used to present aryl phosphate phosphotyrosine mimics and glutamine surrogates (mPro=cis-3,4-methanoproline). See FIGS. 1. 4-phosphoryloxycinnamide (pCinn) was found to have a high affinity replacement for phosphotyrosine. A benzyl amide appended to the backbone carboxyl group of glutamine also provided high affinity interactions with STAT3. pCinn and Gln-NHBn were attached to the N- and C-termini of one of four scaffolds to provide the compounds (FIG. 1).

Certain compounds were then evaluated for their ability to compete with a fluorescein-labeled phosphopeptide, FAM-Ala-pTyr-Leu-Pro-Gln-Thr-Val-NH$_2$ SE ID NO: (FAM=5-carboxyfluorescein), for binding to full length STAT3, using a fluorescence polarization assay. Coleman, IV, D. R., et al., *Investigation of the Binding Determinants of Phosphopeptides Targeted To The SH2 Domain Of STAT3. Development of a High Affinity Peptide Inhibitor*, J. Med. Chem., 48, 6661-6670 (2005). Certain compounds were then modified to test the effects of different functional groups with the goal of increasing affinity before converting to cell permeable drugs. Such compounds are provided immediately below.

pCinn-Leu-Pro-Xxx Analogs:
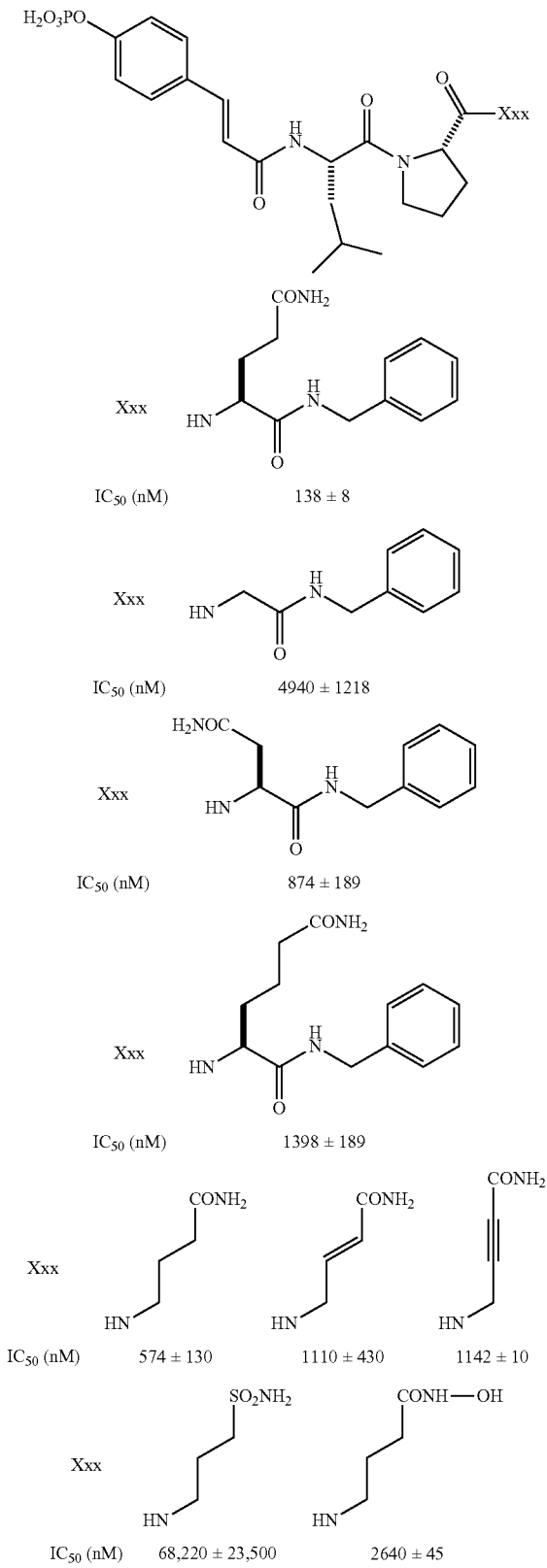
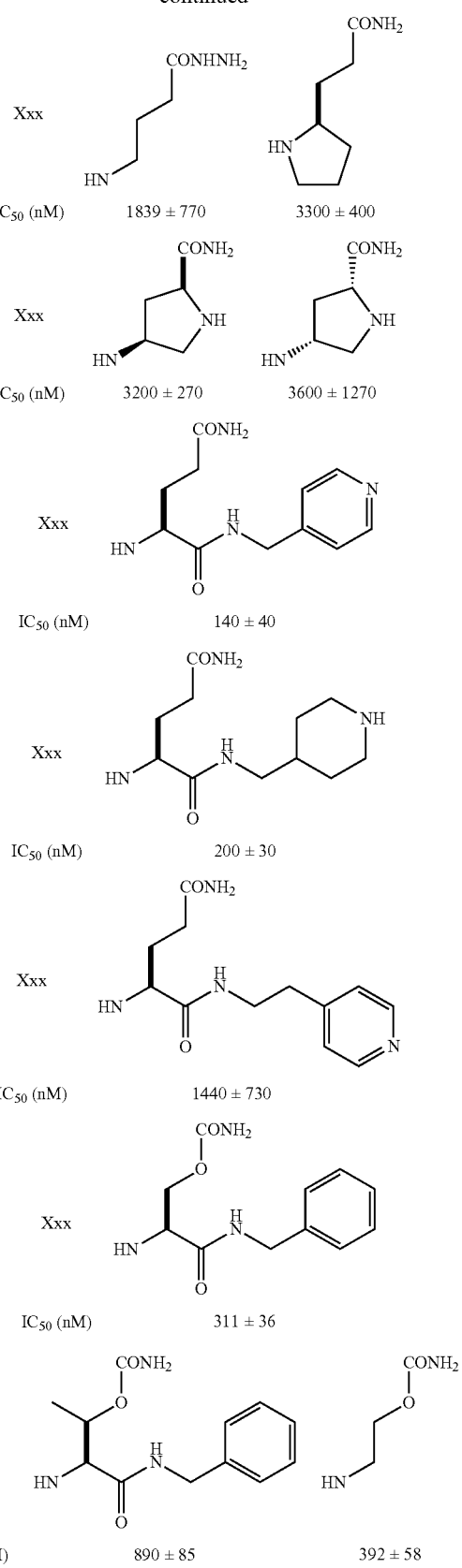

-continued

| Xxx | IC$_{50}$ (nM) |
|---|---|
| (S)-CH(CH$_3$)-CH$_2$-O-CONH$_2$ | 797 ± 29 |
| -NH-CH$_2$-CH$_2$-NH-CONH$_2$ | 131 ± 130 |
| -NH-CH(CH$_3$)-CH$_2$-NH-CONH$_2$ | 1350 ± 130 |
| -NH-CH(CH$_2$OBn)-CH$_2$-O-CONH$_2$ | 454 ± 21 |
| -NH-CH(CH$_3$)(OBn)-CH$_2$-O-CONH$_2$ | 6900 ± 350 |
| -NH-CH$_2$-CH(OH)-CH$_2$-CONH$_2$ | 3120 ± 340 |
| -NH-CH(CH$_2$OBn)-CH$_2$-NH-C(=NH)-NH$_2$ (urea) | — |
| 4-hydroxybenzyl glutamine analog | 840 ± 120 |
| -N(CH$_2$Ph)$_2$ side chain glutamine | 1080 ± 360 |
| piperidinyl side chain glutamine | 1210 ± 190 |
| N-Me piperazinyl glutamine | 1300 ± 230 |
| morpholinyl glutamine | 1530 ± 70 |
| (S)-methyl glutamine | 110 ± 30 |
| (R)-methyl glutamine | 1180 ± 30 |

-continued

| Xxx | IC$_{50}$ (nM) |
|---|---|
| iPr glutamine analog | 1880 ± 220 |
| iBu glutamine analog | 4900 ± 610 |
| n-butyl glutamine analog | 1350 ± 360 |
| -CH$_2$-O-Bn glutamine analog | 294 ± 40 |
| -CH(CH$_3$)-O-Bn glutamine analog | 272 ± 7 |
| -CH$_2$-NH$_2$ glutamine analog | 1235 ± 215 |
| -CH$_2$-NH-Ac glutamine analog | 580 ± 173 |
| -CH$_2$-O-C(O)NH$_2$ glutamine analog | 615 ± 30 | pCinn-Leu-mPro-Xxx Analogs:

[Structure: H$_2$O$_3$PO-C$_6$H$_4$-CH=CH-C(O)-NH-CH(iBu)-C(O)-N(mPro cyclopropane-fused pyrrolidine)-C(O)-Xxx]

| Xxx | IC$_{50}$ (nM) |
|---|---|
| -NH-CH(CH$_2$Ph)-C(O)-NH-CH$_2$-CONH$_2$ (benzyl) | 68 ± 8 |
| -NH-CH$_2$-CH$_2$-CH$_2$-CONH$_2$ | 303 ± 48 |

21
-continued

22
-continued

Xxx

IC$_{50}$ (nM): 175 ± 35, 511 ± 67, 1630 ± 132, 699 ± 62, 94 ± 11

69 ± 11, 437 ± 4, 290 ± 41

Substituted Proline Analogues

IC$_{50}$ (nM): 155 ± 31, 121 ± 16

IC$_{50}$ (nM): 246 ± 62, 317 ± 14

-continued

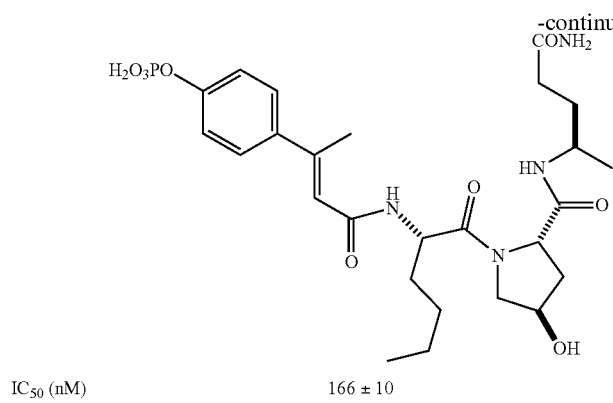

IC$_{50}$ (nM)　　　　　166 ± 10

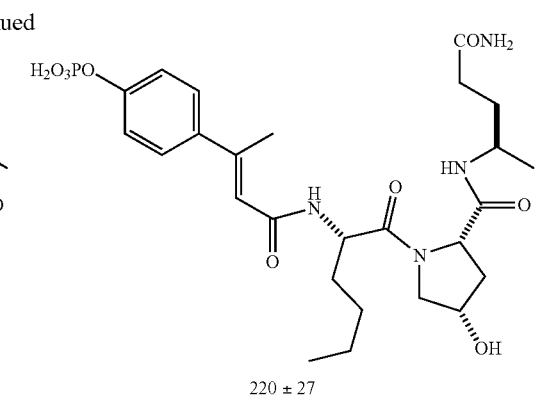

220 ± 27

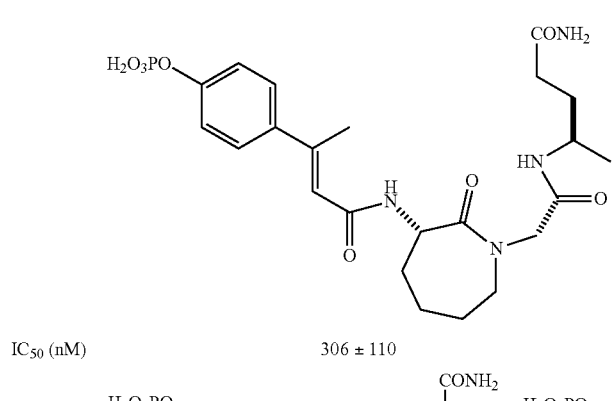

IC$_{50}$ (nM)　　　　　306 ± 110

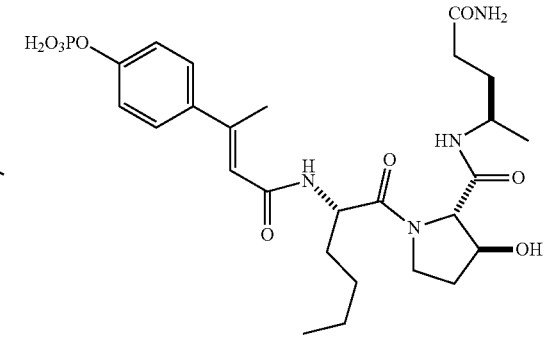

221 ± 19

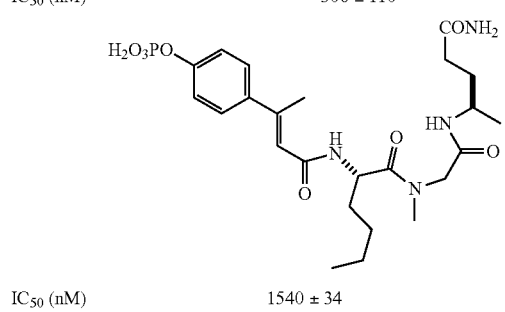

IC$_{50}$ (nM)　　　　　1540 ± 34

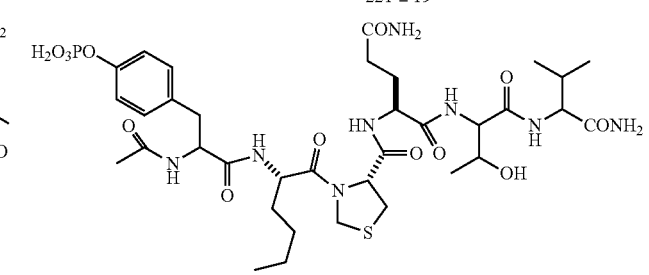

645 ± 63

TABLE 1

Effect of glutamine mimics on the affinity of peptidomimetics for STAT3.

| | Xxx | | |
|---|---|---|---|
| | CONH$_2$ branched-chain amine | CONH$_2$ oxy-linked | CONH$_2$ NH-linked |
| Compound IC$_{50}$ (nM) pβMCinn-Leu-Pro-Xxx | 154 ± 10 | 216 ± 34 | 100 ± 7 |
| Compound IC$_{50}$ (nM) pβmCinn-Leu-mPro-Xxx | 88 ± 11 | 206 ± 40 | 42 ± 11 |
| Compound IC$_{50}$ (nM) pβMCinn-Nle-mPro-Xxx | 70 ± 14 | 122 ± 15 | 49 ± 6 |
| Compound IC$_{50}$ (nM) pβMCinn-Haic-Xxx | 112 ± 23 | 201 ± 14 | 412 ± 44 | pβMCinn = 3-(4-phosphoryloxyphenyl)-but-2-enoate

The term "therapeutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides.

Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The compounds of the present invention can exist as therapeutically acceptable salts. The present invention includes compounds listed above in the form of salts, in particular acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. For a more complete discussion of the preparation and selection of salts, refer to *Pharmaceutical Salts: Properties, Selection, and Use* (Stahl, P. Heinrich. Wiley-VCHA, Zurich, Switzerland, 2002).

Thus, preferred salts include hydrochloride, hydrobromide, sulfonate, citrate, tartrate, phosphonate, lactate, pyruvate, acetate, succinate, oxalate, fumarate, malate, oxaloacetate, methanesulfonate, ethanesulfonate, p-toluenesulfonate, benzenesulfonate and isethionate salts of compounds of the present invention. A salt of a compound can be made by reacting the appropriate compound in the form of the free base with the appropriate acid.

While it may be possible for the compounds of the subject invention to be administered as the raw chemical, it is also possible to present them as a pharmaceutical formulation. Accordingly, the subject invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described. Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Compounds of the present invention may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Gels for topical or transdermal administration of compounds of the subject invention may comprise, generally, a mixture of volatile solvents, nonvolatile solvents, and water. The volatile solvent component of the buffered solvent system may preferably include lower (C1-C6) alkyl alcohols, lower alkyl glycols and lower glycol polymers. More preferably, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. Preferably, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess will result in a lack of bioavailability due to poor release of drug from solvent mixture. The buffer component of the buffered solvent system may be selected from any buffer commonly used in the art; preferably, water is used. The preferred ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation the compounds according to the invention are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflators. Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds of the subject invention can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, the present invention provides methods for treating STAT3-mediated disorders in a human or animal subject in need of such treatment comprising administering to said subject an amount of a compound of the present invention effective to reduce or prevent said disorder in the subject in combination with at least one additional agent for the treatment of said disorder that is known in the art. In a related aspect, the present invention provides therapeutic compositions comprising at least one compound of the present invention in combination with one or more additional agents for the treatment of STAT3.

The compounds of the subject invention may be useful for the treatment or disorders of a wide variety of condition where inhibition or modulation of STAT3 is useful. Disorders or conditions advantageously treated by the compounds of the subject invention include the prevention or treatment of cancer, such as colorectal cancer, and cancer of the breast, lung, prostate, bladder, cervix and skin. Compounds of the invention may be used in the treatment and prevention of neoplasias including but not limited to brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers.

Other disorders or conditions which can be advantageously treated by the compounds of the present invention are inflammation. The compounds of the present invention are useful as anti-inflammatory agents with the additional benefit of having significantly less harmful side effects. The compounds are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds of the subject invention may also be useful in treating psoriasis. The compounds may also be used to treat gastrointestinal conditions such as inflammatory bowel disease, Crohn's disease, gastritis, irritable bowel syndrome and ulcerative colitis. The compounds may also be used in the treatment of pulmonary inflammation, such as that associated with viral infections and cystic fibrosis. In addition, compounds of invention are also useful in organ transplant patients either alone or in combination with conventional immunomodulators.

Besides being useful for human treatment, the compounds and formulations of the present invention are also useful for veterinary treatment of companion animals, exotic animals and farm animals, including mammals, rodents, and the like. More preferred animals include horses, dogs, and cats.

General Synthetic Methods for Preparing Compounds

The following scheme can be used to practice the present invention. Examples 1 to 25 can be synthesized using the following general and exemplary synthetic procedure of bis-protected phosphinyldifluormethylcinnamates for incorporation into prodrugs. Both 4-nitrophenyl esters and pentachlorophenyl esters are effective. The same synthesis strategy can be used to incorporate any of a variety of acyloxymethyl esters attached to the difluoromethyl phosphonate group.

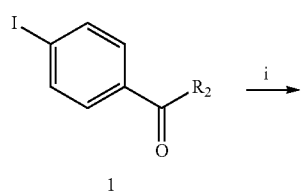

1

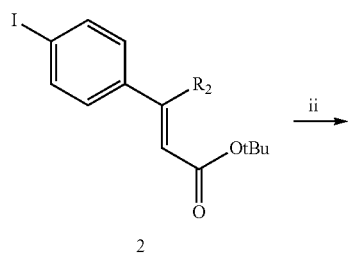

2

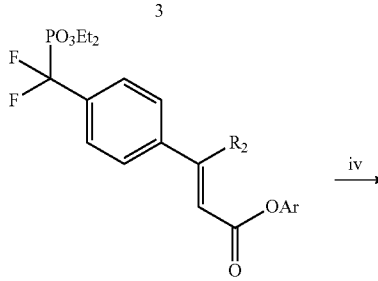

3

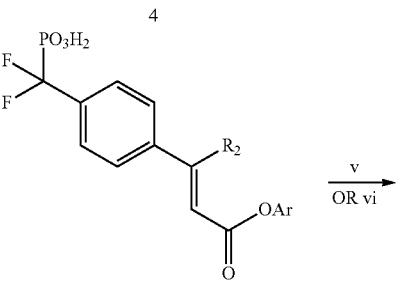

4

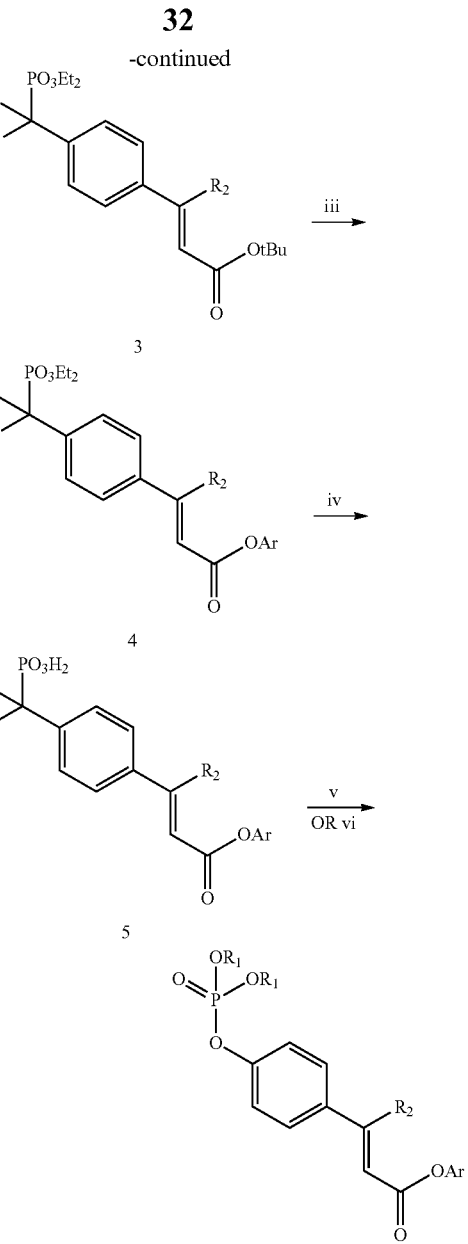

5

6

| | $R_2$ | Ar |
|---|---|---|
| a | H | 1 $C_6Cl_5$ |
| b | $CH_3$ | 2 $4\text{-}NO_2\text{---}C_6H_4$ |

Reagents and conditions (i) $(EtO)_2POCH_2CO_2tBu$; (ii) $BrCdCF_2PO_3Et_2$, CuCl; (iii) (a) TFA, (b) ArOH, DCC; (iv) TMS-I; (v) (a) $SOCl_2$, (b) $R_1OH$, $Et_3N$; (vii) (a) NaOH, (b) $AgNO_3$, (c) $R_5CO_2CH_2I$.

Scheme 2 represents the synthesis of alkyl and aryl esters of phosphates.

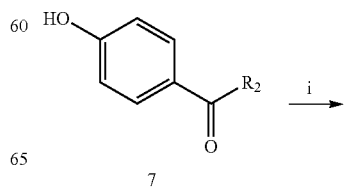

7

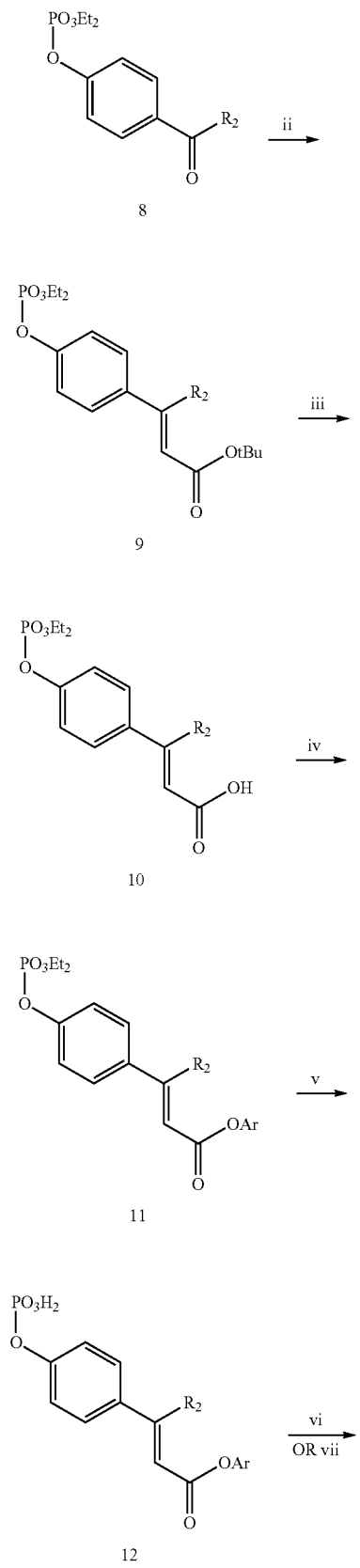

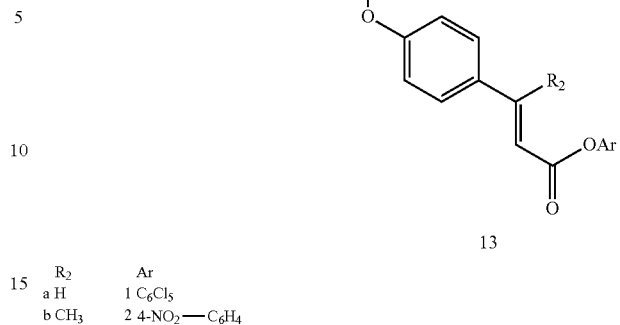

| $R_2$ | | Ar | |
|---|---|---|---|
| a | H | 1 | $C_6Cl_5$ |
| b | $CH_3$ | 2 | 4-$NO_2$—$C_6H_4$ |

Reagents and conditions: (i) Diethylchlorophosphate, TEA, $CH_2Cl_2$, 0° C. to r.t. overnight; (ii) Li$^t$OBu, $^t$BuOH, (EtO)$_2$POCH$_2$CO$_2$$^t$Bu, r.t. overnight ; (iii) TFA/CH$_2$Cl$_2$ (95:5) 1 h (iv) ArOH, DCC; (v) TMS-I; (vi) (a) SOCl$_2$, (b) R$_1$OH, Et$_3$N; (vii) (a) NaOH, (b) AgNO$_3$, (c) R$_5$CO$_2$CH$_2$I.

To prepare prodrugs in which X=CF$_2$, we employed the active ester building block approach recently described by us (Mandal et al. Org Lett, 2009, 11, 3394-3397) (Scheme 1). Starting from iodoacetophenone (1), Horner-Emmons coupling with tert-butyl (diethylphosphono)acetate gave the iodocinnamate, 2. $^t$BuOH was used as the solvent and the cis and trans isomers were separated by silica gel chromatography. Copper-cadmium cross coupling with diethyl bromodifluoromethyl-phosphonate (Qabar) provided phosphonate 3. Acidolytic removal of the tert-butyl ester followed by esterification with pentachlorophenol gave intermediate 4. Trimethylsilyl iodide treatment removed the phosphonate ethyl groups resulting in phosphonic acid 5. For the synthesis of alkyl, aryl, or heterocylic di-esters, activation of the phosphoryl group with oxalyl chloride followed by treatment with alcohols (R$_1$OH) gives intermediate 6 that can be coupled to peptide or peptidomimetic intermediates. For acyloxymethyl (AOM) esters such as POM or benzyloxymethyl, conversion of 5 to the silver salt followed by alkylation with an acyloxymethyl iodide provided the bis-AOM ester, 6.

For prodrugs in which X=O, Scheme 2 gives the synthesis of phosphate diester cinnamic acid units, 13. Hydroxybenzaldehyde was treated with diethyl chlorophosphate to give intermediate 8, which was elongated by homer-Emmons vinylogation to give trimester 9. After cleavage of the tert-butyl ester (10) and conversion to an aryl ester (11), the phosphono ethyl ester groups are cleaved with TMS-I (12). For the synthesis of alkyl, aryl, or heterocylic di-esters, activation of the phosphoryl group with oxalyl chloride followed by treatment with alcohols (R$_1$OH) gives intermediate 13 that can be coupled to peptide or peptidomimetic intermediates. For acyloxymethyl (AOM) esters such as POM or benzyloxymethyl, conversion of 12 to the silver salt followed by alkylation with an acyloxymethyl iodide provided the bis-AOM ester.

In cases where R$_1$=acyloxymethyl groups, e.g. pivaloyloxymethyl, prodrugs were formed by solution phase coupling of corresponding derivatives of 6 or 13 to Haic-XXX, or Nle-mPro-XXX, which were synthesized on Rink resin, cleaved from the resin and were purified by reverse phase HPLC before use (Scheme 3). Acylation of the dipeptides was accomplished with catalytic amounts of dimethylaminopyridine under anhydrous conditions. Prodrugs were purified by RP-HPLC using gradients of ACN in water with no TFA or other additives. All prodrugs were >98% pure by reverse phase HPLC and gave the correct mass by high resolution mass spectrometry.

Scheme 3

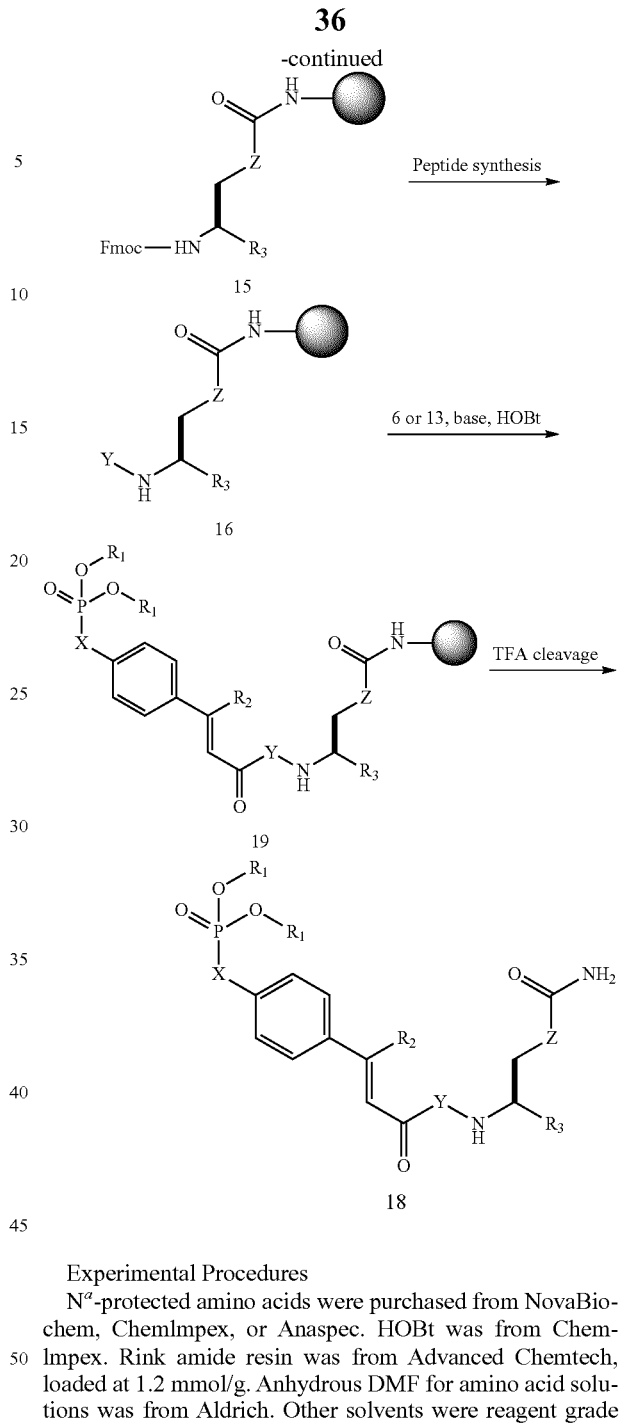

In cases where $R_1$ is an alkyl, aryl, or heterocyclic group, prodrugs can be synthesized by solid phase coupling of 6 or 13 to resin-bound peptide intermediates, provided that $R_1$ esters are not acid labile. (Scheme 4).

Scheme 4

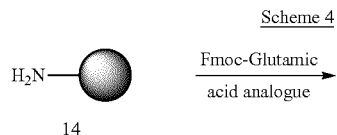

Experimental Procedures $N^\alpha$-protected amino acids were purchased from NovaBiochem, Chemlmpex, or Anaspec. HOBt was from Chemlmpex. Rink amide resin was from Advanced Chemtech, loaded at 1.2 mmol/g. Anhydrous DMF for amino acid solutions was from Aldrich. Other solvents were reagent grade and were used without further purification. NMR spectra were obtained on either a Bruker DPX 300 MHz spectrometer or a Bruker DRX 500 MHz spectrometer. Fmoc-Glu-NHBn was prepared as described in Coleman IV, D. R., et al. *Investigation of the binding determinants of phosphopeptides targeted to the SH2 domain of Stat3. Development of a high affinity peptide inhibitor*. J. Med. Chem. 48, 6661-6670 (2005). (R)-4-(9-fluorenylmethoxycarbonlyamino)-pentanoate was prepared as described by Mandal, P. K.; McMurray, J. S. *Pd—C Induced Catalytic Transfer Hydrogenation with Triethylsilane*. J. Org. Chem. 72, 6599-660 (2007), and 4-nitrophenyl 2-(9-fluorenylmethoxycarbonlyamino)ethyl carbamate was prepared as described in Boeijen et al., (2001), and 4-nitrophenyl 2-(9-fluorenyloxycarbonlyamino) ethylcarbonate, (Boeijen, A. et al., Solid-phase synthesis of oligourea peptidomimetics employing the Fmoc protection strategy. J Org Chem 66, 8454-62 (2001)), and (4R,5S)-4-(9-fluorenyloxycarbonlyamino)-5-benzyloxyhexanoate were prepared as described by (Mandal, P. K. et al., *Structure-Affinity Relationships of Glutamine Mimics Incorporated into Phosphopeptides Targeted to the SH2 Domain Of Signal Transducer And Activator Of Transcription* 3. J Med Chem 52, 6126-41 (2009). Racemic Fmoc-cis-3,4-methanoproline was purchased from Novabiochem. Phosphopeptide mimetics were assayed for affinity to STAT3 using fluorescence polarization as described by Coleman IV, D. R., et al. *Investigation of the Binding Determinants of Phosphopeptides Targeted to the SH2 Domain of STAT3. Development of a high affinity peptide inhibitor.* J. Med. Chem. 48, 6661-6670 (2005).

General Procedure for the synthesis of peptides and peptidomimetics. Solid phase syntheses were carried out manually using commercially available Rink resin. Resin, 0.2 gm, was placed in a manual reactor and swollen and washed with 5×10 mL of DMF/CH$_2$Cl$_2$. Fmoc groups were removed with 3×6 mL of 20% piperidine/DMF for 5 min each. For coupling, three-fold excesses of Fmoc-amino acids, DIC, and HOBt were used in 8-10 mL of DMF/CH$_2$Cl$_2$ and were allowed to proceed until resin samples tested negative with ninhydrin tests. 4-Nitrophenyl 2-(9-fluorenylmethoxycarbonlyamino) ethyl carbamate and 4-nitrophenyl 2-(9-fluorenyloxycarbonlyamino)ethylcarbonate were coupled to Rink resin by addition of 3 eq plus 3 eq of DIEA in 8-10 mL of DMF/CH$_2$Cl$_2$ until ninhydrin tests were negative. For Fmoc-Haic, Fmoc-cis-3,4-methanoproline, and phosphorylated cinnamic acid derivatives, couplings were performed with 1.5 equivalents each of acid, DIC and HOBt in DMF/CH$_2$Cl$_2$ overnight or until ninhydrin tests were negative. After coupling and deprotection steps, resins were washed with 5×10 mL of DMF/CH$_2$Cl$_2$. On completion of the peptide chain, resins were washed with CH$_2$Cl$_2$ (3×10 mL) and were treated with TFA:Triisopropylsilane:H$_2$O (95:2.5:2.5) Pearson, D. A. et al. *Trialkylsilanes As Scavengers For The Trifluoroacetic Acid Deblocking of Protecting Groups In Peptide Synthesis.* Tetrahedron Lett. 30, 2739-2742 (1989) (3×5 mL) for 15 min each. The combined filtrates sat at rt for 1-2 h and the volumes were reduced in vacuo. Peptides were precipitated in ice cold Et$_2$O, collected by centrifugation, and washed 2×more with the same solvent and centifuged. After drying, peptides were purified by reverse phase HPLC on a Rainin Rabbit HPLC or a Varian Dynamax HPLC using a Phenomenex Luna C18(2) 10 μM 2.1×25 cm column. Gradients of ACN in H$_2$O or ACN in 0.01 M NH$_4$OAc (pH 6.5) at 10-20 mL/min were employed. For phosphopeptides, solvents contained 0.1% TFA. For prodrugs, no TFA was used in the mobile phase. Peptides were tested for purity by reverse phase HPLC on a Hewlett Packard 1090 HPLC or an Agilent 1100 HPLC using a Phenomenex Luna C 18(2) 5 μM 4.6×250 mm column. A gradient of 0-40% ACN/30 min was used for posphopeptides and peptide intermediates. For prodrugs the gradient was 10-80% ACN/30 min. Phosphopeptides and prodrug intermediates were dried in vacuo over P$_2$O$_5$ at 37° for 24 h prior to use (Coleman et al, 2005).

Synthesis of tent-butyl (E) 3-(4-iodophenyl)-but-2-enoate (2b): A solution of tert-butyl diethylphosphonoacetate (10.0 g, 39.6 mmol) in 30 mL of dry THF was added slowly to a freshly prepared solution of 19 mL of 2.5 M (hexanes) lithium tert-butoxide and tBuOH (30 mL) and stirred for 1 h. A solution of 4-iodoacetophenone (1b) (9.0 g, 36.6 mmol) in 20 mL of dry THF was added to the reaction mixture and stirring was continued overnight. The solvents were removed under vacuum. The residue was dissolved in 400 mL of Et$_2$O and was washed with water (2×30 mL) followed by brine (30 mL) and dried over MgSO$_4$. After filtration and evaporation of the solvent, the crude product was then purified by silica gel column chromatography, eluting with 1% EtOAc in hexane. The product 2b was obtained as an oil (10.0 g, 79% yield). $^1$HNMR (CDCl$_3$, 300 MHz) δ 1.515 (s, 9H), 2.48 (s, 3H), 6.03 (s, 1H), 7.18 (d, 2H, J=8.4 Hz), 7.68 (d, 2H, J=8.4 Hz). $^{13}$C NMR (CDCl$_3$, 75.0 MHz) δ 17.5, 28.3, 80.2, 94.6, 119.5, 128.0, 137.6, 141.9, 152.6, 166.1. Anal. Calcd. for C$_{14}$H$_{17}$IO$_2$: C, 48.85; H, 4.98; I, 36.87; 0, 9.3 : Found C, 49.40; H, 5.00, I, 35.97. HRMS (M+H) calc, 345.0351; found, 345.0319.

Synthesis of tert-butyl (2E) 3-[4-[(diethoxyphosphinyl)difluoromethyl]phenyl]-but-2-enoate (3b): To a solution of diethyl bromodifluoromethylphosphonate (6.45 g, 24.1 mmol) in dry DMF (100 mL), cadmium powder (5.41 g, 48.2 mmol) was added. The suspension was stirred for 8 h under argon. Unreacted cadmium was removed by filtration under argon and the filtrate was treated with CuCl (2.86 g, 28.9 mmol) and 2b (5.00 g, 15.1 mmol) at room temperature for 24 h. Et$_2$O, 400 mL, was added and the mixture was stirred for 5 min and filtered. The organic layer was washed with saturated NH$_4$Cl (2×40 mL) and water (4×40 mL), dried (MgSO$_4$) and evaporated to give an oily residue. The crude product was purified by silica gel column chromatography with 40% EtOAc-hexane (v/v) as the eluent to give 4.0 g (68%) of 3b as a colorless oil. $^1$H NMR (CDCl$_3$, 300 MHz) δ1.3-1.35 (m, 6H), 1.52 (s, 9H), 2.54 (s, 3H), 4.13-4.28 (m, 4H), 6.07 (s, 1H) 7.53 (d, J=8.4 Hz, 2H), 7.61 (d, J=8.4 Hz, 2H). $^{13}$C NMR (CDCl$_3$, 75.0 MHz) δ 16.3, 16.4, 17.7, 28.3, 64.8, 64.9, 80.3, 120.4, 126.4, 145.0, 152.7, 166.0. $^{19}$F NMR (CDCl$_3$, 282.0 MHz) δ −108.57 (d, J=115.6 Hz, 2F). $^{31}$P NMR (CDCl$_3$, 202.0 MHz) δ 6.15 (t, J=115.1 Hz, 1P). Anal. Calcd for C$_{19}$H$_{27}$F$_2$O$_5$P: C, 56.43; H, 6.73; F, 9.4; O, 19.78; P, 7.66: Found C, 56.13; H, 6.73; F, 9.15. HRMS (M+H) calc, 405.1642; found, 405.1698.

Synthesis of Pentachlorophenyl (2E)-3-[4-[(diethoxyphosphinyl)difluoromethyl]phenyl]-but-2-enoate (4b1): A solution of 3b (4.00 g, 9.9 mmol) in 5 mL dry CH$_2$Cl$_2$ was treated with 20 mL of TFA for 1 h at room temperature. The TFA was removed in vacuo and residual acid was removed by addition and evaporation of toluene (2×10 mL). The crude cinnamic acid derivative (3.5 g, 9.8 mmol), pentachlorophenol (2.8 g, 10.7 mmol), DCC (3.0 g, 14.7 mmol) and DMAP (0.120 g, 0.98 mmol) in 100 mL of EtOAc was stirred at room temperature for 24 h. The mixture was filtered through celite and the solvent removed in vacuuo. The crude product was purified by silica gel chromatography eluting with 25% EtOAc-hexanes to give 5.1 g (84%) of 4b as white solid. $^1$H NMR (CDCl$_3$, 300 MHz) δ 1.34-1.4 (m, 6H), 2.67 (s, 3H), 4.18-4.32 (m, 4H), 6.5 (s, 1H), 7.65-7.72 (m, 4H). $^{13}$C NMR (CDCl$_3$, 75.0 MHz) δ16.3, 16.4, 18.5, 64.8, 64.9, 114.9, 126.56, 126.58, 126.65, 126.71, 126.74, 126.8, 127.93, 131.4, 132.0, 143.63, 144.24, 160.5, 161.73. $^{19}$F NMR (CDCl$_3$, 282.0 MHz) δ −108.8 (d, J=112.8 Hz, 2F). Anal. Calcd for C$_{21}$H$_{18}$Cl$_5$F$_2$O$_5$P: C, 42.28; H, 3.04; Cl, 29.71; F, 6.37; Found C, 42.48; H, 3.15; Cl, 29.45; F, 6.25. HRMS (M+H) calc, 594.9381; found, 594.9357.

Synthesis of pentachlorophenyl (2E)-3-[4(phosphoryldifluoromethyl)phenyl]-but-2-enoate(5b1): Iodotrimethylsilane (2.0 mL, 13.4 mmol) in 5 mL of dry CH$_2$Cl$_2$ was added dropwise to a solution of 4b1 (2.0 g, 3.35 mmol) and bis(trimethylsilyl)trifluoroacetamide (1.8 mL, 6.8 mmol) in 20 mL of dry CH$_2$Cl$_2$ at 0° C. under argon. Stirring was continued for 1 h at 0° C. and 1 h at room temperature. The solution was concentrated in vacuo. The residue was taken up in 20 mL MeCN/H$_2$O/AcOH (8:1:1), stirred for 45 min and concentrated in vacuo. Toluene (5 mL) was added and evaporated twice. On addition of Et$_2$O solids separated, which were collected by filtration and washed with the same solvent to give 1.6 g of 5b1 as a white powder (89%). It was used directly in the next step with no purification. HRMS (M+H) calc, 538.8755; found, 538.8773.

Synthesis of pentachlorophenyl (2E)-3-[4-[[bis[(2,2-dimethyl-1-oxopropoxy)methoxy]phosphinyl]difluoromethyl]phenyl]-but-2-enoate (6b1, R$_1$=pivaloyloxymethyl): NaOH (144 mg, 3.6 mmol) in 2 mL of H$_2$O was added dropwise to a stirred suspension of 5b1 (1 g, 1.9 mmol) in 5 mL of H$_2$O. When the mixture became clear (pH~9), AgNO$_3$ (807 mg, 4.75 mmol) was added. After 2 h at 4° C. the gray precipitate was collected by filtration, dried, and pulverized in a mortar and pestle. The powder was suspended in dry toluene (10 mL) and pivyloxymethyl iodide (1.4 g, 5.7 mmol) was added and stirred for 48 h at room temperature. After filtration the solvent was removed in vacuo and the crude product was purified by silica gel column chromatography eluting with 30% EtOAc-hexanes to give colorless sticky liquid of 6b1 (0.9 g, 64%). $^1$H NMR (CDCl$_3$, 500 MHz) δ 1.23 (s, 18H), 2.65 (s, 3H), 5.66-5.76 (m, 4H), 6.47 (s, 1H), 7.66 (m, 4H). $^{13}$C NMR (CDCl$_3$, 125 MHz) δ18.5, 26.8, 38.8, 82.4, 82.5, 115.1, 126.6, 126.7, 126.8, 127.9, 131.4, 132.0, 144.0, 144.2, 160.3, 161.7, 176.5. $^{19}$F NMR (CDCl$_3$, 282.0 MHz) δ –109.22 (d, J=124.0 Hz, 2F). $^{31}$P NMR (CDCl$_3$, 202.0 MHz) δ 4.81 (t, J=123.2 Hz, 1P). Anal. Calcd for C$_{29}$H$_{30}$Cl$_5$F$_2$O$_9$P: 45.31; H, 3.93; Cl, 23.06; F, 4.94: Found C, 45.12; H, 3.93; Cl, 22.90; F, 5.08. HRMS (M+H) calc, 767.0116; found, 767.0124.

Synthesis of 4-nitrophenyl (2E)-3-[4-[(diethoxyphosphinyl)difluoromethyl]phenyl]-but-2-enoate (4b2): A solution of 3b (4.00 g, 9.9 mmol) in 5 mL dry CH$_2$Cl$_2$ was treated with 20 mL of trifluoroacetic acid for 1 h at room temperature. The TFA was removed in vacuo and residual acid was removed by addition and evaporation of toluene (2×10 mL). The crude cinnamic acid derivative (3.5 g, 10.0 mmol), p-nitrophenol (1.7 g, 12.0 mmol) and DCC (3.0 g, 14.7 mmol) in 100 mL of EtOAc were stirred at room temperature for 24 h. The mixture was filtered through celite and the solvent removed in vacuuo. The crude product was purified by silica gel chromatography eluting with 25% EtOAc in hexanes to give 3.8 g (80%) of 4b2 as white solid. $^1$H NMR (CDCl$_3$, 300 MHz) δ 1.32-1.4 (m, 6H), 2.66 (s, 3H), 4.16-4.18 (m, 4H), 6.37 (s, 1H), 7.35 (d, J=9.0 Hz, 4H), 7.6-7.7 (m, 4H), 8.3 (d, J=9.0 Hz, 2H). $^{13}$C NMR (CDCl$_3$, 75.0 MHz) 616.3, 16.4, 18.4, 64.8, 64.9, 116.3, 122.5, 125.2, 126.5, 126.6, 126.7, 126.8, 143.9, 145.2, 155.5, 159.2, 163.5. $^{19}$F NMR (CDCl$_3$, 282.0 MHz) δ –108.8 (d, J=112.8 Hz, 2F). $^{31}$P NMR (CDCl$_3$, 202.0 MHz) δ 5.94 (t, J=113.1 Hz, 1P).

Anal. Calcd for C$_{21}$H$_{22}$F$_2$NO$_7$P: C, 53.74; H, 4.72; F, 8.1; N, 2.98; O, 23.86; P, 6.6: Found C, 53.84; H, 4.72; F, 8.12; N, 3.12.

Synthesis of 4-nitrophenyl (2E)-3-[4-(phosphoryldifluoromethyl)phenyl]-but-2-enoate (5b2): Iodotrimethylsilane (2.5 mL, 17.0 mmol) in 10 mL of dry CH$_2$Cl$_2$ was added dropwise to a solution of 4b2 (2.0 g, 4.26 mmol) in 20 mL of dry CH$_2$Cl$_2$ at 0° C. under argon. Stirring was continued for 1 h at 0° C. and 1 h at room temperature. The solution was concentrated in vacuo. The residue was taken up in 20 mL MeCN/H$_2$O/AcOH (8:1:1), stirred for 45 min and concentrated in vacuo. Toluene (5 mL) was added and evaporated twice. On addition of Et$_2$O solids separated, which were collected by filtration and washed with the same solvent to give 1.5 g of 5b2 as a white powder (85%), which was used without purification. $^1$H NMR (DMSO-d$_6$, 300 MHz) δ 2.6 (s, 3H), 6.53 (s, 3H), 7.53 (d, J=10.2 Hz, 2H), 7.61 (d, J=8.1 Hz, 2H), 7.80 (d, J=8.1 Hz, 2H), 8.32 (d, J=10.2 Hz, 2H). $^{19}$F NMR (DMSO-d$_6$, 282.0 MHz) δ –1108.4 (d, J=104.3 Hz, 2F).

Synthesis of p-Nitrophenyl (2E)-3-[4-[[bis[(2,2-dimethyl-1-oxopropoxy)methoxy]phosphinyl]difluoromethyl]phenyl]-but-2-enoate (6b2, R$_1$=pivaloyloxymethyl): NaOH (174 mg, 4.3 mmol) in 2 mL of water was added dropwise to a stirred suspension of 5b2 (1.0 g, 2.4 mmol) in 5 mL of water. When the mixture became clear (pH~9), AgNO$_3$ (910 mg, 5.32 mmol) was added. After 2 h at 4° C. the gray precipitate was collected by filtration, dried, and pulverized in a mortar and pestle. The powder was suspended in dry toluene (10 mL) and pivaloyloxymethyl iodide (1.8 g, 7.2 mmol) was added and stirred for 48 h at room temperature. After filtration the solvent was removed in vacuo and the crude product was purified by silica gel column chromatography eluting with 30% EtOAc-hexanes to give 6b2 (0.9 g, 58%) as an oil. $^1$H NMR (CDCl$_3$, 300 MHz) δ 1.24 (s, 18H), 2.66 (s, 3H), 5.66-5.8 (m, 4H), 6.38 (s, 1H), 7.36 (d, J=–7.72 (m, 4H). $^{19}$F NMR (CDCl$_3$, 282.0 MHz) δ –108.8 (d, J=112.8 Hz, 2F). Anal. Calcd for C$_{29}$H$_{34}$F$_2$NO$_{11}$P: C, 54.29; H, 5.34; F, 5.92; N, 2.18; O, 27.43; P, 4.83: Found C, 54.00; H, 5.47; F, 6.10; N, 2.20.

Synthesis of 4-(diethoxyphosphinyl)oxyacetophenone (8b): To an ice cold stirred solution of 4-hydroxyacetophenone (2.0 g, 14.7 mmol) and TEA (4.1 mL, 29.4 mmol) in 30 mL of CH$_2$Cl$_2$, diethylchlorophosphate (2.5 mL, 17.6 mmol) was added dropwise, under inert atmosphere. The mixture was stirred for overnight and was quenched by the addition of d 5% HCl solution (30 mL). The layers were separated and the aqueous phase was extracted with CH$_2$Cl$_2$ (2×30 mL). The combined organic layers were washed with brine and dried over MgSO$_4$. The solvent was removed under vacuum and the crude product was purified by silica gel column chromatography eluting with EtOAc-hexanes. Yield 3.6 gm (90%). $^1$H NMR (CDCl$_3$, 300 MHz) δ1.31-1.38 (m, 6H), 2.58 (s, 3H), 4.17-4.28 (m, 4H), 7.31 (d, J=8.7 Hz, 2H), 7.97 (d, J=8.7 Hz, 2H).

Synthesis of tert-butyl (E)-3-[4-[(diethoxyphosphinyl)oxy]phenyl]-but-2-enoate (9b): nBuLi in hexane (4.0 mL of 2.5 M, 9.5 mmol) was added carefully to dry $^t$BuOH (10 mL) via a syringe under argon atmosphere. After 30min, a solution of tent-butyl diethylphosphonoacetate (2.00 g, 8 mmol) in 10 mL of dry $^t$BuOH was added at room temperature and the solution was stirred for 1.0 h. A solution of 103 (2 g, 7.4 mmol) in 5 ml $^t$BuOH was added to the mixture and stirred overnight at room temperature. The reaction was quenched with 30 mL of saturated NH$_4$Cl (aq) and extracted with ether (4×40 mL). The combined organic layers were washed with water (2×20 mL), brine (1×30 mL) and dried over MgSO$_4$. The solvent was removed and the crude product was purified by silica gel column chromatography, eluting with 20% ethylacetate-hexane, yielding 2.0 g (74%) of 9b. $^1$H NMR (CDCl$_3$, 300 MHz) δ1.32-1.37 (m, 6H), 1.51 (s, 9H), 2.50 (s, 3H), 4.16-4.27 (m, 4H), 6.0 (s, 1H), 7.2 (d, J=8.7 Hz, 2H), 7.43(d, J=8.7 Hz, 2H). $^{13}$C NMR (CDCl$_3$, 75.0 MHz) δ 16.0, 16.1, 17.6, 26.2, 28.3, 64.7, 64.83, 80.1, 115.3, 119.1, 119.8, 127.7, 130.7, 139.3, 151.0, 152.7, 161.8, 166.3, 196.9. Anal. Calcd for C$_{18}$H$_{27}$O$_6$P: C, 58.37; H, 7.35; O, 25.92; P, 8.36: Found C, 58.62; H, 7.33.

Synthesis of (2E)-3-[4-[(diethoxyphosphinyl)oxy]phenyl]-but-2-enoic acid (10b): Compound 9b (1.0 g) was treated with 10 mL of TFA: CH$_2$Cl$_2$ (95:5) for 1.0 h. The solvents were removed in vacuo, and residual TFA was removed by the addition and evaporation of toluene (3×5 mL). Compound 10b was used without further purification. $^1$H NMR (CDCl$_3$, 300 MHz) δ 1.34-1.39 (m, 6H), 2.51 (s, 3H), 6.13 (s, 1H), 7.22 (d, J=8.7 Hz, 2H), 7.47 (d, J=8.7 Hz, 2H).

Synthesis of pentachlorophenyl (2E)-3-[4-[(diethoxyphosphinyl)oxy]phenyl]-but-2-enoate (11b1): A solution of 10b (2.0 g, 6.4 mmol), pentachlorophenol (1.9 g, 7.0 mmol), DCC (1.6 g, 7.7 mmol) and DMAP (0.08 g, 0.64 mmol) in 100 mL of EtOAc was stirred at room temperature for 24 h. The mixture was filtered through celite and the solvent removed in vacuo. The crude product was purified by silica gel chromatography eluting with 25% EtOac-hexanes to give 2.6 g (72%) of 11b1 as white solid. $^1$H NMR (CDCl$_3$, 300 MHz) δ 1.26-1.32 (m, 6H), 2.54 (d, J=1.2 Hz, 3H), 4.12-4.21 (m, 4H), 6.34 (d, J=1.2 Hz, 1H), 7.2 (d, J=8.7 Hz, 2H), 7.49 (d, J=8.7 Hz, 2H). $^{11}$C NMR (CDCl$_3$, 75.0 MHz) δ 16.0, 16.1, 18.4, 64.8, 64.8, 68.9, 113.4, 120.2, 120.3, 128.0, 128.1, 131.2, 131.9, 137.8, 141.9, 144.3, 152.1, 160.6, 161.9. HRMS (M+H) calc, 560.9362; found, 560.9197.

Synthesis of pentachlorophenyl (2E)-3-[4-(phosphinyloxy)phenyl]-but-2-enoate (12b1): Iodotrimethylsilane (2.0 mL, 14.2 mmol) in 5 mL of dry CH$_2$Cl$_2$ was added dropwise to a solution of 11b1 (2.0 g, 3.55 mmol) and bis(trimethylsilyl)trifluoroacetamide (1.8 mL, 7.1 mmol) in 20 mL of dry CH$_2$Cl$_2$ at 0° C. under argon. Stirring was continued for 1 h at 0° C. and 1 h at room temperature. The solution was concentrated in vacuo. The residue was treated with 20 mL of MeCN/H$_2$O (9:1) and 5 drops of conc. HCl for 30 min and concentrated in vacuo. Toluene (5 mL) was added and evaporated twice. On addition of Et$_2$O solids separated, which were collected by filtration and washed with the same solvent to give, after drying over P$_2$O$_5$ in vacuo, 1.6 g of 12b as a white powder (88%). It was used without further purification. $^1$H NMR (DMSO-d$_6$, 300 MHz) δ 2.6 (s, 3H), 6.6 (s, 1H), 7.24 (d, J=8.7 Hz, 2H), 7.75 (d, J=8.7 Hz, 2H). HRMS (M+H) calc, 503.8658; found, 503.8691.

Synthesis of pentachlorophenyl (2E)-3-[4-[[bis[(2,2-dimethyl-1-oxopropoxy)methoxy]phosphinyl]oxy]phenyl]-but-2-enoate: (13b1 R$_1$=pivaloyloxymethyl) To a stirred suspension of 12b1 (1.0 g, 1.97 mmol) in 10 mL of water, NaOH (158 mg, 3.94 mmol) in 2 mL of water was added. The mixture became clear (pH-9). A 5 mL aqueous solution of AgNO$_3$ (807 mg, 4.75 mmol), was added. After 3 h of stirring at room temperature, the gray precipitate was collected by filtration, dried over P$_2$O$_5$, and pulverized in a mortar and pestle. The powder was suspended in dry toluene (15 mL) and pivaloyloxymethyl iodide (1.4 g, 5.7 mmol) was added and the mixture was stirred for 48 h at room temperature. After filtration the solvent was removed in vacuo and the crude product was purified by silica gel column chromatography eluting with 30% EtOAc-hexanes to give colorless sticky liquid (1.0 g, 69%). $^1$H NMR (CDCl$_3$, 500 MHz) δ 1.22 (s, 18H), 2.64 (s, 3H), 5.73-5.8 (m, 4H), 6.43 (s, 1H), 7.31 (d, J=8.0 Hz, 2H), 7.58 (d, J=8.0 Hz, 2H). $^{13}$C NMR (CDCl$_3$, 125 MHz) δ 18.5, 26.8, 38.7, 83.1, 113.8, 120.4, 127.9, 128.2, 131.3, 132.0, 138.6, 144.3, 151.3, 160.4, 161.9, 176.6. HRMS (M+H) calc, 733.0097; found, 733.0122

Synthesis of p-nitrophenyl (2E)-3-[4-[(diphenoxyphosphinyl)difluoromethy]phenyl]-but-2-enoate (6b2 R$_1$=C$_6$H$_5$): To a stirred solution of 5b2 (1.0 g, 2.42 mmol) in 15 ml of dry toluene was added thionyl chloride (0.9 mL, 12.1 mmol) drop wise. It was then heated to 60° C. for 2 h, with a reflux condenser, under dry nitrogen. The solvent was removed under vacuum and the residue was diluted with 20 mL of dry CH$_2$Cl$_2$ and treated with phenol (6.05 mmol, 0.57 g), and triethylamine (7.26 mmol, 1.0 mL) at 0° C. for 2 h at room temperatire. The solvent was removed and the crude product was purified by silica gel chromatography eluting with 30% EtOAc-Hexanes. Yield 0.58 g (43%).$^1$H NMR (CDCl$_3$, 300 MHz) δ 2.58 (s, 3H), 6.3 (s, 1H), 7.05 (d, J=7.2 Hz, 2H), 7.11-7.3 (m, 10H), 7.55 (d, J=7.8 Hz, 2H), 8.23 (d, J=7.2 Hz, 2H). HRMS (M+H) calc, 566.1180; found, 566.1205.

Synthesis of chloromethyl 4-fluorobenzoate: (Mudryk, B. et al., Tetrahedron Lett. 2002, 43, 6317-6318) 4-Fluorobenzoyl chloride (3.0 g, 18.9 mmol) was added to a stirred suspension of zirconium tetrachloride (4.0 g, 17.01 mmol) in dry CH$_2$Cl$_2$ (40 mL) at room temperature. After 15 min, the reaction mixture was cooled to 0° C. and paraformaldehyde (0.68 g, 22.7 mmol) was added. The slurry was stirred at 0-25° C. for 2 h and the solvent was removed under vacuum. Water (50 mL) was added slowly and the mixture was agitated for 10 min. The aqueous layer was extracted with EtOAc (3×50 mL). The combined organic phase was washed with 1 N sodium bicarbonate (2×50 mL) followed by brine (1×30 mL). The solvent was removed and the product was purified by silica gel chromatography (5% EtOAc-Hexanes). Yield 3.2 g (89%). $^1$H NMR (500 MHz, CDCl$_3$): δ 5.86 (s, 2H), 7.06 (m, 2H), 8.02 (m, 2H).

Synthesis of iodomethyl 4-fluorobenzoate: To a solution of chloromethyl 4-fluorobenzoate (3.0g, 15.9 mmol) in 50 mL of dry acetone, NaI (4.8 g, 31.8 mmol) was added and the mixture was stirred overnight. The solvent was removed and Et$_2$O (150 mL) was added to the solid residues and the mixture was stirred for 10 min. After filtration the filtrate was washed with 5% NaHSO$_3$ (aq) (2×25 mL) followed by brine. The organic solution was concentrated by rotary evaporation and purified by silica gel chromatography to give a light yellow oil. Yield 3.7 g (85%). $^1$H NMR (300 MHz, CDCl$_3$): δ 6.16 (s, 2H), 7.17 (m, 2H), 8.08 (m, 2H).

Synthesis of iodomethyl benzoate: From commercially available chloromethyl benzoate. Yield 4.2 (91%). $^1$H NMR (300 MHz, CDCl$_3$): δ 6.17 (s, 2H), 7.47 (m, 2H), 7.62 (m, 1H) 8.06 (m, 2H).

Synthesis of pentachlorophenyl (E)-3-[4-[bis(4-fluorobenzoyloxymethoxyphosphinyl)difluoromethyl]phenyl]-but-2-enoate (6b1 R$_1$=4-Fluorobenzoyloxymethyl) NaOH (80 mg, 2.0 mmol) in 2 mL of H$_2$O was added dropwise to a stirred suspension of pentachlorophenyl (E)-3-(4-phosphonyldifluoromethyphenyl) but-2-enoate (500 mg, 0.92 mmol) in 5 mL of H$_2$O. When the mixture became clear (pH~9), AgNO$_3$ (510 mg, 3.0 mmol) was added. After 2 h at 4° C. the gray precipitate was collected by filtration, dried over P$_2$O$_5$ in vacuo, and pulverized in a mortar and pestle. The powder (400 mg) was suspended in dry toluene (10 mL) and iodomethyl 4-fluorobenzoate (290 mg, 1.03 mmol) was added and stirred for 48 h at room temperature. After filtration the solvent was removed in vacuo and the crude product was purified by silica gel column chromatography eluting with 30% EtOAc-hexanes to give colorless oil. Yield 290 mg, (61%). $^1$H NMR (300 MHz, CDCl$_3$): δ 2.49 (s, 3H), 5.87 (m, 4H), 6.3 (s, 1H), 7.01 (m, 4H), 7.45 (d, J=8.4 Hz, 2H), 7.54 (d, J=8.4 Hz, 2H), 7.94 (m, 4H). $^{13}$C NMR (75 MHz, CDCl$_3$): δ 18.3, 82.5, 82.8, 115.0, 115.7, 116.1, 124.5, 126.7, 127.9, 131.4, 132.0, 132.7, 132.9, 144.2, 161.6, 163.6, 164.7, 168.1. HRMS (M+H) calc, 844.9272; found, 844.9278.

Synthesis of Pentachlorophenyl (2E)-3-[4-[(bis-benzoyloxymethoxyphosphinyl)difluoromethyl]phenyl]but-2-enoate (6b1 R$_1$=benzoyloxymethyl): the procedure for (6b1 R$_1$=4-Fluorobenzoyloxymethyl) was used. Yield: 65%. $^1$H NMR (300 MHz, CDCl$_3$): δ 2.46 (s, 3H), 5.91 (m, 4H), 6.26 (s, 1H), 7.17-7.41 (m, 6H), 7.49-7.55 (m, 4H), 7.91-7.94 (m, 4H). $^{13}$C NMR (75 MHz, CDCl$_3$): δ 18.3, 82.5, 82.8, 114.9, 126.7, 126.8, 127.9, 128.3, 128.6, 130.1, 131.4, 132.0, 134.1, 141.9, 143.7, 144.2, 160.1, 161.7, 164.6, 168. $^1$HRMS (M+H) calc, 808.9461; found, 808.9468.

Synthesis of Pentachlorophenyl (2E)-3-[4 [[phthaloylbis(oxymethoxy)]phosphinyl]difluoromethyl]phenyl]-but-2-enoate: The procedure for (6b1 $R_1$=4-Fluorobenzoyloxymethyl) was used. Yield: 42%. $^1$HRMS (M+NH$_4$) calc, 747.9257; found, 747.9261.

Synthesis of pentachlorophenyl (2E)-3-[4-[[bis[(piperonyloxy)methoxy]phosphinyl]difluoromethyl]phenyl]-but-2-enoate (6b1 $R_1$=4-Fluorobenzoyloxymethyl): The procedure for (6b1 $R_1$=4-Fluorobenzoyloxymethyl) was used. Yield: 63%. $^1$HRMS (M+NH$_4$) calc, 913.9523; found, 913.9999.

Synthesis of pentachlorophenyl (2E)-3-[4-[[bis[2-methylbenzoyloxy)methoxy]phosphinyl]difluoromethyl]phenyl]-but-2-enoate (6b1 $R_1$=4-Fluorobenzoyloxymethyl): The procedure for (6b1 $R_1$=4-Fluorobenzoyloxymethyl) was used. Yield: 68%. $^1$HRMS (M+NH$_4$) calc, 854.0069; found, 853.9949.

Synthesis of pentachlorophenyl (2E)-3-[4-[[bis[(2-chlorobenzoyloxy)methoxy]phosphinyl]difluoromethyl]phenyl]-but-2-enoate (6b1 $R_1$=4-Fluorobenzoyloxymethyl): The procedure for (6b1 $R_1$=4-Fluorobenzoyloxymethyl) was used. Yield: 64%. $^1$HRMS (M+NH$_4$) calc, 893.8947; found, 893.8927.

Synthesis of 4-Nitrophenyl 2-[(9H-fluoren-9-ylmethoxy)carbonyl]aminoethyl carbonate: (From Mandal et al, *J. Med. Chem.* 2009, 52, 6126-41)) 4-Nitrophenyl chloroformate (1.6 g, 7.8 mmol) in 10 mL of dry CH$_2$Cl$_2$ was added drop wise to a stirred solution of Fmoc-aminoethanol (2.0 g, 7.06 mmol) and pyridine (0.9 mL, 10.6 mmol) in 20 mL of dry CH$_2$Cl$_2$ at 0° C. under an atmosphere of argon. Upon completion (TLC), the solution was transferred to a separatory funnel with an additional 20 mL of CH$_2$Cl$_2$. The organic solution was washed with 10% HCl (3×30 mL), 10% Na$_2$CO$_3$ (3×30 mL), and brine (50 mL) and was dried (MgSO$_4$). The crude mixture was purified by silica gel chromatography eluting with 40% EtOAc-hexane to give 2.6 g (82%) of desired product as a white solid. $^1$H NMR (300 MHz, CDCl$_3$) δ 3.6 (m, 2H), 4.25-4.48 (m, 5H), 5.2 (m, 1H), 7.28-7.45 (m, 6H), 7.6 (d, J=7.2 Hz, 2H), 7.8 (d, J=7.5 Hz, 2H), 8.28 (d, J=8.4 Hz, 2H). $^{13}$C NMR (75 MHz, CDCl$_3$) δ 39.9, 47.2, 66.9, 68.2, 120.0, 121.6, 121.7, 124.9, 125.3, 125.5, 127.0, 127.7, 141.4, 143.8, 145.5, 152.4, 155.4. Anal. Calcd for C$_{24}$H$_{20}$N$_2$O$_7$: C, 64.28; H, 4.50; N, 6.25; O, 24.98; Found C, 63.91; H, 4.42; N, 6.36. HRMS (M+H) Calc'd: 454.2230; Found 454.2240.

Synthesis of Fmoc-D-threoninol benzyl ether (From Mandal et al, *J. Med. Chem.* 2009, 52, 6126-41) A solution of Fmoc-D-Thr(OBzl) (5.0 mmol), DCC (6.0 mmol) and 2-mercaptopyridine (5.5 mmol) in 100 mL of EtOAc was stirred for 3 h. The white precipitate was filtered off and the filtrate was concentrated under vacuum. It was then diluted with 50 mL of THF and the solution was added slowly to a suspension of NaBH$_4$ (10.0 mmol) in 20 mL of THF and 10 mL of water at 0° C. After 30 min, the reaction was quenched by slow addition of ice-cold 5% HCl (aq) (50 mL) and extracted with ether (3×150 mL). The combined organic layers were washed with aqueous 10% NaHCO$_3$ (3×40 mL), water (2×50 mL), and brine (1×40 mL). After drying (Na$_2$SO$_4$) and concentration under vacuum the crude residue was purified either by recrystallization from hexane-ether or silica gel column chromatography. Yield: 1.74 g (81%). $^1$H NMR (CDCl$_3$, 300 MHz) δ 1.22 (d, J=7.2 Hz, 3H), 2.65 (m, 1H), 3.7 (m, 2H), 3.83 (m, 1H), 4.2 (t, J=6.6 Hz, 1H), 4.35-4.45 (m, 3H), 4.61 (d, J=11.4, 1H), 5.32 (m, 1H), 7.28-7.4 (m, 9H), 7.58 (d, J=7.2 Hz, 2H), 7.73 (d, J=7.2 Hz, 2H). $^{13}$C NMR (CDCl$_3$, 75 MHz) δ 16.2, 47.3, 56.7, 63.9, 66.9, 70.9, 74.4, 120.0, 125.1, 127.1, 127.7, 127.9, 128.0, 128.6, 138.0, 141.4, 144.0. HRMS (M+H) Calc'd: 418.2018; Found: 418.1696.

Synthesis of benzyl (4S, 5S)-5-benzyloxy-4-[[(9H-fluoren-9-ylmethoxy)carbonyl]amino]-(E)-2-hexenoate. (From Mandal et al, *J. Med. Chem.* 2009, 52, 6126-41) To a solution of oxalyl chloride (8.0 mmol) in 30 mL of dry CH$_2$Cl$_2$, stirred at –78° C. under argon was added DMSO (16.0 mmol) via syringe dropwise with vigorous stirring. After 20 min, a solution of Fmoc-D-threoninol benzyl ether (5.0 mmol) in 20 mL of dry CH$_2$Cl$_2$, was added while maintaining the bath temperature at –78° C. Stirring was continued further for 30 min. Dry and distilled DIEA (30 mmol) was then added using a syringe and the reaction mixture then allowed to warm to room temperature without removing bath. The reaction mixture then quenched with 20 mL of ice-cold water and extracted with CH$_2$Cl$_2$ (3×80 mL). The combined organic layers were washed with 1N HCl (3×30 mL), brine (1×30 mL) and dried (MgSO$_4$) and concentrated under vacuum. The crude aldehyde was used immediately for the next step without characterization. A mixture of the Fmoc-amino aldehyde (4.0 mmol) and benzyl (triphenylphosphoranylidene)-acetate (4.4 mmol) in dry CH$_2$Cl$_2$ (20 mL) was stirred for 3 h. The progress of the reaction was monitored by thin layer chromatography. After completion the solvent was removed in vacuo and the residue was purified by silica gel chromatography using EtOAc in hexane. Yield: 1.55 g (68%), white powder. $^1$H NMR (CDCl$_3$, 300 MHz) δ 1.22 (d, J=5.7 Hz, 3H), 3.7 (m, 1H), 4.2 (t, J=6.6 Hz, 1H), 4.3-4.45 (m, 4H), 4.58 (d, J=11.7 Hz, 1H), 5.2 (s, 2H), 5.98 (d, J=15.3 Hz, 1H), 6.98 (m, 1H), 7.28-7.38 (m, 14H), 7.58 (d, J=7.5 Hz, 2H), 7.74 (d, J=7.5 Hz, 2H). $^{13}$C NMR (CDCl$_3$, 75 MHz) δ 16.5, 47.3, 66.3, 66.9, 71.1, 75.1, 120.0, 121.7, 125.0, 127.0, 127.7, 127.8, 127.9, 128.3, 128.5, 128.6, 135.9, 137.7, 141.3, 143.8, 143.9, 147.2, 165.8. Anal (C$_{35}$H$_{33}$NO$_5$) C, H, N: Calc'd: C, 76.76; H, 6.07; N, 2.56. Found: C, 76.61; H, 6.06; N, 2.55. HRMS (M+H) Calc'd: 548.2437. Found: 548.2451.

Synthesis of (4S, 5S)-5-benzyloxy-4-[[(9H-fluoren-9-ylmethoxy)carbonyl]amino]-2-hexanoic acid: (From Mandal et al, *J. Med. Chem.* 2009, 52, 6126-41) To a stirred suspension of benzyl (4S, 5S)-5-benzyloxy-4-[[(9H-fluoren-9-ylmethoxy)carbonyl]amino]-(E)-2-hexenoate (2.0 mmol) and 10% Pd—C (10% by wt) in 15 mL of methanol-THF (4:1 v/v), was added triethylsilane (20.0 mmol) dropwise under argon atmosphere. The reaction started with evolution of hydrogen gas. After completion of reaction (TLC), the mixture was filtered through celite and the solvent was removed in vacuo. The crude product was purified either by triturating with ether-hexane or by short silica gel column chromatography, eluting with 2% hexane-EtOAc, followed by hexane-EtOAc-MeOH (3:6:1 v/v/v). Yield: 0.75 g (82%). White powder. $^1$H NMR (DMSO-d$_6$, 500 MHz) δ 1.07 (d, J=6.9 Hz, 3H), 1.63 (m, 1H), 1.8 (m, 1H), 2.2-2.3 (m, 2H), 3.53 (m, 1H), 3.62 (m, 1H), 4.22 (m, 1H), 4.26-4.31 (m, 3H), 4.5 (m, 2H), 7.2 (d, J=5.4 Hz, 1H), 7.27-7.43 (m, 9 H), 7.72 (d, J=7.5 Hz, 2H), 7.9 (d, J=7.5 Hz, 2H), 12.04 (s, 1H). $^{13}$C NMR (DMSO-d$_6$, 125 MHz) δ 15.6, 24.9, 31.0, 47.3, 53.9, 65.7, 70.4, 76.3, 120.6, 125.7, 127.5, 127.7, 127.8, 128.1, 128.6, 129.2, 139.4, 141.2, 144.4, 156.7, 174.8. Anal (C$_{28}$H$_{29}$NO$_5$) C, H, N: Calc'd: C, 73.18; H, 6.36; N, 3.05. Found: C, 72.52; H, 6.38; N, 3.01. HRMS (M+H) Calc'd: 460.2124; Found: 460.2141.

Preparation of 4(S)-[(9-fluorenylmethoxycarbonyl) amino]-2-pentenoic acid benzyl ester: (Mandal, P. K.; McMurray, J. S. *Pd—C Induced Catalytic Transfer Hydrogenation with Triethylsilane.* J. Org. Chem. 72, 6599-660 (2007)): A solution of Fmoc-Alaninal (1 g, 3.4 mmol) and benzyl (triphenylphosphoranylidene)acetate (1.5 g, 3.75 mmol) in 15 mL of dry CH$_2$Cl$_2$ was stirred for 4 h. The solvent was removed in vacuo and the crude product was purified by silica gel chromatography, eluting with 15% EtOAc-hexane.

Yield 1.4 g (95%). ¹H NMR (CDCl₃) δ 1.28 (d, J=6.6 Hz, 3H), 4.2 (t, J=6.6 Hz, 1H), 4.3-4.4 (m, 3H), 4.71 (d, J=8.7 Hz, 1H), 5.93 (d, J=15.9 Hz, 1H), 6.91 (dd, J=3.9, 15.6 Hz, 1H), 7.25-7.4 (m, 9H), 7.57 (d, J=7.2 Hz, 2H), 7.75 (d, J=7.2 Hz, 2H). HRMS (M+H) calcd. for $C_{27}H_{26}NO_4$: 428.1862; found 428.1862.

Preparation of 4(S)-N-(9-fluorenylmethoxycarbonyl)-4-methyl-4-aminobutyric acid ((Mandal, P. K.; McMurray, J. S. *Pd—C induced Catalytic Transfer Hydrogenation with Triethylsilane.* J. Org. Chem. 72, 6599-660 (2007)):: To a stirred solution of 4(S)-[(9-fluorenylmethoxycarbonyl)amino]-2-pentenoic acid benzyl ester (1 mmol) and 10% Pd—C (10-20% by weight) in MeOH (2-3 mL), neat TES (10 mmol) was added dropwise from a pressure equalizing dropping funnel under an argon filled balloon. When the reaction was complete (TLC), the mixture was filtered through celite and the solvent was removed in vacuo. The product was chromatographically purified on a short silica gel column eluting with EtOAc_hexanes to give the product in 88% yield as a white powder. ¹H NMR (DMSO-d₆) δ 1.24 (d, J=6.6 Hz, 2H), 1.62 (m, 2H), 2.2 (m, 2H), 3.51 (m, 1H), 4.18-4.35 (m, 3H), 7.15 (d, J=6.6 Hz, 1H), 7.3-7.43 (m, 4H), 7.69 (d, J=7.2 Hz, 2H), 7.88 (d, J=7.2 Hz, 2H), HRMS (M+H) calcd. for $C_{20}H_{22}NO_4$: 340.1549; found 340.1556.

For the compound of Example 1. Synthesis of (2E)-3-[4-[[bis[(2,2-dimethyl-1-oxopropoxy)methoxy]phosphinyl]difluoromethyl]phenyl]-but-2-enoyl-Haic-(R)-4-aminopentamide Method A Rink resin (0.3 g, 0.225 mmol) was swollen in DMF/CH₂Cl₂ (1:1) and was washed with 2×5 mL of the same solvent. The Fmoc group was removed by treatment with 20% piperidine in DMF for 3 min (repeated 3 times). For coupling of the next two amino acids, Fmoc-(R)-4-aminopentanoic acid and Fmoc-Haic-OH, three-fold excesses of the Fmoc-amino acids, PyBop, and HOBt were used along with six-fold excesses of DIPEA in 4 mL of DMF/CH₂Cl₂. After assembly of the amino acid chain, the Fmoc group was removed by treatment with 20% piperidine in DMF and the resins were washed with 3×10 mL of DMF/CH₂Cl₂ (1:1). Cleavage was accomplished with three treatments of the resins with 5 mL of TFA:TIS:H₂O (95:2.5:2.5) for 10 min each. The solvents were removed in vacuo and residual acid was removed by addition and evaporation of toluene (3×5 mL). Et₂O was added and the precipitate was collected by centrifugation. The crude product was purified by reverse phase HPLC using a gradient of ACN in H₂O. Pure H-Haic-NHCH(CH₃)CH₂CH₂CONH₂ (100 mg, 0.29 mmol), 6b2 (0.223 g, 0.29 mmol), dry and distilled DIPEA (0.1 mL, 0.58 mmol) and HOBt (0.045 g, 0.29 mmol) in 4 mL of dry N-methylpyrrolidone and CH₂Cl₂ (1:1) were mixed together and stirred for two h. The reaction was monitored by HPLC. After completion, the solvent was removed and the crude product was purified by reverse phase HPLC using a gradient of ACN in H₂O to yield 27 mg of the compound of Example 1.

Method B. To a stirred solution of TFA.H-Haic-NHCH(CH₃)CH₂CH₂CONH₂ (0.050 g, 0.11 mmol), N-methylmorpholine (0.036 mL, 0.33 mmol) and DMAP (0.005 g, 0.033 mmol) in 3 mL of dry NMP, was added a solution of 6b1 (0.085 g, 0.11 mmol) in 2 mL of dry MeCN under inert atmosphere. The reaction was monitored by HPLC. After completion, about 1 h, the reaction mixture was concentrated under vacuum then purified by reverse phase HPLC using MeCN-water system. Yield: 0.70 g (76%) of the compound of Example 1. HRMS (M+H) calcd 847.3495, found 847.3489.

For Example 8: Synthesis of (E)-3-[4-[(Diphenoxyphosphinyl)difluoromethyl]phenyl]-but-2-enoyl-Haic-(R)-4-aminopentamide Rink resin (0.2 g, 0.15 mmol) was swollen in 10 mL of DMF/DCM (1:1) and was washed with 3×5 mL of the same solvent. The Fmoc group was removed by treatment with 20% piperidine in DMF (3×10 mL) for 5 min. For coupling of the next two amino acids, Fmoc-4-amino-4-methyl butyric acid and Fmoc-Haic-OH, three-fold excesses of the Fmoc-amino acids, PyBop, HOBt, and DIPEA in 10 mL of DMF/DCM. After assembly of the amino acid chain, the Fmoc group was removed by treatment with 20% piperidine in DMF and the resins were washed with DMF/DCM (1:1) (3×10 mL). The final coupling was carried out with two-fold excess of p-nitrophenyl (2E)-3-[4-[(diphenoxyphosphinyl)difluoromethyl]phenyl]-but-2-enoate along with two-fold excess of DIPEA, and HOBt in 10 mL of DMF/DCM. After coupling, resins were washed with with 3×10 mL of DMF/DCM, followed by DCM (3×10 mL). Resins were then treated with 10 mL of TFA:TIS:H₂O (95:2.5:2.5) (3 times) for 10 min each. The solvents were removed in vacuo and residual acid was removed by addition and evaporation of toluene (3×5 mL). Et₂O was added and the precipitate was collected by centrifugation. The crude product was purified by reverse phase HPLC using a gradient of ACN in H₂O to yield 48 mg of prodrug. HRMS (M+H) calc 771.2759; found 771.2736.

The invention is further illustrated by the following examples.

EXAMPLE 1

(2E)-3-[4-[[bis[(2,2-dimethyl-1-oxopropoxy)methoxy]phosphinyl]difluoromethyl]phenyl]-but-2-enoyl-Haic-(R)-4-aminopentamide

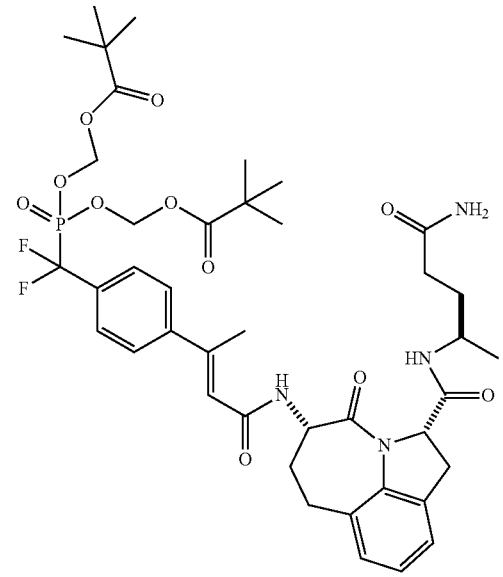

M + H (calc)  M + H (found)
847.3495      847.3489

¹H NMR (Acetonitrile-d₃ 500 MHz) δ 1.1 (d, J=6.5 Hz, 3H), 1.2 (s, 18H), 1.6-1.73 (m, 2H), 2.03-2.26 (m, 8H), 2.52 (s, 3H), 3.0-3.17 (m, 2H), 3.2-3.26 (m, 1H), 3.38 (m, 1H), 3.8 (m, 1H), 4.5 (m, 1H), 5.03 (m, 1H), 5.46 (s, 1H), 5.62-5.7 (m, 4H), 6.2 (s, 1H), 6.36 (s, 1H), 6.74 (d, J=8.0 Hz, 1H), 7.00 (m, 1H), 7.09-7.11 (m, 2H), 7.32 (d, J=6.5 Hz, 1H), 7.58 (d, J=8.0 Hz, 2H), 7.66 (d, J=8.0 Hz, 2H). ¹³C NMR (Acetonitrile-d₃ 125 MHz) δ 0.2, 0.3, 0.5, 0.6, 0.8, 16.4, 20.1, 26.0, 29.6, 31.1, 31.7, 31.9, 38.4, 44.9, 53.3, 61.45, 82.8, 121.5, 123.0, 124.2, 126.4, 126.6, 129.5, 133.2, 138.7, 145.6, 148.7, 165.5, 170.3, 170.4, 174.8, 176.4. HRMS (M+H) calc 847.3495 found 847.3489

EXAMPLE 2

(2E)-3-[4-[[bis[(2,2-dimethyl-1-oxopropoxy)methoxy]phosphinyl]difluoromethyl]phenyl]-but-2-enoyl-Haic-glutaminyl-benzylamide

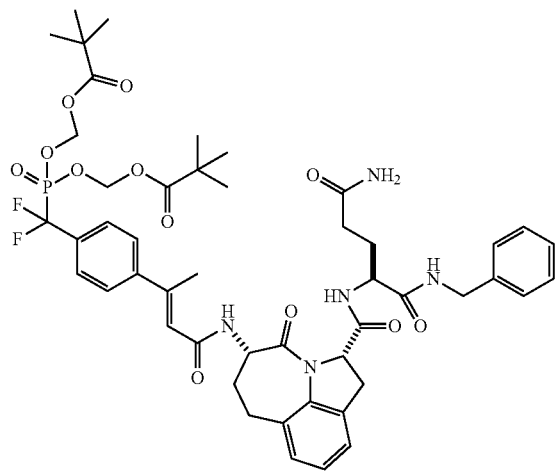

M + H (calc)   M + H (found)
966.3866        966.3875

EXAMPLE 3

(2E)-3-[4-[[bis[(2,2-dimethyl-1-oxopropoxy)methoxy]phosphinyl]difluoromethyl]phenyl]-but-2-enoyl-Haic-2-aminoethylcarbamate

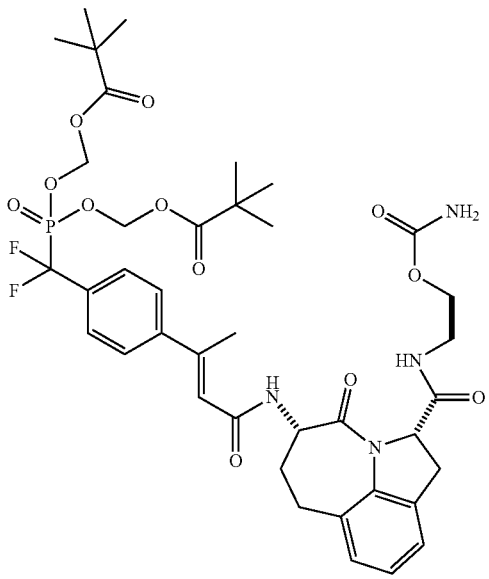

M + H (calc)   M + H (found)
835.3293        835.3258

EXAMPLE 4

(2E)-3-[4-[[bis[(2,2-dimethyl-1-oxopropoxy)methoxy]phosphinyl]difluoromethyl]phenyl]-but-2-enoyl-Haic-2-aminoethylurea

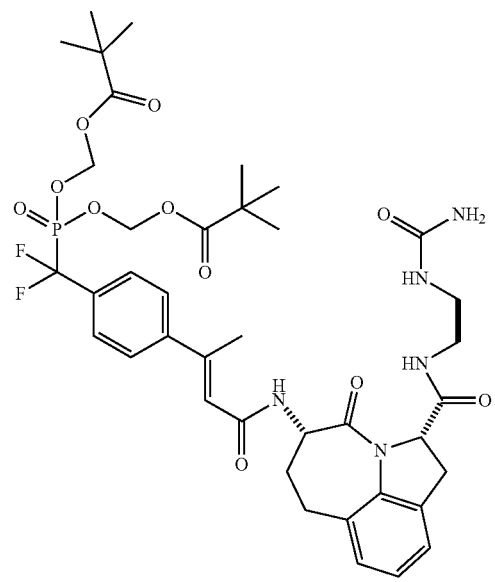

M + H (calc)   M + H (found)
834.3213        834.3321

EXAMPLE 5

(2E)-3-[4-[[bis[(2,2-dimethyl-1-oxopropoxy)methoxy]phosphinyl]difluoromethyl]phenyl]-propenoyl-Haic-(R)-4-aminopentamide

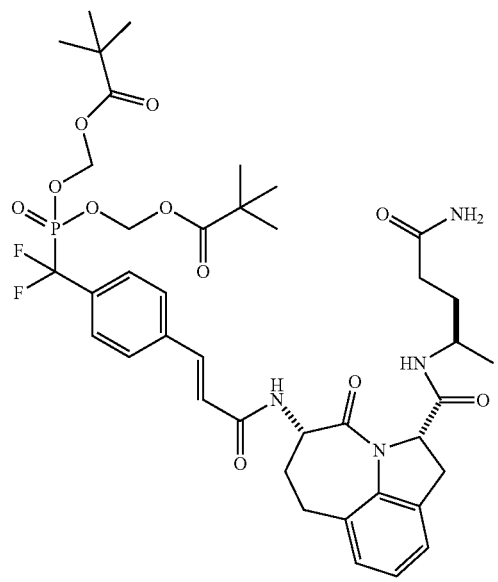

M + H (calc)   M + H (found)
833.3338        833.3366

EXAMPLE 6

(2E)-3-[4-[[bis[(2,2-dimethyl-1-oxopropoxy)methoxy]phosphinyl]oxy]phenyl]-but-2-enoyl-Haic-(R)-4-aminopentamide

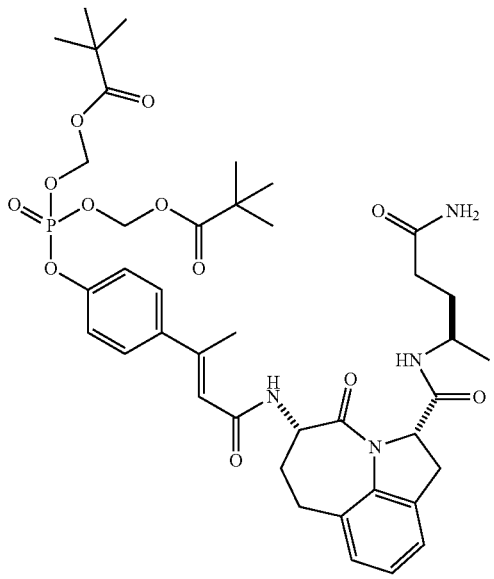

M + H (calc)   M + H (found)
813.3389         813.4000

EXAMPLE 7

(2E)-3-[4-[(Diethoxyphosphinyl)difluoromethyl]phenyl]-but-2-enoyl-Haic-(R)-4-aminopentamide

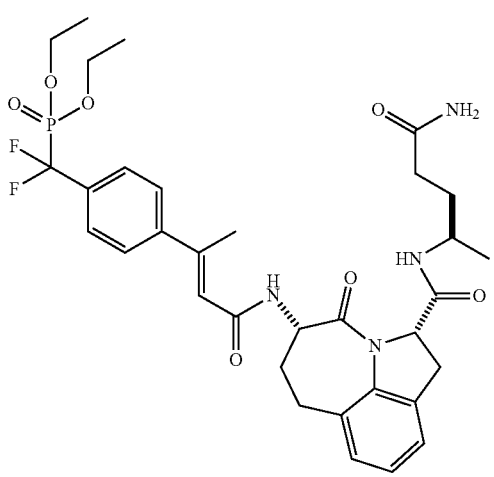

M + H (calc)   M + H (found)
675.2759         675.2768

EXAMPLE 8

(E)-3-[4-[(Diphenoxyphosphinyl)difluoromethyl]phenyl]-but-2-enoyl-Haic-(R)-4-aminopentamide

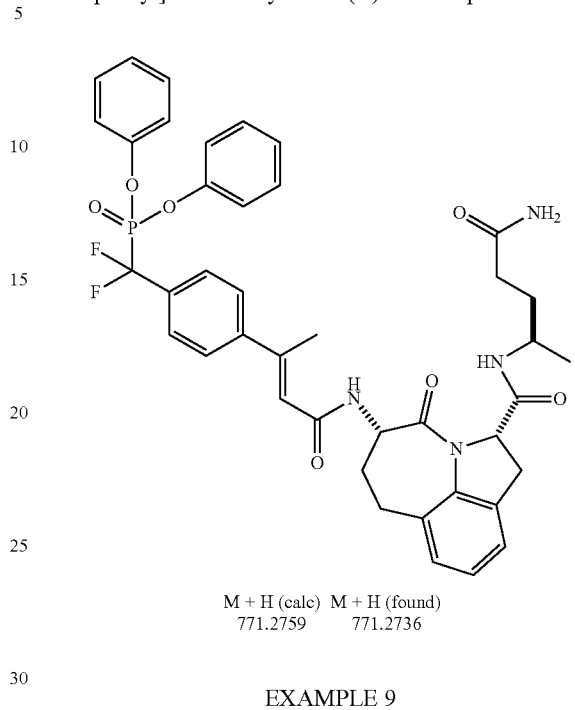

M + H (calc)   M + H (found)
771.2759         771.2736

EXAMPLE 9

(2E)-3-[4-[[Bis[(4-fluorobenzoyloxy)methoxy]phosphinyl]difluoromethyl]phenyl]-but-2-enoyl-Haic-(R)-4-aminopentamide

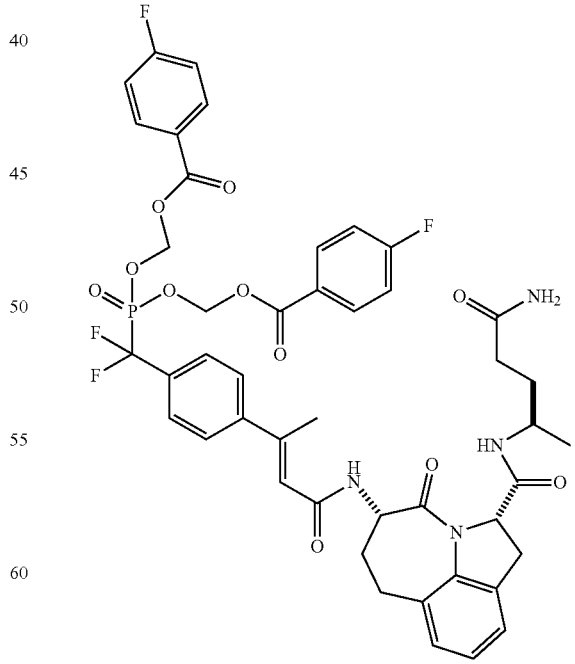

M + H (calc)   M + H (found)
923.2680         923.2711

EXAMPLE 10

(2E)-3-[4-[[Bis[(benzoyloxy)methoxy]phosphinyl]difluoromethyl]phenyl]-but-2-enoyl-Haic-(R)-4-aminopentamide

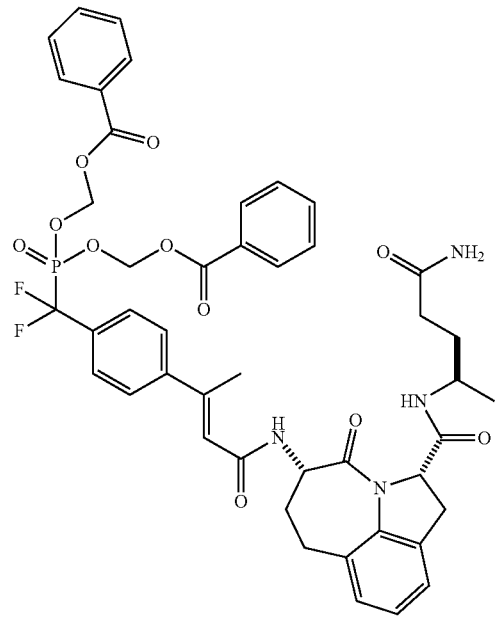

M + H (calc)   M + H (found)
887.2869       887.2901

EXAMPLE 11

(2E)-3-[4-[[phthaloylbis(oxymethoxy)]phosphinyl]difluoromethyl]phenyl]but-2-enoyl-Haic-(R)-4-aminopentamide

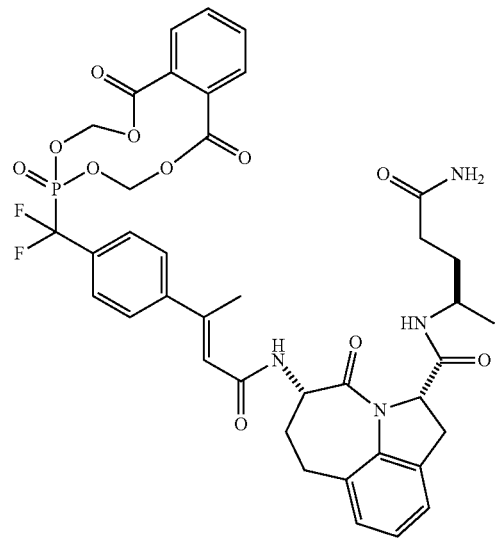

M + H (calc)   M + H (found)
809.2399       809.2427

EXAMPLE 12

(2E)-3-[4-[[Bis[(piperonyloxy)methoxy]phosphinyl]difluoromethyl]phenyl]-but-2-enoyl-Haic-(R)-4-aminopentamide

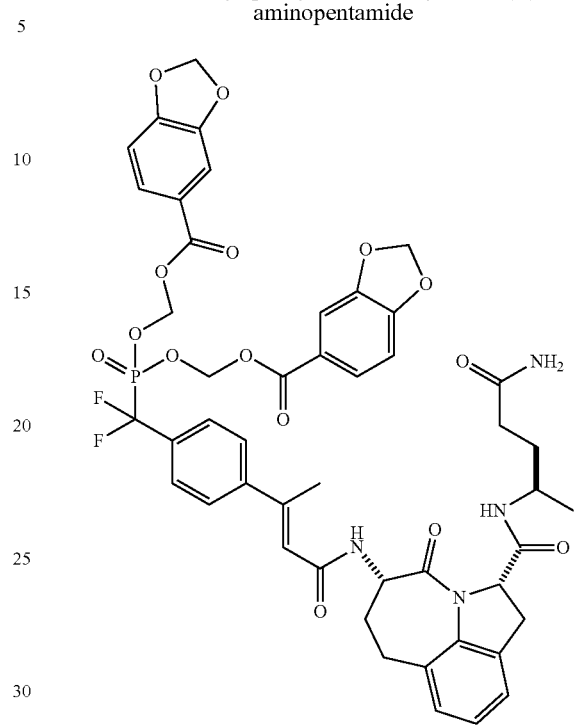

M + H (calc)   M + H (found)
975.2665       975.2706

EXAMPLE 13

(E)-3-[4-[[Bis[(2-methylbenzoyloxy)methoxy]phosphinyl]difluoromethyl]phenyl]-but-2-enoyl-Haic-(R)-4-aminopentamide

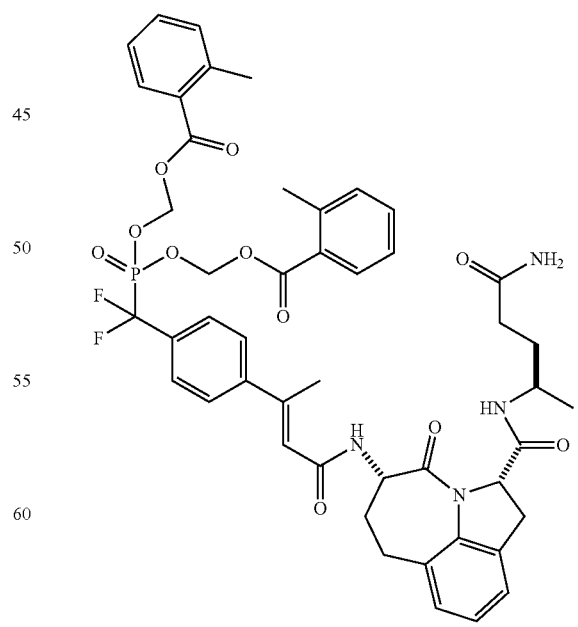

M + H (calc)   M + H (found)
915.3182       915.3204

EXAMPLE 14

(2E)-3-[4-[[Bis[(2-chlorobenzoyloxy)methoxy]phosphinyl]difluoromethyl]phenyl]-but-2-enoyl-Haic-(R)-4-aminopentamide

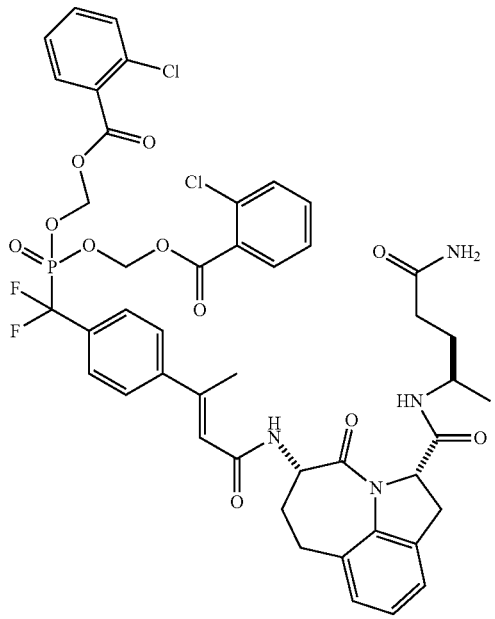

M + H (calc)   M + H (found)
955.2089        955.2106

EXAMPLE 15

(2E)-3-[4-[[bis[(2,2-dimethyl-1-oxopropoxy)methoxy]phosphinyl]difluoromethyl]phenyl]-but-2-enoyl-norleucinyl-(2S,3R,4S)-methanoprolinyl-glutaminyl-benzylamide

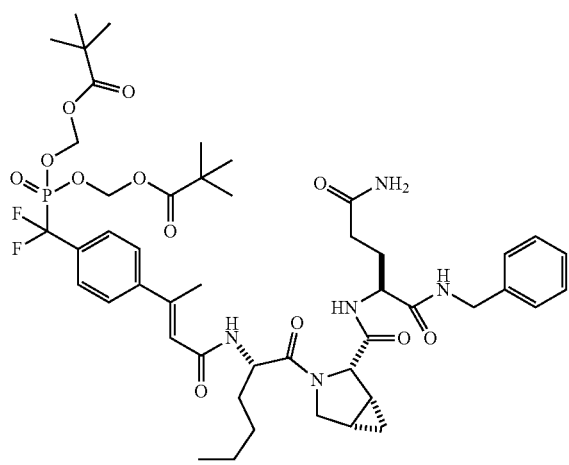

M + H (calc)   M + H (found)
960.4300        960.4300

EXAMPLE 16

(2E)-3-[4-[[bis[(2,2-dimethyl-1-oxopropoxy)methoxy]phosphinyl]difluoromethyl]phenyl]-but-2-enoyl-norleucinyl-(2S,3R,4S)-methanoprolinyl-(4S,5R)-4-amino-5-benzyloxyhexamide

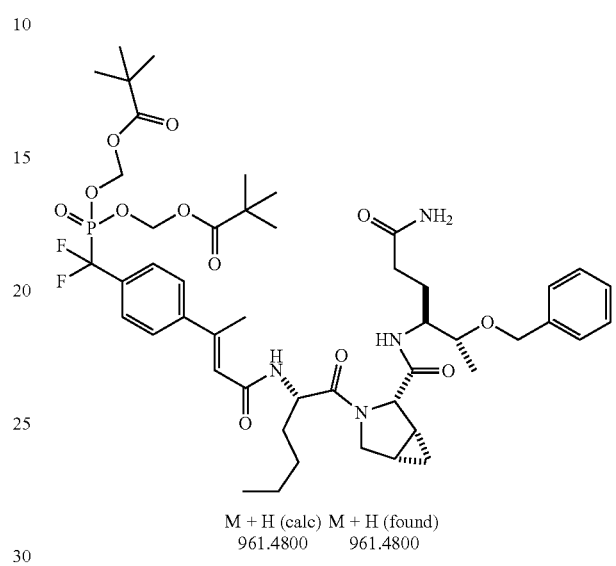

M + H (calc)   M + H (found)
961.4800        961.4800

EXAMPLE 17

(2E)-3-[4-[[bis[(2,2-dimethyl-1-oxopropoxy)methoxy]phosphinyl]difluoromethyl]phenyl]-but-2-enoyl-norleucinyl-(2R,3S,4R)-methanoprolinyl-(4S,5R)-4-amino-5-benzyloxyhexamide

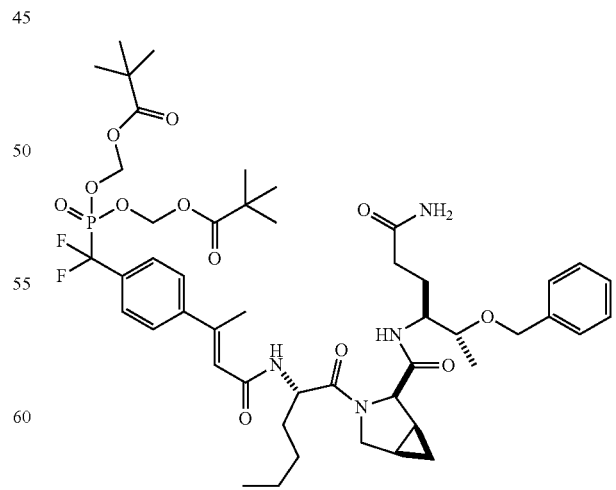

M + H (calc)   M + H (found)
961.4800        961.4759

EXAMPLE 18

(2E)-3-[4-[[bis[(2,2-dimethyl-1-oxopropoxy)methoxy]phosphinyl]difluoromethyl]phenyl]-but-2-enoyl-norleucinyl-(2S,3R,4S)-methanoprolinyl-(R)-4-aminopentamide

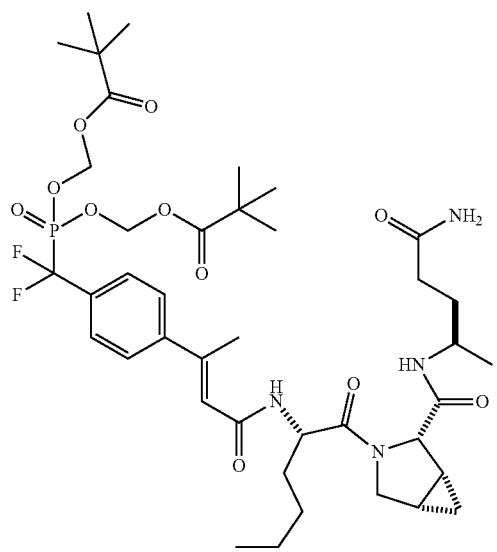

M + H (calc) M + H (found)
841.3964    841.3921

$^1$H NMR (Acetonitrile-$d_3$ 500 MHz) δ 0.64 (m, 1H), 0.78 (m, 1H), 0.9 (m, 3H), 1.07 (d, J=7.0 Hz, 3H), 1.18 (m, 22H), 1.3-1.36 (m, 5H), 1.52-1.57 (m, 2H), 1.67-1.84 (m, 5H), 2.07-2.12 (m, 2H), 2.27-2.33 (m, 5H), 2.45-2.5 (m, 4H), 3.74 (d, J=10.0 Hz, 1H), 3.84 (m, 1H), 4.00 (m, 1H), 4.24 (d, J=5.5 Hz, 1H), 4.56 (m, 1H), 5.53-5.69 (m, 6H), 6.23 (s, 1H), 6.33 (d, J=7.5 Hz, 2H), 6.62 (s, 1H), 6.88 (d, J=7.5 Hz, 2H), 7.57 (d, J=8.0 Hz, 2H), 7.63 (d, J=8.0 Hz, 2H). $^{13}$C NMR (Acetonitrile-$d_3$ 125 MHz) δ 0.2, 0.3, 0.5, 7.9, 13.3, 16.3, 16.4, 19.7, 20.4, 22.2, 26.0, 26.2, 26.4, 27.2, 31.4, 31.7, 32.6, 38.4, 44.1, 50.5, 50.7, 61.9, 82.7, 82.8, 121.2, 126.3, 126.5, 145.7, 148.7, 165.9, 169.2, 172.7, 175.3, 176.4

EXAMPLE 19

(2E)-3-[4-[[bis[(2,2-dimethyl-1-oxopropoxy)methoxy]phosphinyl]difluoromethyl]phenyl]-but-2-enoyl-norleucinyl-(2R,3S,4R)-methanoprolinyl-(R)-4-aminopentamide

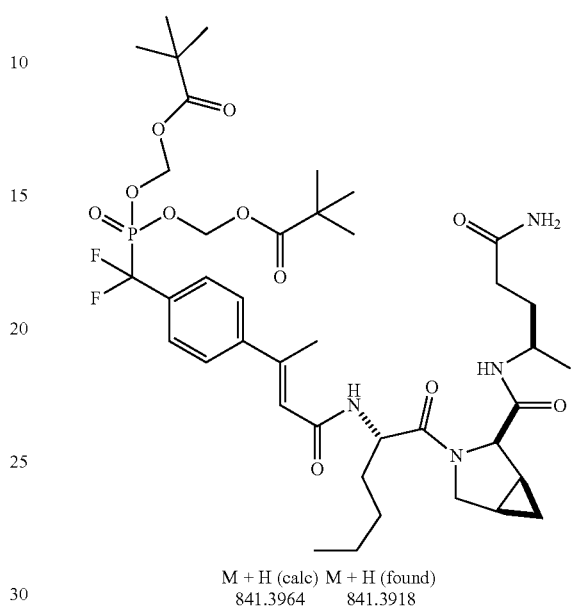

M + H (calc) M + H (found)
841.3964    841.3918

EXAMPLE 20

(2E)-3-[4-[[bis[(2,2-dimethyl-1-oxopropoxy)methoxy]phosphinyl]difluoromethyl]phenyl]-but-2-enoyl-norleucinyl-(Rac)-methanoprolinyl-2-aminoethylurea

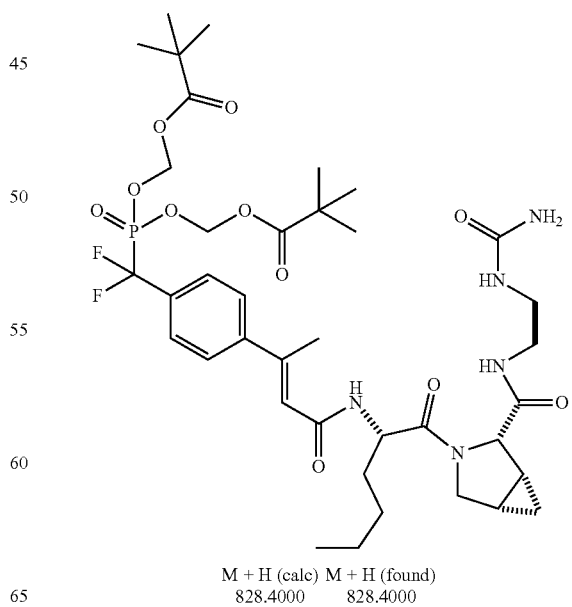

M + H (calc) M + H (found)
828.4000    828.4000

EXAMPLE 21

(2E)-3-[4-[[bis[(2,2-dimethyl-1-oxopropoxy)methoxy]phosphinyl]difluoromethyl]phenyl]-but-2-enoyl-norleucinyl-(2S,3R,4S)-methanoprolinyl-2-aminoethylcarbamate

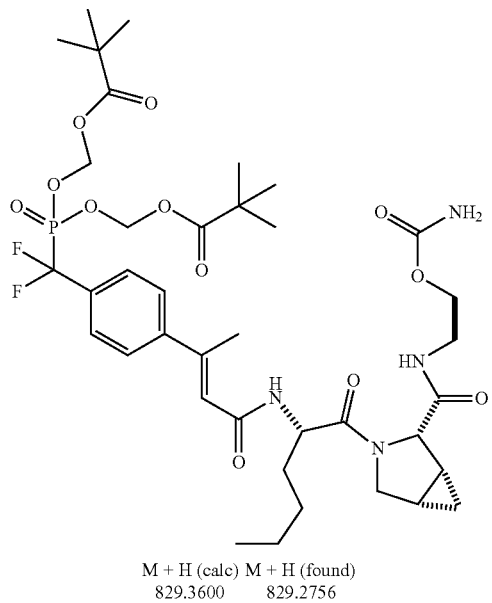

M + H (calc)  M + H (found)
829.3600      829.2756

EXAMPLE 22

(2E)-3-[4-[(Diphenoxyphosphinyl)difluoromethyl]phenyl]-but-2-enoyl-norleucinyl-(2S,3R,4S)-methanoprolinyl-(2S,3R,4S)-methanoprolinyl-(4S,5R)-4-amino-5-benzyloxyhexamide

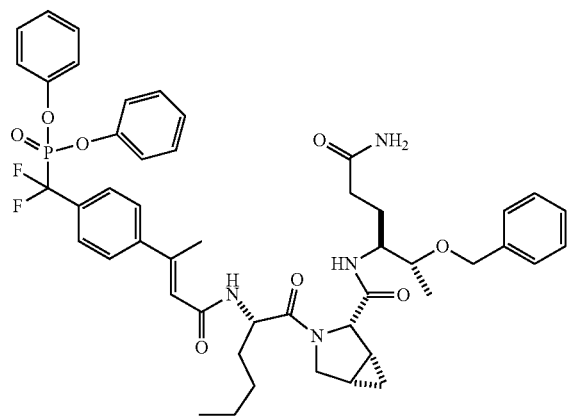

EXAMPLE 23

(2E)-3-[4-[[bis[(2,2-dimethyl-1-oxopropoxy)methoxy]phosphinyl]difluoromethyl]phenyl]-but-2-enoyl-norleucinyl-prolinyl-(R)-4-aminonentamide

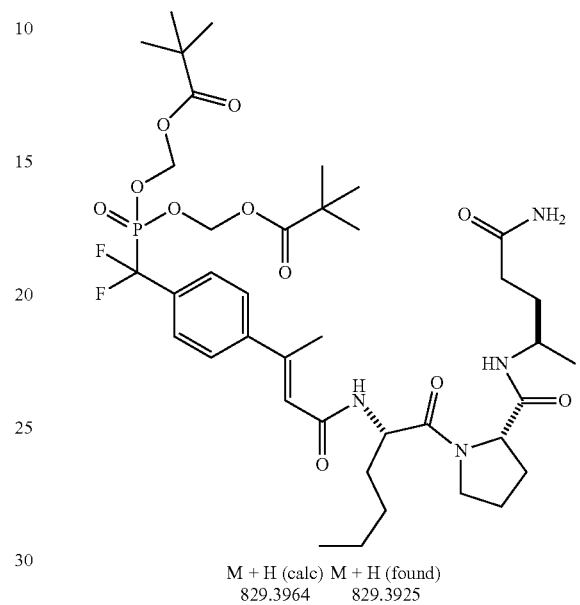

M + H (calc)  M + H (found)
829.3964      829.3925

EXAMPLE 24

(2E)-3-[4-[[bis[(2,2-dimethyl-1-oxopropoxy)methoxy]phosphinyl]difluoromethyl]phenyl]-but-2-enoyl-norleucinyl-4,4-difluoroprolinyl-(R)-4-aminopentamide

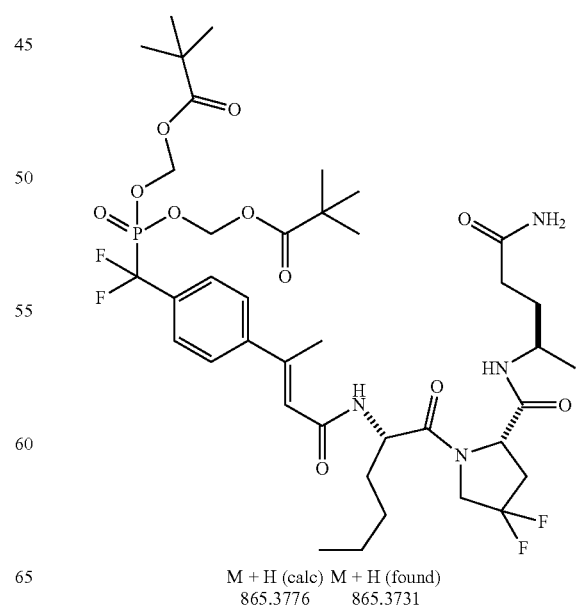

M + H (calc)  M + H (found)
865.3776      865.3731

EXAMPLE 25
(2E)-3-[4-[[bis[(2,2-dimethyl-1-oxopropoxy)methoxy]phosphinyl]difluoromethyl]phenyl]-but-2-enoyl-norleucinyl-4,4-dimethylprolinyl-(R)-4-aminopentamide
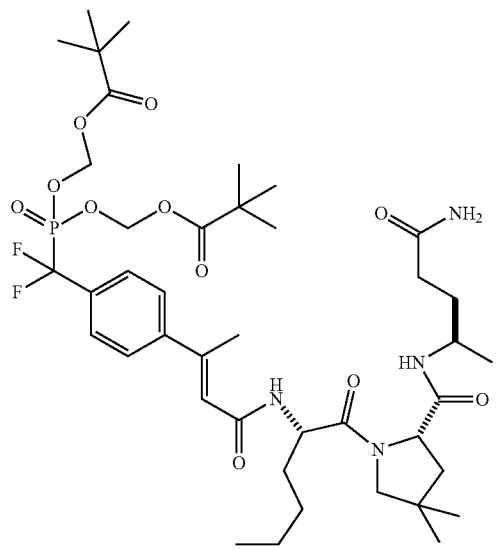
M + H (calc)   M + H (found)
857.4277       857.4200
The following compounds can generally be made using the methods described above.
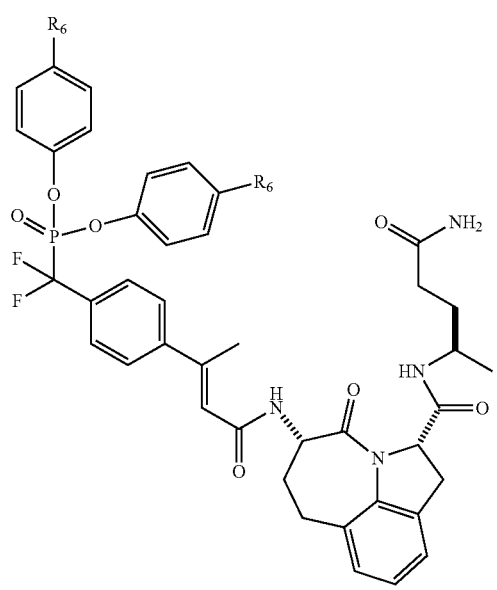
$R_6$ = F, Cl, Br, $NO_2$, $COCH_3$
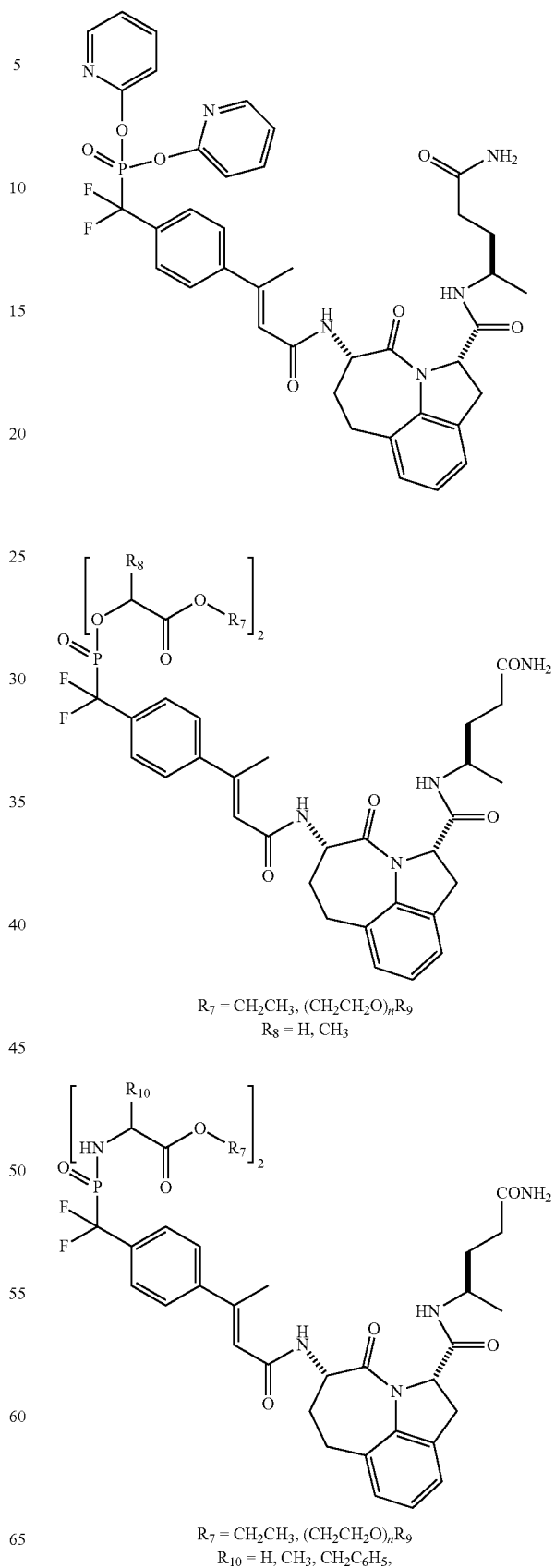
$R_7$ = $CH_2CH_3$, $(CH_2CH_2O)_nR_9$
$R_8$ = H, $CH_3$
$R_7$ = $CH_2CH_3$, $(CH_2CH_2O)_nR_9$
$R_{10}$ = H, $CH_3$, $CH_2C_6H_5$, -continued

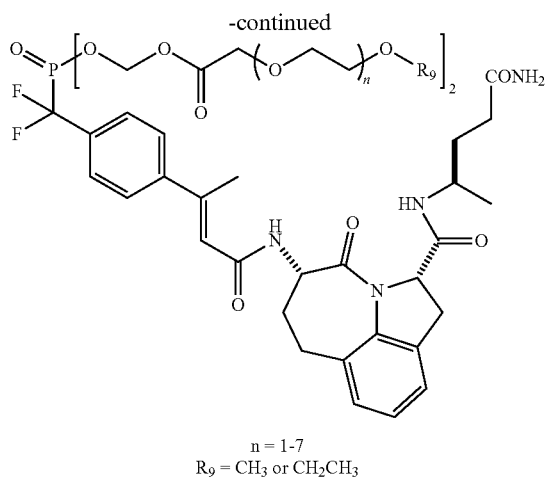

n = 1-7
$R_9$ = $CH_3$ or $CH_2CH_3$

It is expected that these compounds when made will have activity similar to those that have been made in the examples above.

Biological Activity Assays

Cells Acquired: MDA-MB-468 breast tumor cells were acquired from the American Type Culture Collection and were maintained as monolayers in DMEM medium supplemented with 10% fetal bovine serum, 100 mM L-glutamine, 100 μM streptomycin and 100 U/mL penicillin. Cells were grown at 37° C. in an atmosphere of 95% humidified air and 5% $CO_2$. Antibodies against STAT3 (Cat #9132) and pSTAT3$^{Y705}$ (Cat #9145) were purchased from Cell Signaling Technology (Beverly, Mass.).

Fluorescence Polarization Assay: Coleman IV, D. R., et al. *Investigation Of The Binding Determinants of Phosphopeptides Targeted To The SH2 Domain Of Stat3. Development of A High Affinity Peptide Inhibitor*, J. Med. Chem. 48, 6661-6670 (2005). A 50 μl aliquot of a solution of 0.4 μg of full length STAT3 and 20 nM of probe in 50 mM NaCl, 10 mM Hepes, 1 mM $Na_4EDTA$, 2 mM DTT, and 1% NP-40 was placed in wells of a 96 well microtiter plate. To each well was added 50 μl of a peptide solution in the same buffer. Fluorescence polarization was then read in a Tecan Polarian plate reader. Using Prizm Version 4 from GraphPad Software, Inc. the mP was plotted against the log of the peptide concentration and $IC_{50}$ values were obtained from linear regression analysis in the one site competition mode. Peptides were assayed three times using three separate Stat3-probe preparations. $IC_{50}$ values are reported as the mean of three $IC_{50}$ values±the standard deviation. Fluorescence polarization (FP) is a rapid and easy method for the measurement of peptide-protein interactions, drug-protein interactions, and drug-oligonucleotide interactions, and is readily adaptable to high throughput formats. Nasir, M. S., et al., *Fluorescence Polarization: an Analytical Tool For Immunoassay and Drug Discovery*, Comb. Chem. High T. Scr., 2, 177-190 (1999); Owicki, J. C., *Fluorescence Polarization and Anisotropy In High Throughput Screening: Perspectives and Primer*, J. Biomol. Screen., 5, 297-306 (2000). FP involves exciting a fluorophore with polarized light and taking the ratio of fluorescence at right angles after a brief period of time. Small molecules rotate in solution more rapidly than do macromolecules. When the FP probe is free the degree of polarization is smaller than when the molecule is bound to STAT3. FIGS. 1 and 2 show $IC_{50}$ values for the inhibition of Stat3 for two series of lead peptides with varying central scaffolds and 4-phosphoryoxycinnamate units.

Inhibition of STAT3 in BT20 Breast Tumor Cells. General procedure: 35 mm petri dishes were plated with 300,000 BT20 cells in 2 mL RPMI1640 media containing 10% FBS, puromycin, streptomycin, and glutamine. Prodrugs were dissolved in DMSO and were added to the cells with fresh media at varying concentrations. After 2 h the cells were washed with ice cold phosphate buffered saline. Washed cells were treated with lysis buffer (50 mM Hepes, pH 7.4, 150 mM NaCl, 1.5 mM $MgCl_2$, 1 mM EGTA, 100 mM NaF, 10 mM sodium pyrophosphate, 10% glycerol, 1% Triton X-100, 1 mM PMSF, 1 mM $Na_3VO_4$, 10 μg/mL leupeptin and 10 μg/mL aprotinin). Cell-free detergent extracts were centrifuged at 15,000 rpm in a microcentriguge for 30 min at 4° C. and the protein concentrations of the supernatants determined. Aliquots containing 12 μg of protein were separated on 8% SDS-PAGE and were transferred to PVDF filters. The filters were blocked with 5% bovine serum albumin and were probed with pStat3$^{Y705}$ antibody followed by secondary antibody, whose signal was detected with an enhanced chemiluminescence kit (ECL, Amersham, Chicago, Ill.). Filters were stripped with stripping buffer (62.5 mM Tris, pH 6.8, 2% SDS, and 0.1 M 2-mercaptoethanol) at 50° C. for 30 min. Filters were then probed with total Stat3 antibody and visualized with chemiluminescence as above. Western blotting shows dose dependant inhibition of Stat3 phosphorylation.

Figure 3:
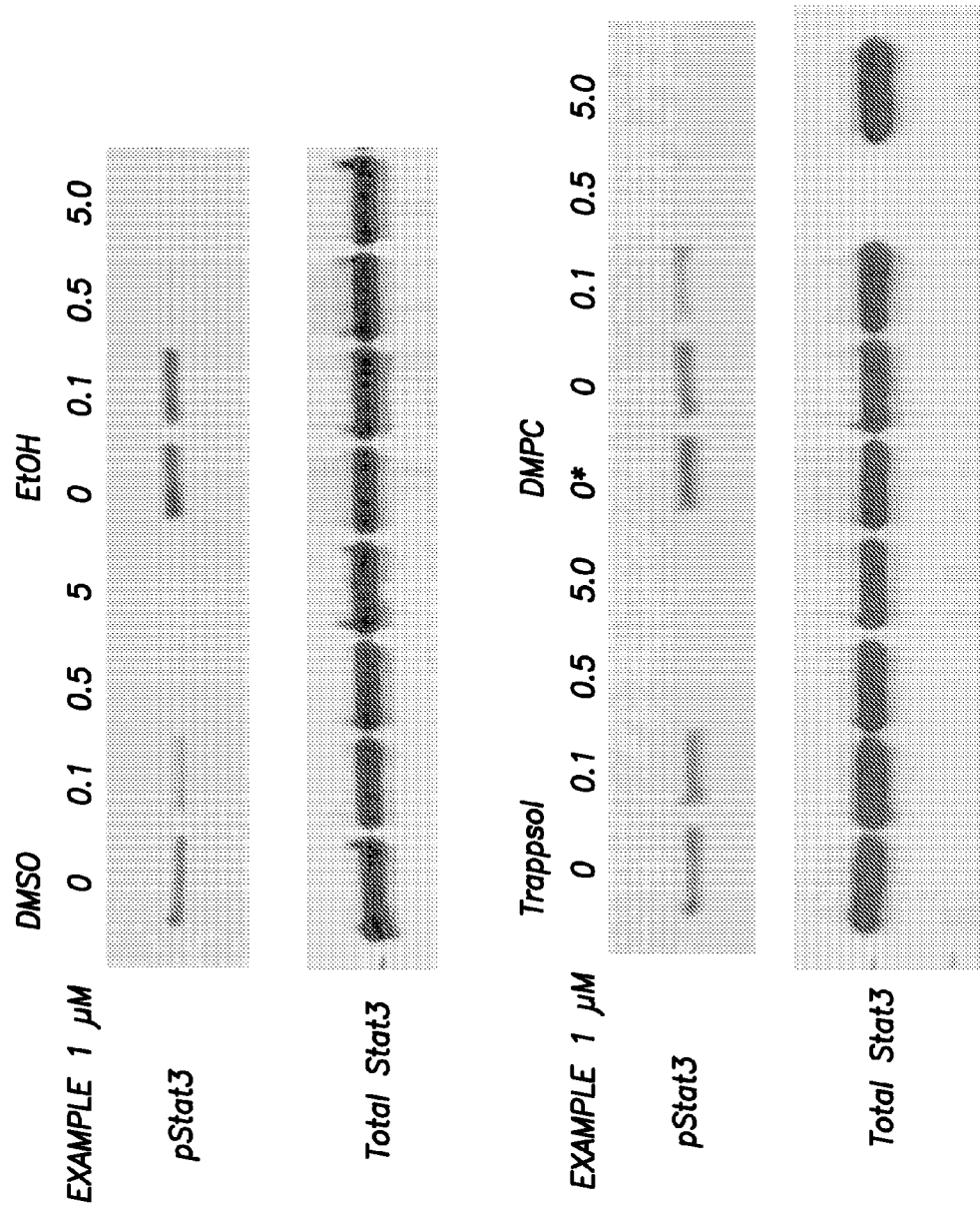
FIG. 3 are western blots show effect of different formulations for administration of the compounds provided herein.

Because DMSO is toxic, other formulations were evaluated for potential use in animal models. The compound of Example 1 was dissolved in EtOH, 20% (w/v) Trappsol (hydroxypropyl β-cyclodextran, pharmaceutical grade), or a liposomal formulation to a concentration of 5 mM. These formulations were given to cells at 0.1, 0.5, and 5 μM concentrations. At two hours, cells were lysed and pSTAT3 levels were determined by Western Blot (FIG. 3). Different formulations have little effect on inhibition of STAT3. The compound of Example 1 was dissolved in DMSO, EtOH, Trappsol, or as a 10 mol % mixture in dimyristoylphosphatidyl choline and applied to BT20 cell in culture. After two hours, cells were lysed and pSTAT3 levels determined by Western blot. The results are shown in FIG. 3. To prepare liposomes a solution of 1.0 mg of the compound of Example 1, 7.2 mg of DMPC, 0.41 mg of Tween 20 in 1.0 mL of tert-butanol was lyophilized. A control lipid formulation of 7.2 mg of DMPC and 0.41 mg of Tween 20 in 1.0 mL of tert-butanol was lyophilized. These samples were mixed with 236 μL of $H_2O$ and were vortexed and sonicated for 5 min. In EtOH, the 0.1 μM sample did not inhibit as much as did the DMSO sample. The other two concentrations were comparable. In Trappsol HPB, the 0.1 μM sample did not inhibit as much as did the DMSO sample. The other two concentrations were comparable. Liposomal preparations exhibited inhibition comparable to DMSO. The lipid controls did not inhibit phosphoSTAT3 formation.

Figure 4:
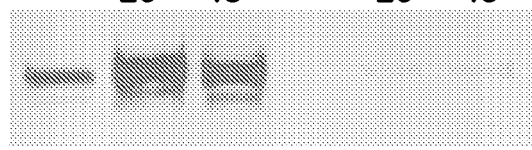
FIG. 4 shows Example 1 is selective for STAT3 over STAT1 and AKT in BT20.
Figure 4:
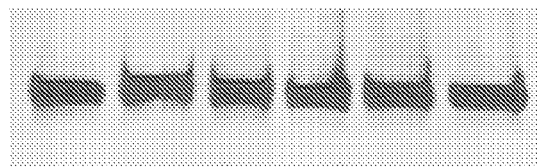
Figure 4:
Figure 4:
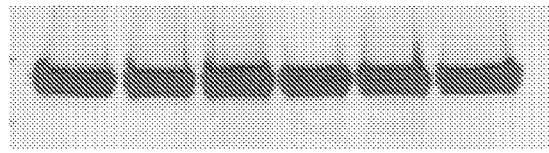
Figure 4:
Figure 4:
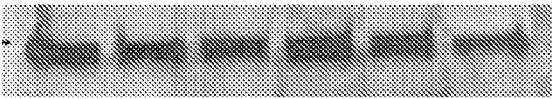

The compounds are selective for STAT3 over STAT1 in BT20 breast tumor cells. BT20 cells prepared as above and were treated with 5 μM of the compound of Example 1 for two hours then were treated with 25 ng/mL of interferon γ (IFNγ). As seen in FIG. 4, IFNγ stimulation resulted in a large increase in phosphoStat1 at 20 and 45 min. However, this compound did not inhibit this process (FIG. 4, middle panel). The compound of Example 1 also inhibited the increase in pSTAT3 formation on EGF stimulation (50 ng/mL) (FIG. 4, top panel). BT20 cells possess constitutively activated Akt, a downstream effector of PI3K (FIG. 4). Treatment with 5 μM of the compound of Example 1 had no effect on pAkt levels, suggesting that this compound does not bind to the SH2 domains of p85, the regulatory subunit of PI3K. (FIG. 4, bottom panel).

Figure 5:
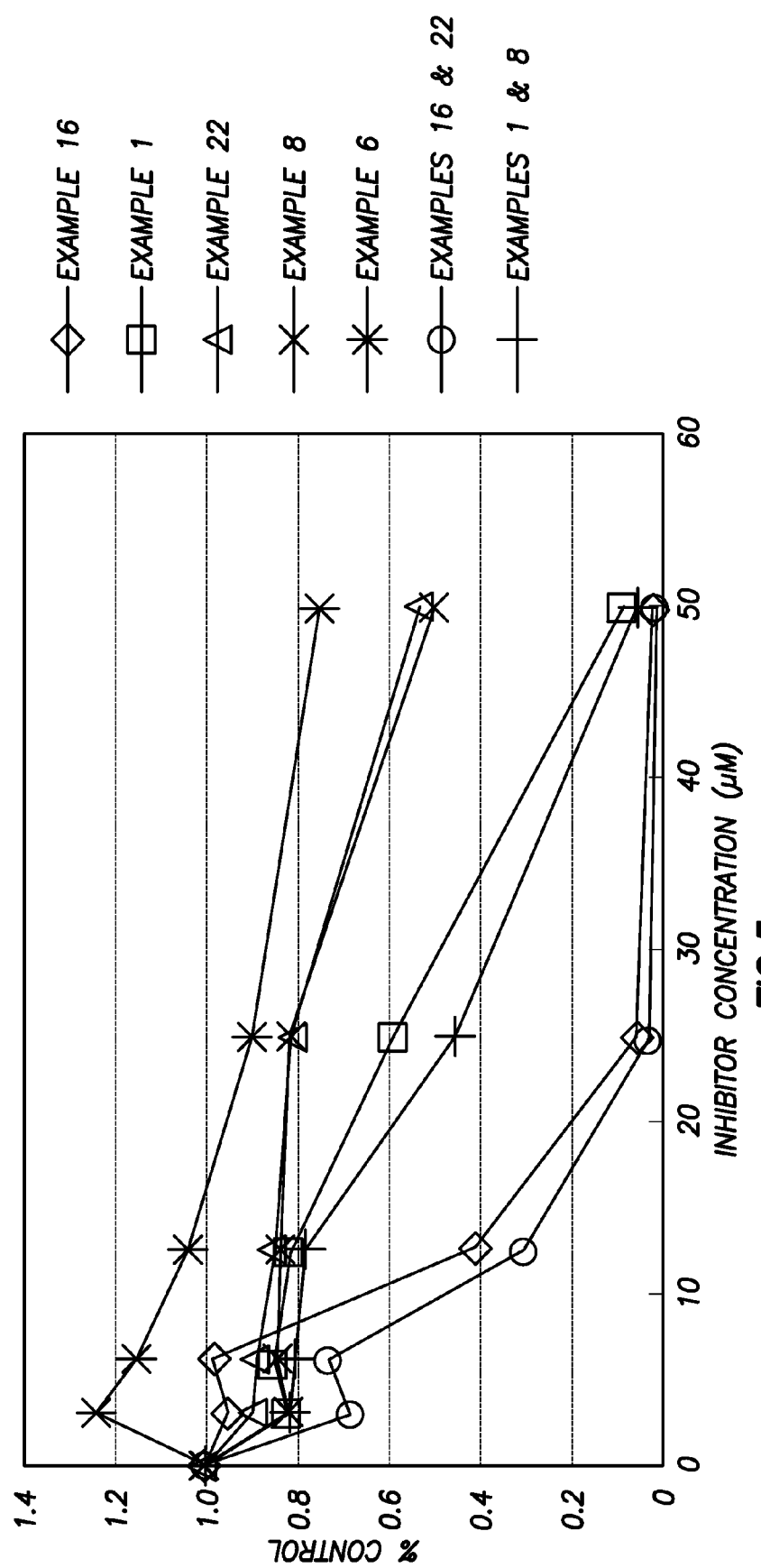
FIG. 5 presents data demonstrating inhibition of proliferation of MDA MB 468 breast tumor cells by a panel of STAT3 inhibitors.
Figure 6:
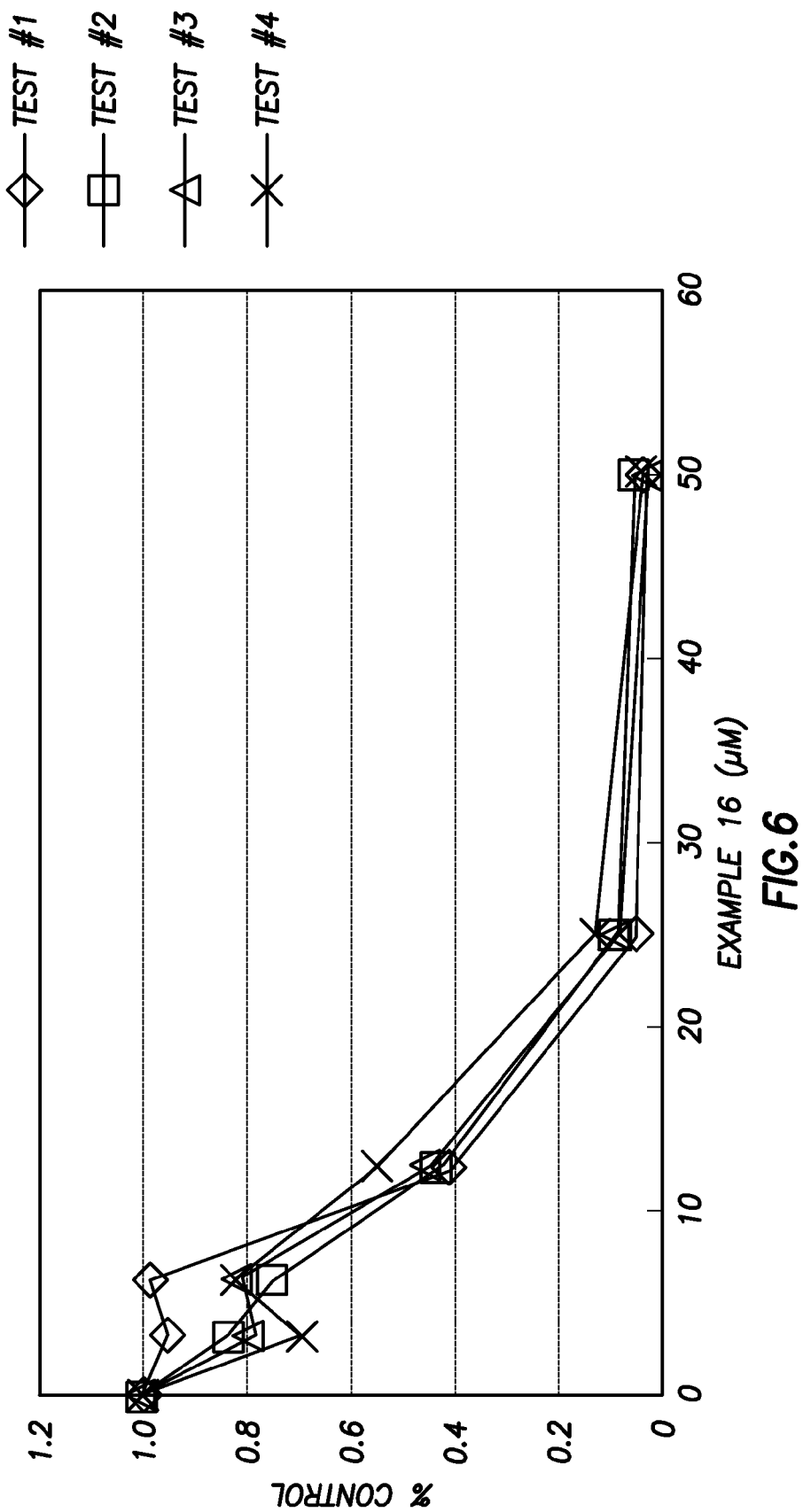
FIG. 6 presents data showing reproducibility of the MTT assay of proliferation of MDA MB 468 cells.

Inhibition of growth of MDA-MB-468 breast cancer cells: The human breast cancer cell line (MDA-MB-468) which harbors phosphorylated STAT3 was used to evaluate the effects of our peptide-based compound on inhibition of STAT3-mediated cell growth. MDA MB 468 cells were plated at 1500 cells/well DMEM with high glucose 10% FBS. Cells were plated into 96 well plates (1500 cells per well) in. After 24 h the media was changed and cells were treated with DMSO or increasing amounts of the compound of Example 1 in DMSO. All wells had equal concentrations of DMSO. At 72 hr viability was measured with the MTT assay. The results are shown in FIG. 5. The compound of Example 16 was shown to be somewhat more potent than the compound of Example 1. In the mixtures of compounds of Examples 16, 22, 1 and 8. the total concentration of the drug is as listed on the X-axis. However, the mixtures are equimolar amounts of both drugs. For example, 5 µM of the drug is actually 2.5 µM of the compound of Example 16 and 2.5 µM the compound of Example 22. The same is true for the mixture of compounds Example 1 and Example 8. In order to demonstrate that the assays are reproducible, four independent assays run on different days. The results are shown in FIG. 6.

Figure 7A:
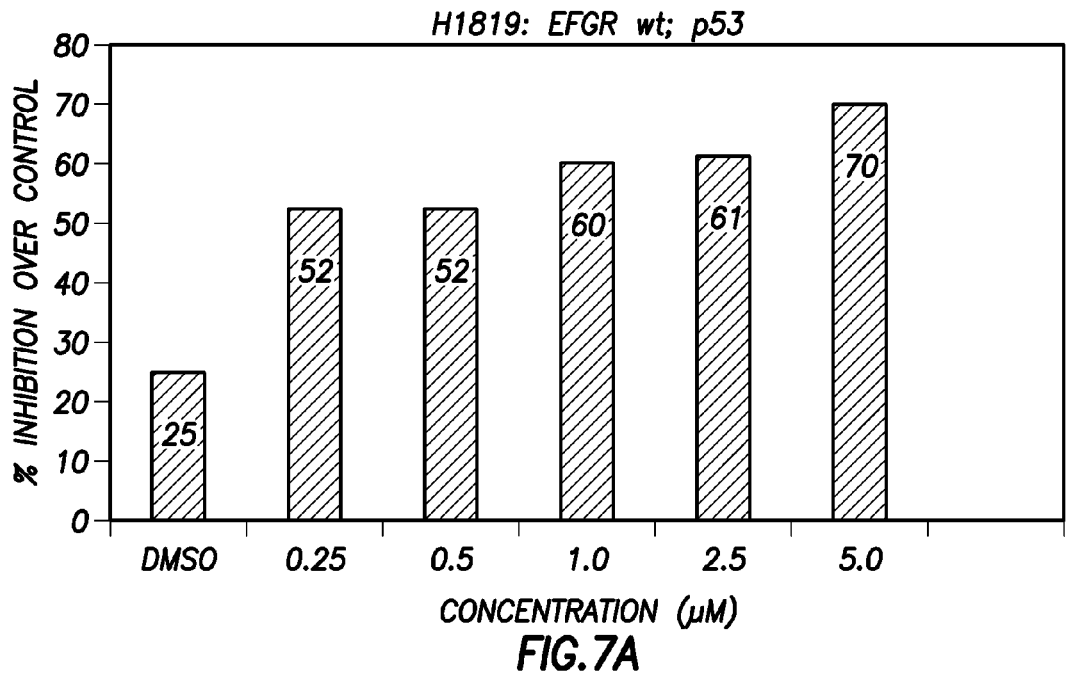
FIG. 7 provides data showing inhibition of non-small cell lung cancer cell lines with the compound of Example 1.
Figure 7B:
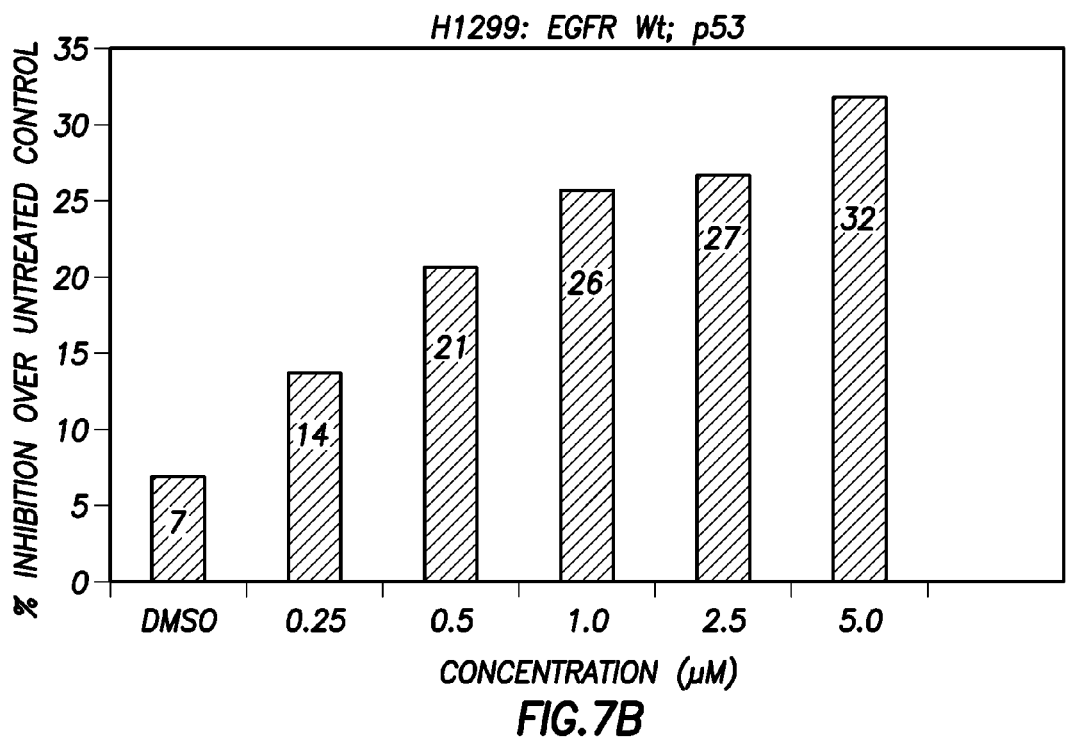
Figure 7C:
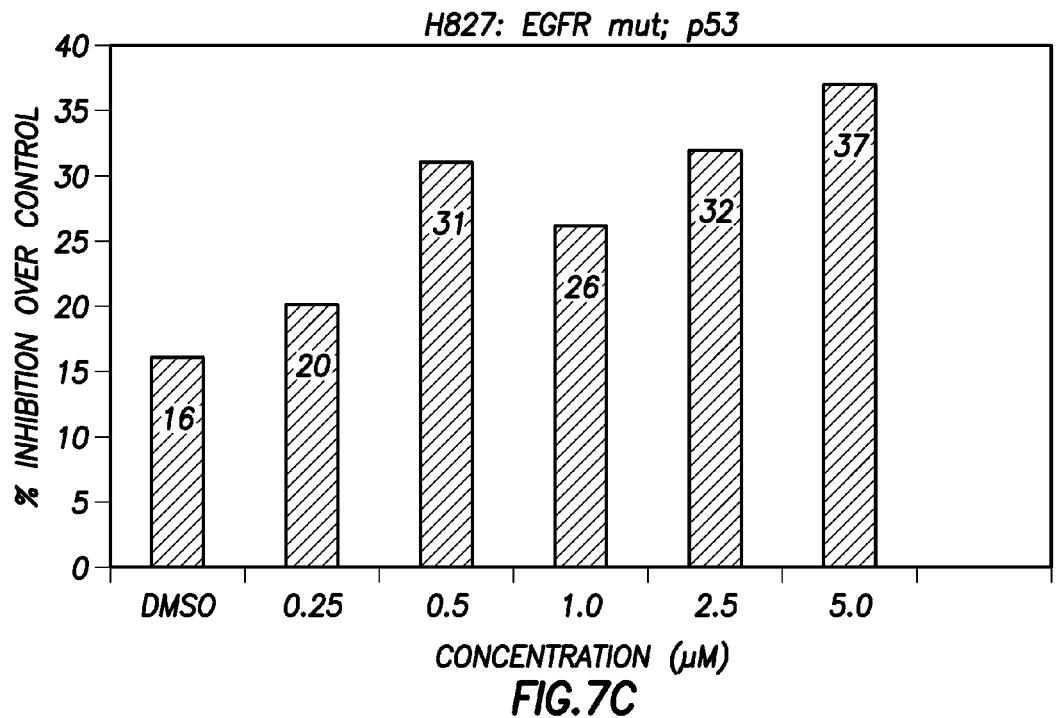
Figure 8A:
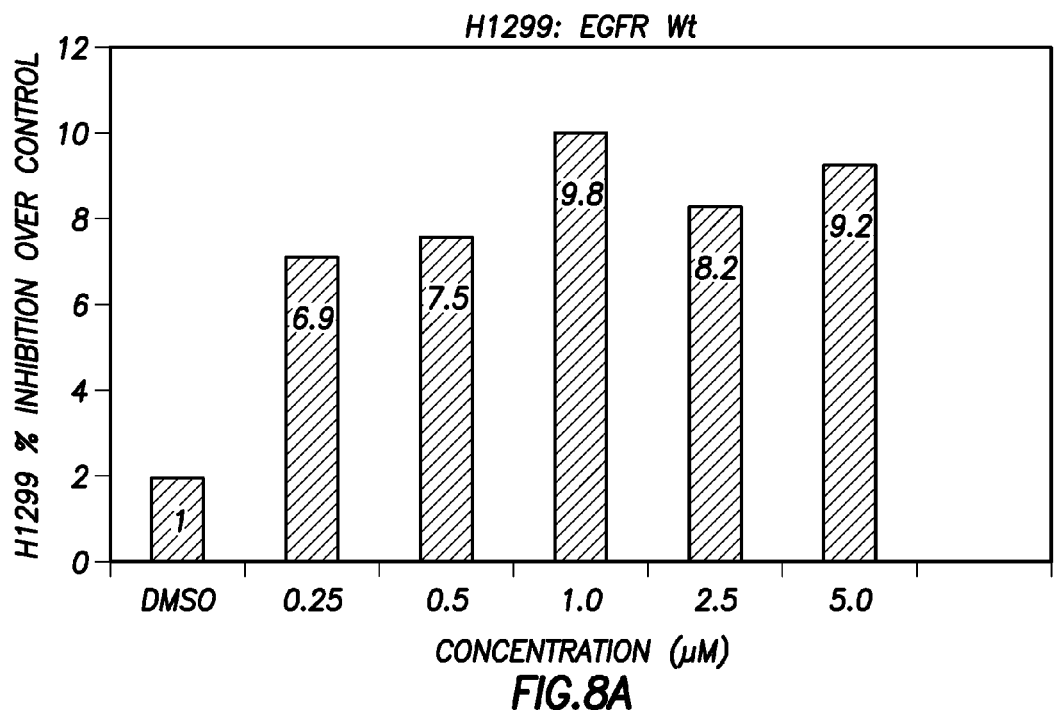
FIGS. 8A through 8G provide data showing inhibition of growth of NSCLC cell lines in culture with the compound of Example 16. Inhibition of HCC827 cells by compound of Example 22 is shown in FIG. 8F.
Figure 8B:
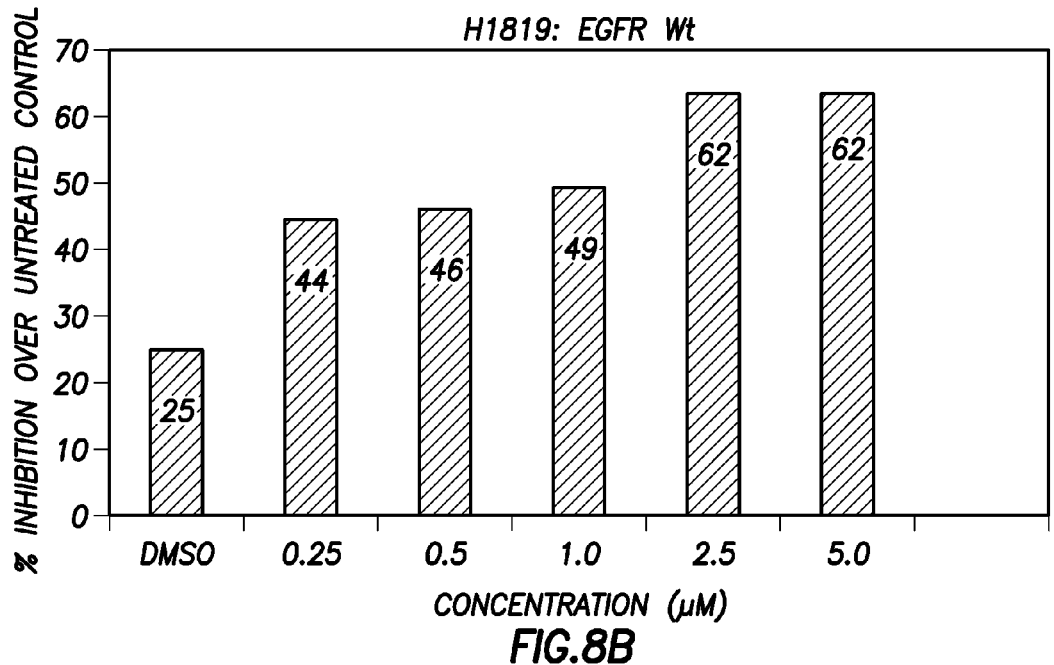
Figure 8C:
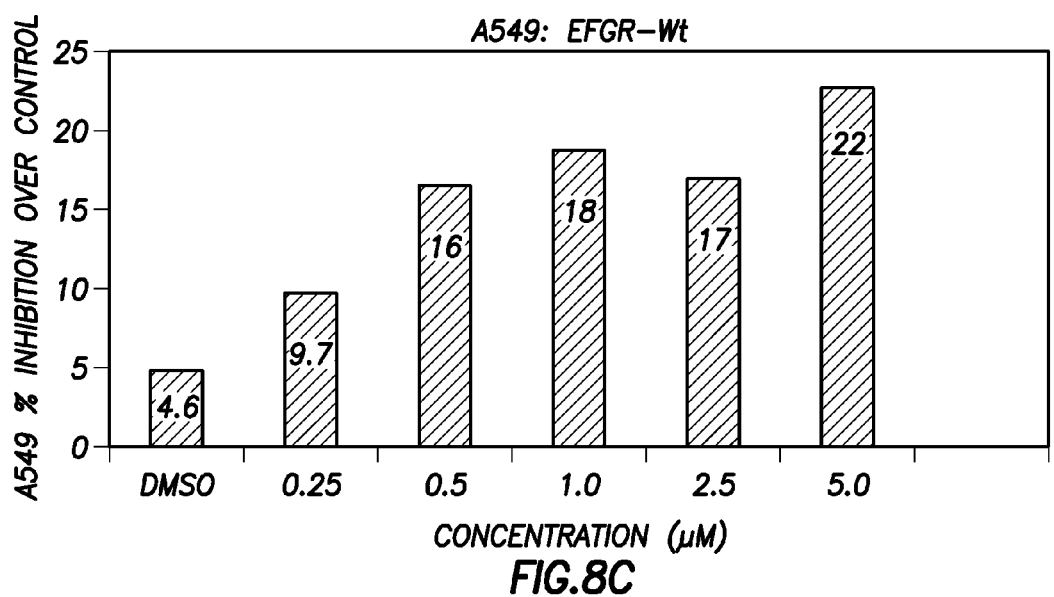
Figure 8D:
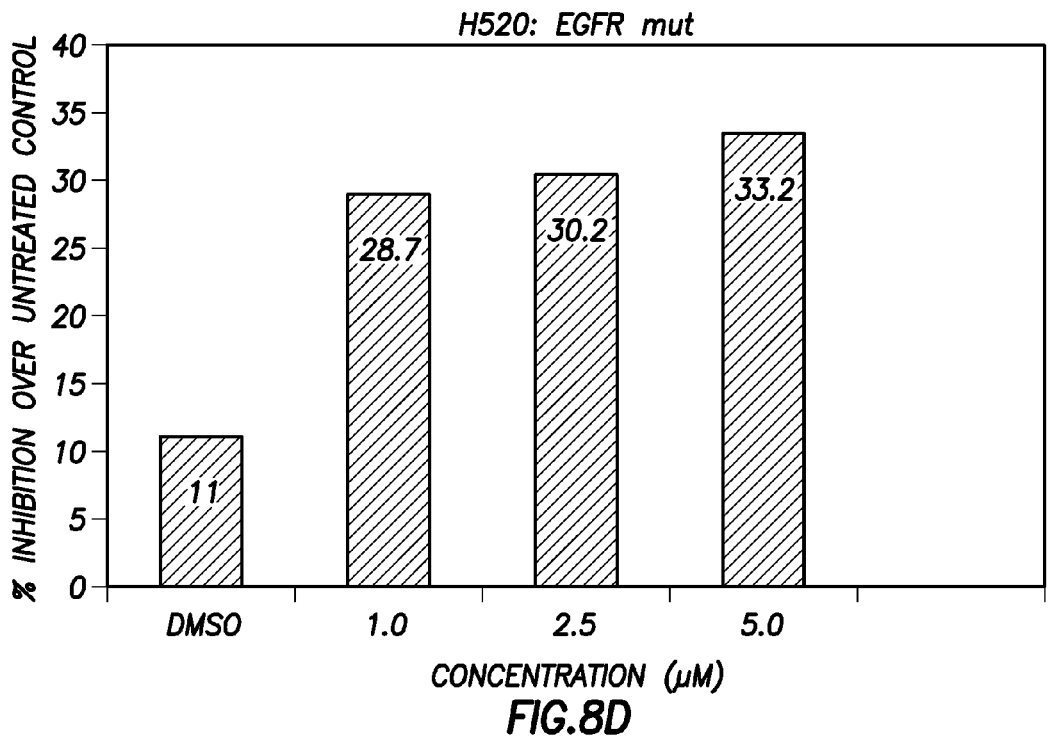
Figure 8E:
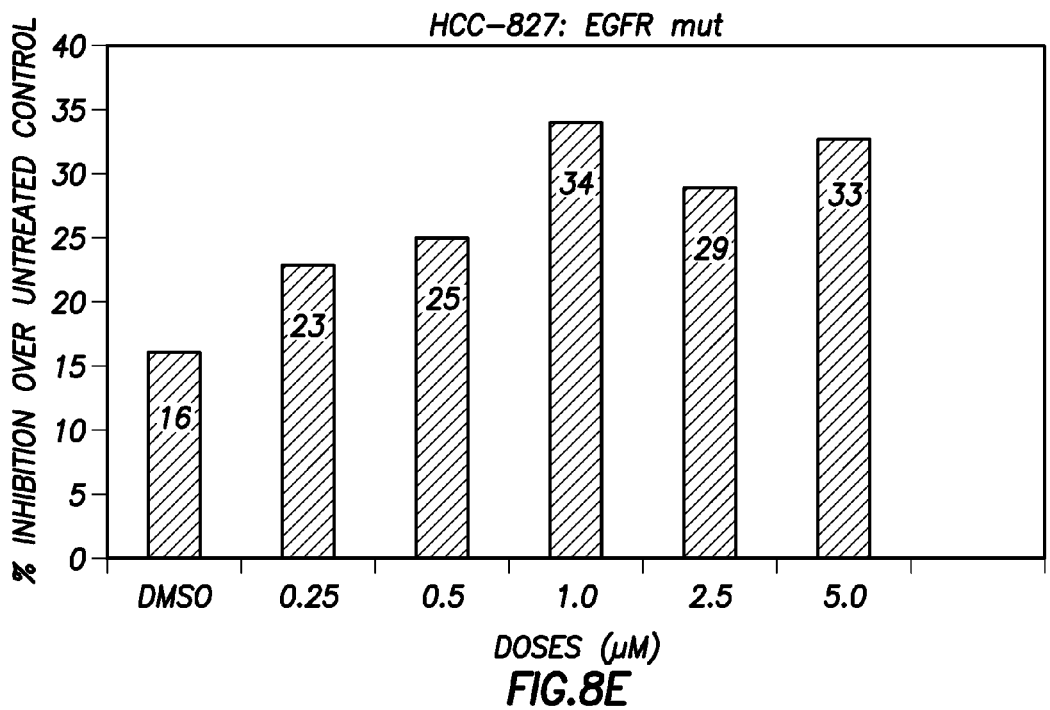
Figure 8F:
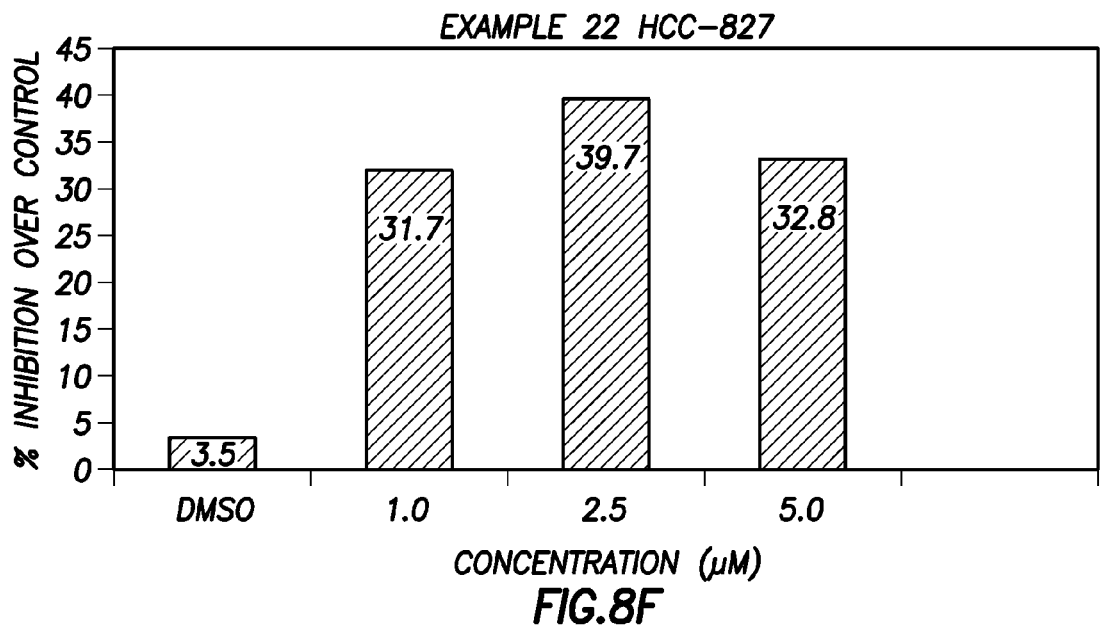
Figure 8G:
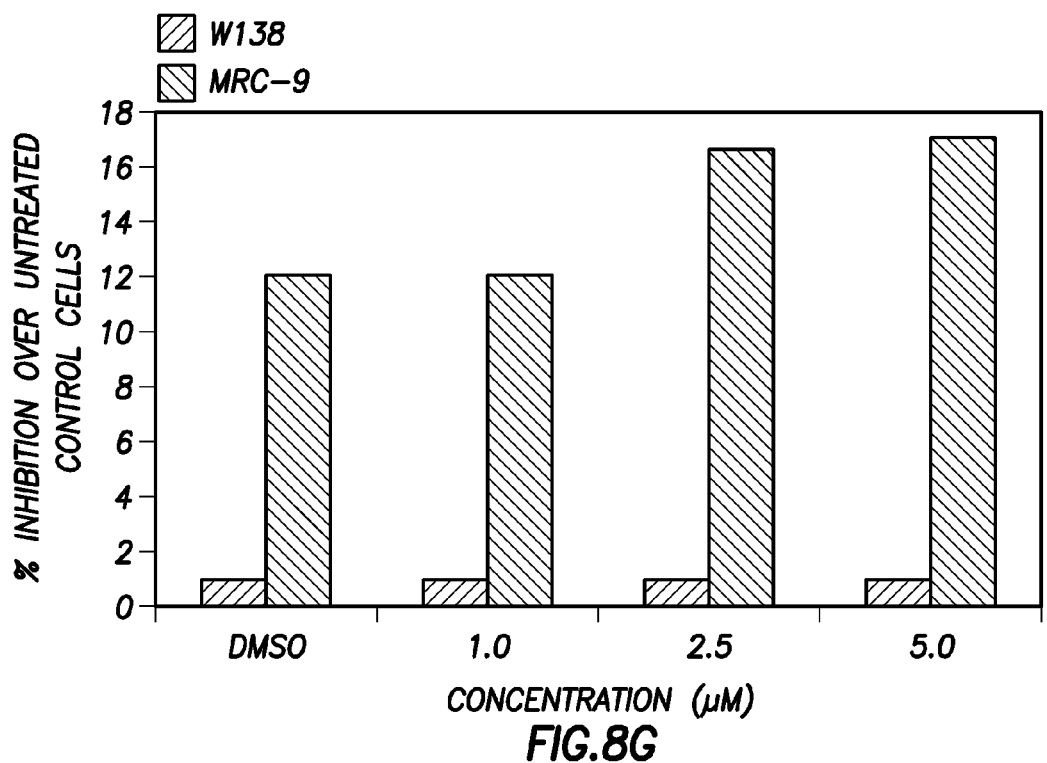
Figure 9:
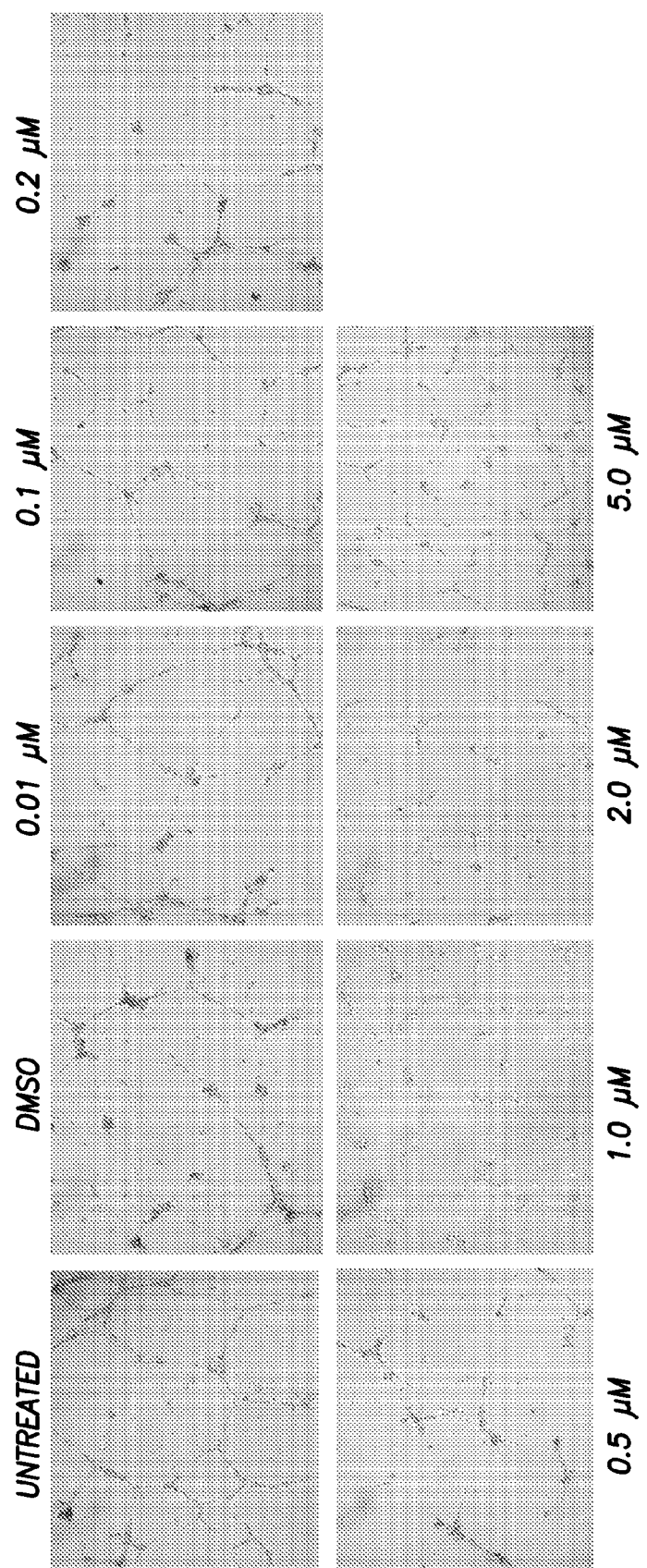
FIG. 9 are images demonstrating inhibition of HUVEC tube formation by the compound of Example 16.

Lung Tumor Cell Viability Assay: H1819, H1299 and H827 lung tumor cells were seeded in 6-well plates at a density of $6 \times 10^4$, $4 \times 10^4$ and $5 \times 10^4$ cells/well, respectively. Prodrugs were dissolved in DMSO to make a stock concentration of 500 µM. The following day the cells were treated either with DMSO alone or with 0.25 µM, 0.5 µM, 1.0 µM, 2.5 µM and 5.0 µM of the compounds from Example 1, Example 16, and Example 22. Seventy two h after treatment with the drug the cells were subjected to cell viability assay using trypan blue. The data is shown in FIG. 7. Inhibition of growth of NSCLC cell lines in culture with the compound of Example 16 was also studied. Cells were plated and after 24 hr were treated with the compound of Example 16 in DMSO. After 72 hr, cells were counted. The results are shown in FIG. 8A through 8E. Note that vertical axes are different for each plot. Inhibition of HCC827 cells by the compound of Example 22 is shown in FIG. 8F. The compound of Example 16 has negligible effects on normal cells compared to the formulation, DMSO, as shown in FIG. 8G Inhibition of tube formation in HUVEC cells. The EC matrix gel was polymerized in the wells of 96-well plates and then incubated at 37° C. for 1 hour to allow the matrix to solidify as per the manufacturers suggestion (In Vitro Angiogenesis Assay kit, Chemicon International, Billerica, Mass. USA, Cat #ECM625). Briefly, $1 \times 10^4$ HUV endothelial cells were seeded on the surface of the polymerized EC matrix gel per well, treated with either DMSO or 0.01 µM, 0.1 µM, 0.2 µM, 0.5 µM, 1.0 µM, 2.0 µM, and 5.0 µM of the compound from Example 1 and the compound from Example 16. The cells were incubated overnight at 37° C. The next day the tubes were observed and the images were captured using a Nikon phase contrast inverted microscope. The results of tests with the compound of Example 16 are shown in FIG. 9. Significant reduction in tube formation was observed at 2 µM demonstrating that these prodrugs may be effective in inhibiting angiogenesis.

Figure 10:
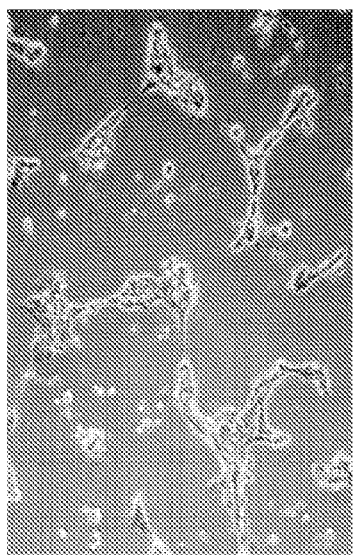
FIG. 10 are images demonstrating inhibition of breast tumor cell line vascular mimicry with the inhibitors provided herein.
Figure 10:
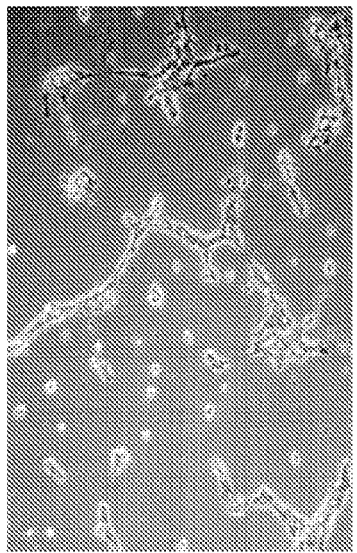
Figure 10:
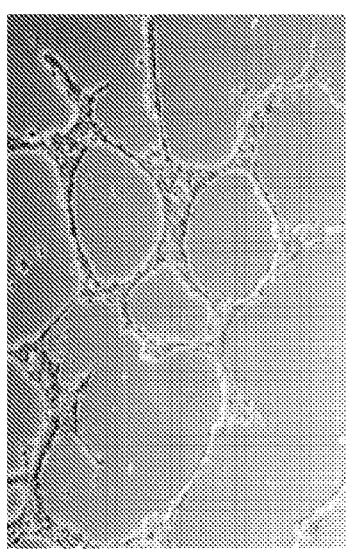

Effects of prodrugs on vasculogenic mimicry exhibited by breast cancer cells MDA-MB-231 and SUM149 cells ($4 \times 10^4$) were added to the top of 24-well plates coated with Matrigel (300 µL) in serum-free DMEM/F12 medium. Cells were treated with 5 µM of the compounds from examples 1 and 8 formulated in DMSO or with DMSO alone as a control. To highlight the matrix-associated vascular channels that were formed, cells were stained with periodic acid-Schiff (PAS) reagent. Representative photographs were taken at 24 hours at _10 magnification. Each experiment was repeated 3 times. Results are shown in FIG. 10. Significant reduction of vasculogenic mimicry was demonstrated with the compound from Example 1. Taken together with the HUVEC data, the results suggest that our compounds have potential as angiogenesis inhibitors.

Figure 11:
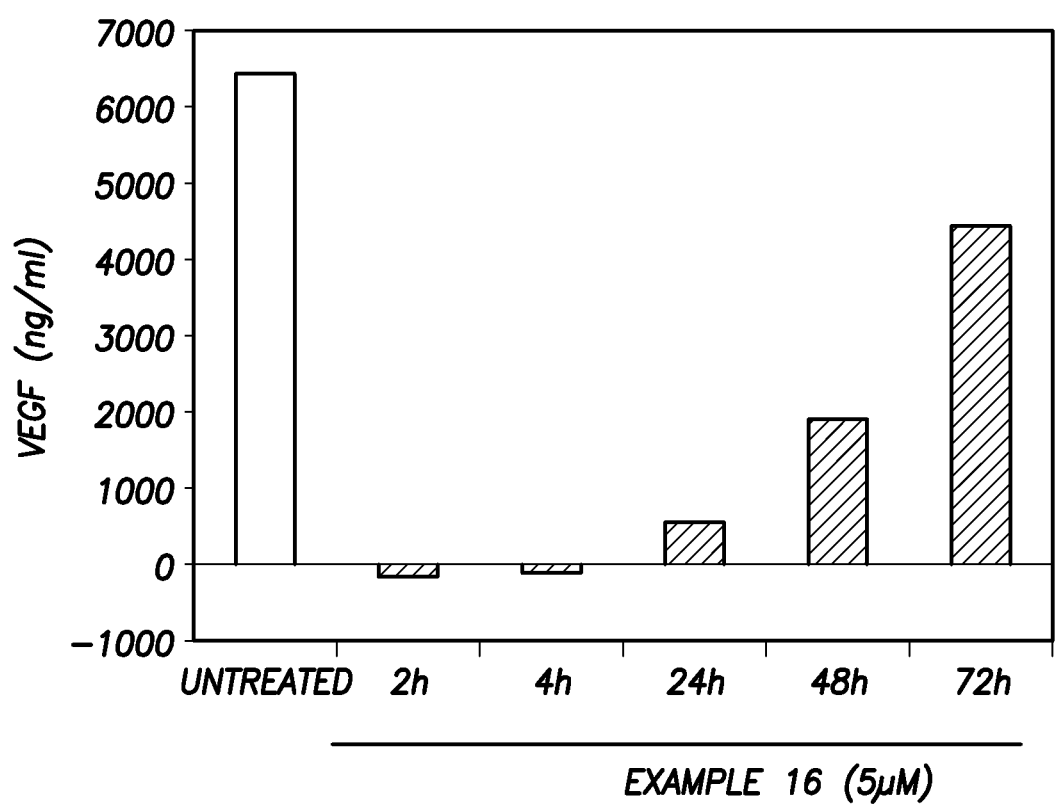
FIG. 11 provides data for inhibition of VEGF production by the compound of Example 16.

Inhibition of VEGF expression in lung tumor cells. HCC-827 were seeded in 6-well plates at a density of $4 \times 10^5$ cells. The following day, the media was replaced with fresh media containing low serum and treated either the compound from example 16 at a concentration of 5 µM. The cells were incubated at 37° C. and the supernatant was collected at 2, 4, 24, 48 and 72 hours post treatment. The supernatant was centrifuged at 2000 rpm for 3 minutes, transferred to fresh tubes and stored at −20 for further analysis. The supernatants were diluted six times with distilled water. The supernatants were then subjected to ELISA analysis for expression of VEGF per the manufacturer's protocol (Quantikine Human VEGF kit, Cat #DVE000. The amount of secreted VEGF and quantified based on the standards and plotted as bar graphs using Microsoft excel. FIG. 11 is a graph of data for inhibition of VEGF production by the compound of Example 16. Indeed, a single dose of 5 µM the compound of Example 16 inhibits the expression and excretion of VEGF for up to 24 hr.

Assay for anchorage-independent growth in soft agar Cells ($5 \times 10^5$) were suspended in 1× DMEM/HEPES, 10% heat-inactivated FBS, 0.13% bicarbonate, and 0.33% BBL agar. The cells were plated on 1% base agar plates (60 mm) containing 1× DMEM/HEPES, 10% heat-inactivated FBS, and 1% BBL agar. Fresh serum-containing medium was fed to the cells on 3-day intervals. The dishes were then incubated at 37° C. with 5% $CO_2$ for 28 days. The colonies that grew in soft agar were photographed and counted. Data are expressed as the number of colonies formed per plate±S.E.M. and three plates were counted per cell line. FIG. 12A shows the inhibition of colony formation of SUM149 inflammatory breast tumor cells by compounds from Examples 1 and 8. FIG. 12B shows the inhibition of four breast tumor models, MDA7, MDA-MB-231, SUM149, and SUM190, with the compound from Example 8 and FIG. 12C shows that the compound from Example 1 effectively inhibited colony formation in these four breast tumor models.

Figure 13A:
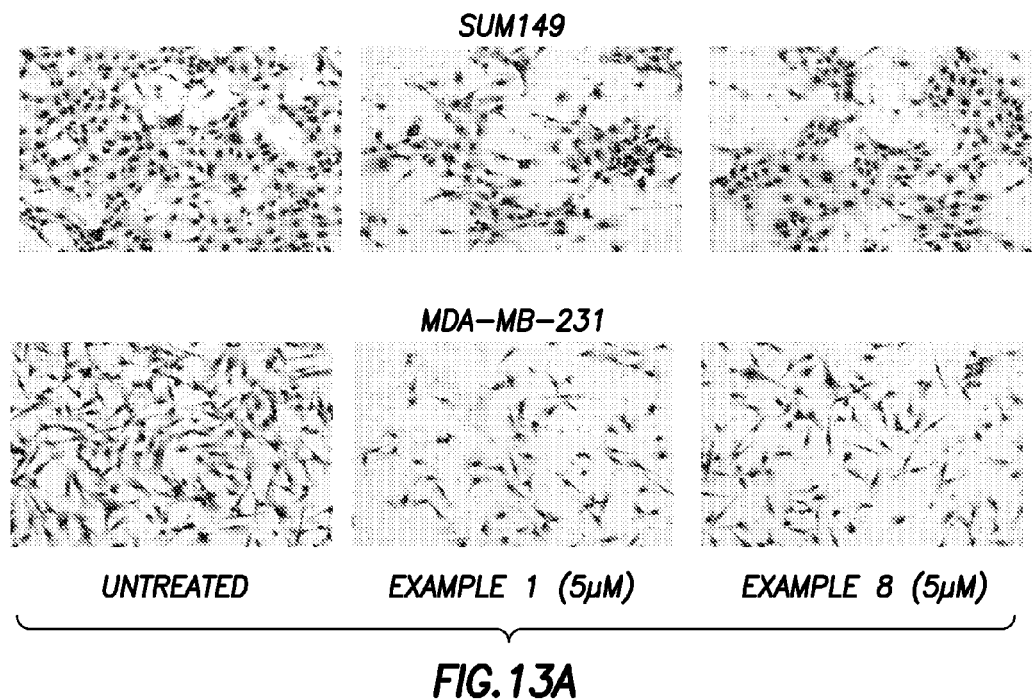
FIG. 13 are images and graphs demonstrating inhibition of invasion of breast cancer cells.
Figure 13B:
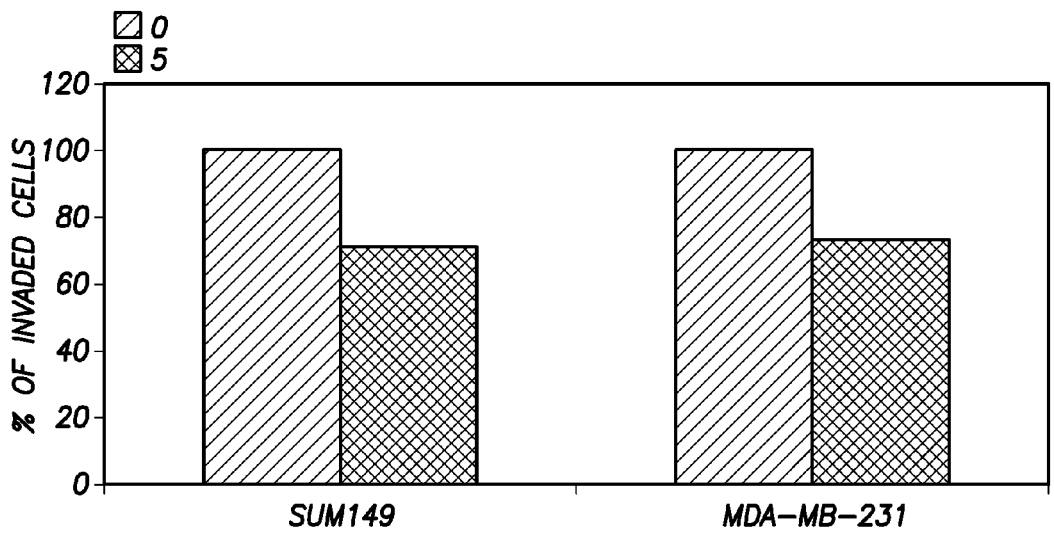

Effect of prodrugs on in vitro invasion of an artificial basement membrane by human breast cancer cells. SUM149 and MDA-MB-231 cells were trypsinized, resuspended in serum-supplemented medium, and counted. Cells were then washed 3 times with serum-free medium. Plates (6-well) compatible with transwell inserts with 8 µm pore-size polycarbonate filters (Fisher Scientific) were coated with Matrigel in cold serum-free DMEM/F12 at a final concentration of 0.7 mg/mL and held at room temperature for 40 minutes. Cells (in 500 µL serum-free medium) were added into the transwell inserts and incubated for 72 hours in the absence or presence 5 µM prodrug in DMSO (1% by volume). For a control, 10% FBS was used to evaluate the baseline extent of invasion of the different cell lines. After incubation, noninvading cells on the upper surface of the filter were removed with cotton swabs. Cells that had passed through the pores onto the lower side of the filter were fixed, stained with Hema-3 stain (Fisher Scientific), and quantified. The experiments were performed in triplicate and were repeated twice. As shown in FIG. 13A, the compounds from Examples 1 and 8 inhibited invasion of these tumor models through the artificial basement membrane. FIG. 13B indicates that the compound from Example 1 is more effective than the compound from Example 8. These results suggest that Stat3 inhibitors will be effective at inhibiting metastasis of malignant tumors.

Figure 14:
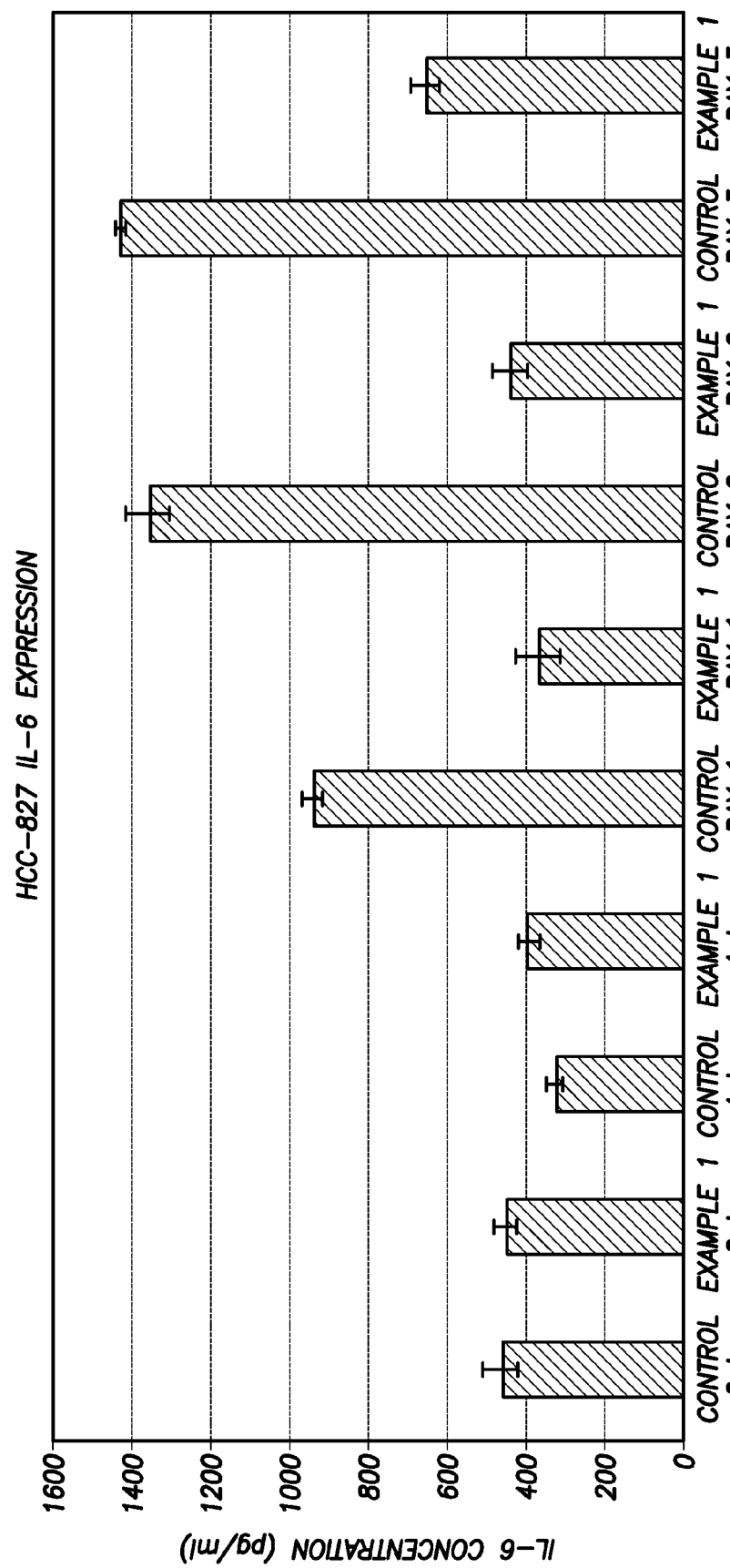
FIG. 14 shows that compounds of the subject invention inhibit expression of IL-6 in a lung cancer cell line.
Figure 15B:
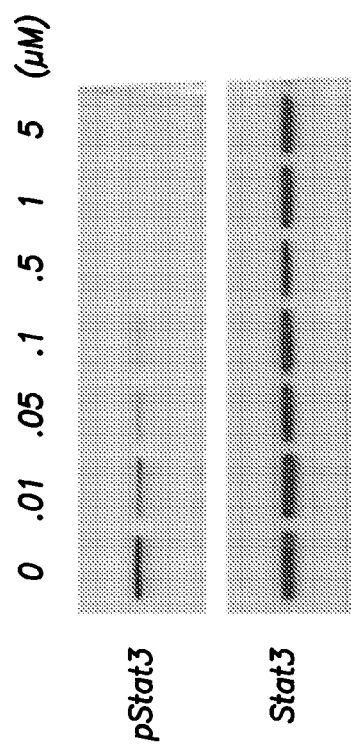
FIGS. 15A, 15B, 15C and 15D show prodrugs with norleucinyl-proline (Compound Example 23), norleucinyl-(2S,3R,4S)-methanoproline (Compound from Example 18), norleucinyl-4,4-difluoroproline (Compound Example 24) and norleucinyl-4,4-dimethylproline (Compound Example 25) as the central scaffold inhibit phosphorylation of STAT3. MDA-MB-468 breast tumor cells were treated with these prodrugs in DMSO for 2 h. Cells were lysed and total and Tyr705 phosphorylated STAT3 were detected with western blots.
Figure 15A:
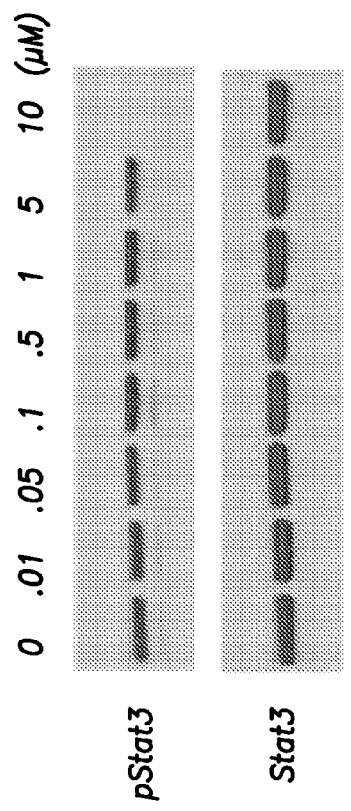
Figure 15D:
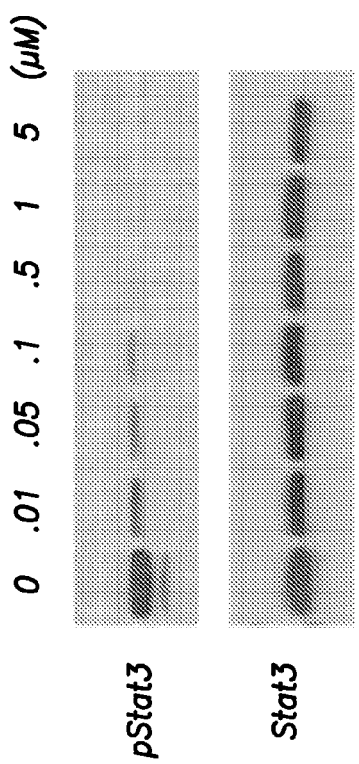
Figure 15D:
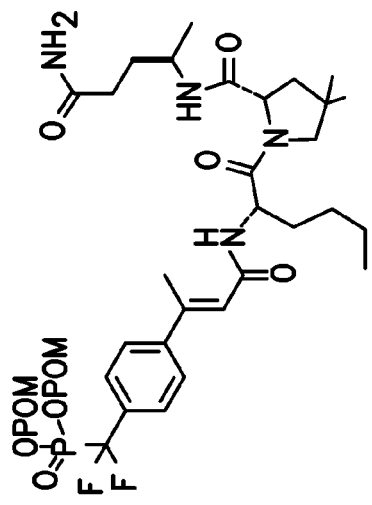
Figure 15C:
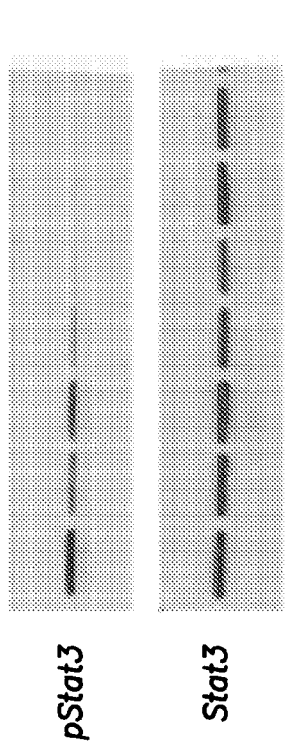
Figure 15C:
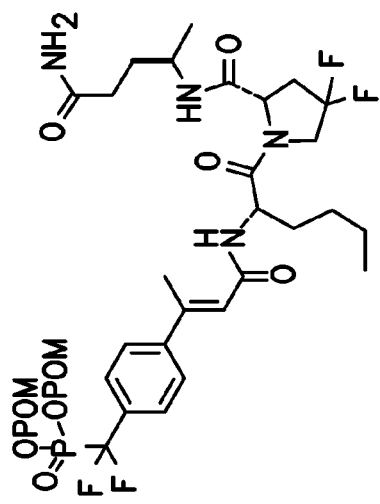
Figure 16A:
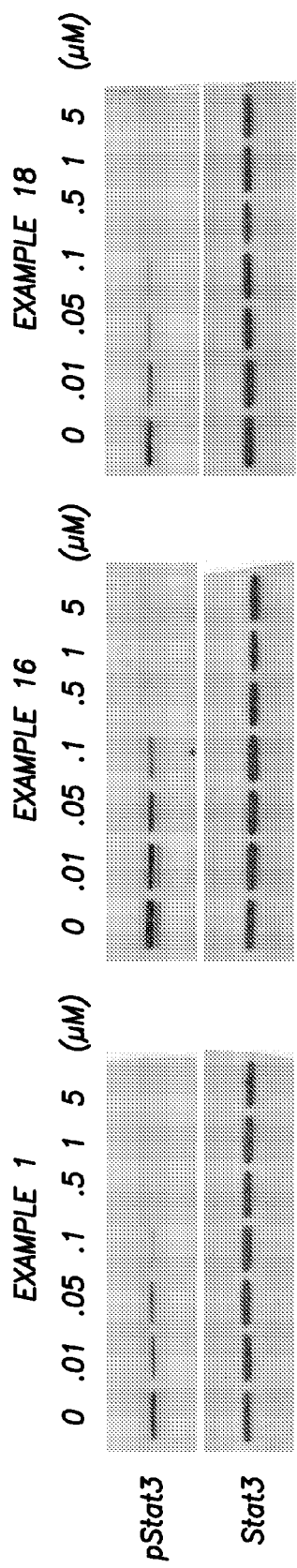
FIGS. 16A, 16B, and 16C show that the compounds of Examples 1, 16 and 18 are very potent. Partial inhibition was seen as low as 10 nM and complete inhibition occurred at 500 nM. The compounds of Examples 17 and 19, incorporating the opposite stereoisomer of cis-3,4,-methanoproline, were much less potent.
Figure 16B:
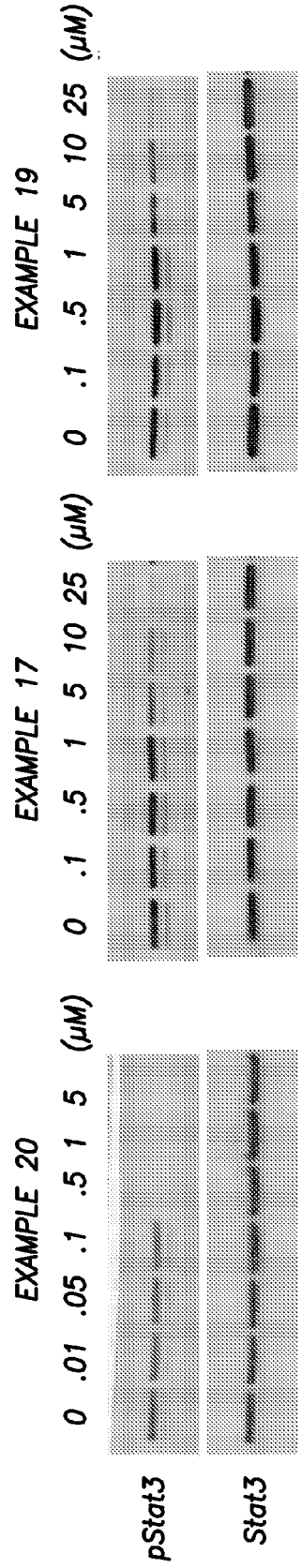
Figure 16C:
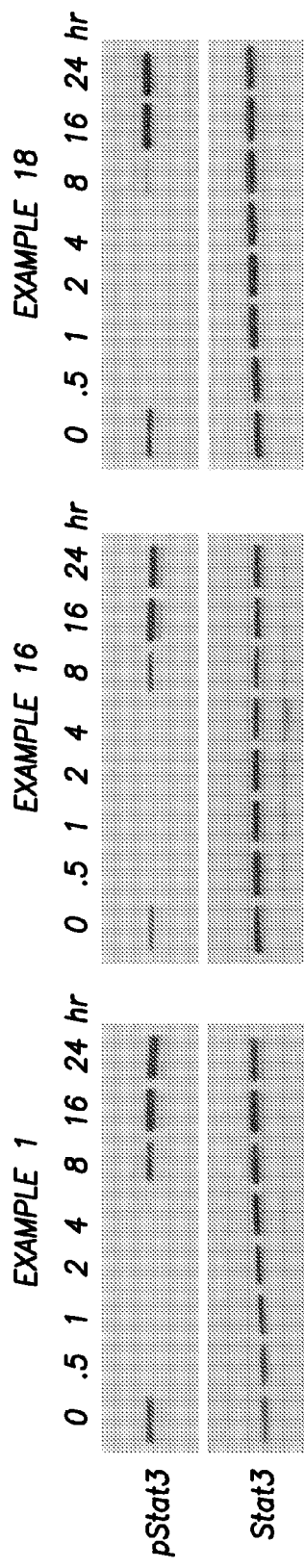

Inhibition of IL-6 expression in lung tumor cells. HCC-827 cells were seeded in 6-well plates at a density of $4\times10^5$ cells/well. The following day, the media was replaced with fresh media containing low serum and treated the compound from Example 1 at a concentration of 5 μM. The cells were incubated at 37° C. and the supernatant was collected at 2, 4, 24, 48, and 72 hours post treatment. The supernatant was centrifuged at 2000 rpm for 3 minutes, transferred to fresh tubes and stored at −20 for further analysis. The supernatants were diluted six times with distilled water. The supernatants were then subjected to ELISA analysis for expression of Interleukin-6 (IL-6) as per the manufacturer's protocol (Hs Human IL-6 kit, R&D Systems, Minneapolis, Minn. USA, Cat #HS600B). The amount of secreted IL-6 was calculated and quantified based on the standards and plotted as bar graphs using Microsoft excel. As shown in FIG. 14, the compound from Example 1 effectively inhibited IL-6 expression for 48 h. Stat3 expresses IL-6 and IL-6 stimulates Stat3 activation, resulting in angiogenesis, cell cycling and cell survival. These results suggest that Stat3 inhibitors may result in reduction of tumor growth through reduction in IL-6 productio Inhibition of Stat3 tyrosine705 phosphorylation in MDA-MB-468 cells. MDA-MB-468 breast tumor cells ($0.4\times10^6$) were plated onto 35 mm culture dishes and were allowed to grow overnight. Prodrugs were prepared as 10 mM stock solutions in DMSO and aliquots were added to the culture media to give the correct final concentrations. After 2 h the cells were washed with ice cold phosphate buffered saline. Washed cells were treated with lysis buffer (50 mM Hepes, pH 7.4, 150 mM NaCl, 1.5 mM $MgCl_2$, 1 mM EGTA, 100 mM NaF, 10 mM sodium pyrophosphate, 10% glycerol, 1% Triton X-100, 1 mM PMSF, 1 mM $Na_3VO_4$, 10 μg/mL leupeptin and 10 μg/mL aprotinin). Cell-free detergent extracts were centrifuged at 15,000 rpm in a microcentriguge for 30 min at 4° C. and the protein concentrations of the supernatants determined. Aliquots containing 12 μg of protein were separated on 8% SDS-PAGE and were transferred to PVDF filters. The filters were blocked with 5% bovine serum albumin and were probed with $pStat3^{Y705}$ antibody followed by secondary antibody, whose signal was detected with an enhanced chemiluminescence kit (ECL, Amersham, Chicago, Ill.). Filters were stripped with stripping buffer (62.5 mM Tris, pH 6.8, 2% SDS, and 0.1 M 2-mercaptoethanol) at 50° C. for 30 min. Filters were then probed with total Stat3 antibody and visualized with chemiluminescence as above. FIGS. 15A-D show that central dipeptide scaffolds possessing modified prolines are very potent inhibitors of the phosphorylation of tyrosine 705 of Stat3. FIG. 16A shows that the compounds from Examples 1, 16, and 18 are very potent inhibitors of tyrosine 705 of Stat3. FIG. 16B shows that the from Example 20 is a potent inhibitor of Stat3 phosphorylation. FIG. 16B also shows that compounds from Examples 17 and 19, which possess (2R,3S,4R)-methanoproline, the opposite enantiomer of (2S,3R,4S)-methanoproline used in the compounds from Examples 16 and 18, are very weak inhibitors of Stat3 phosphorylation. FIG. 16C shows the duration of inhibition of Stat3 phosphorylation.

Figure 17:
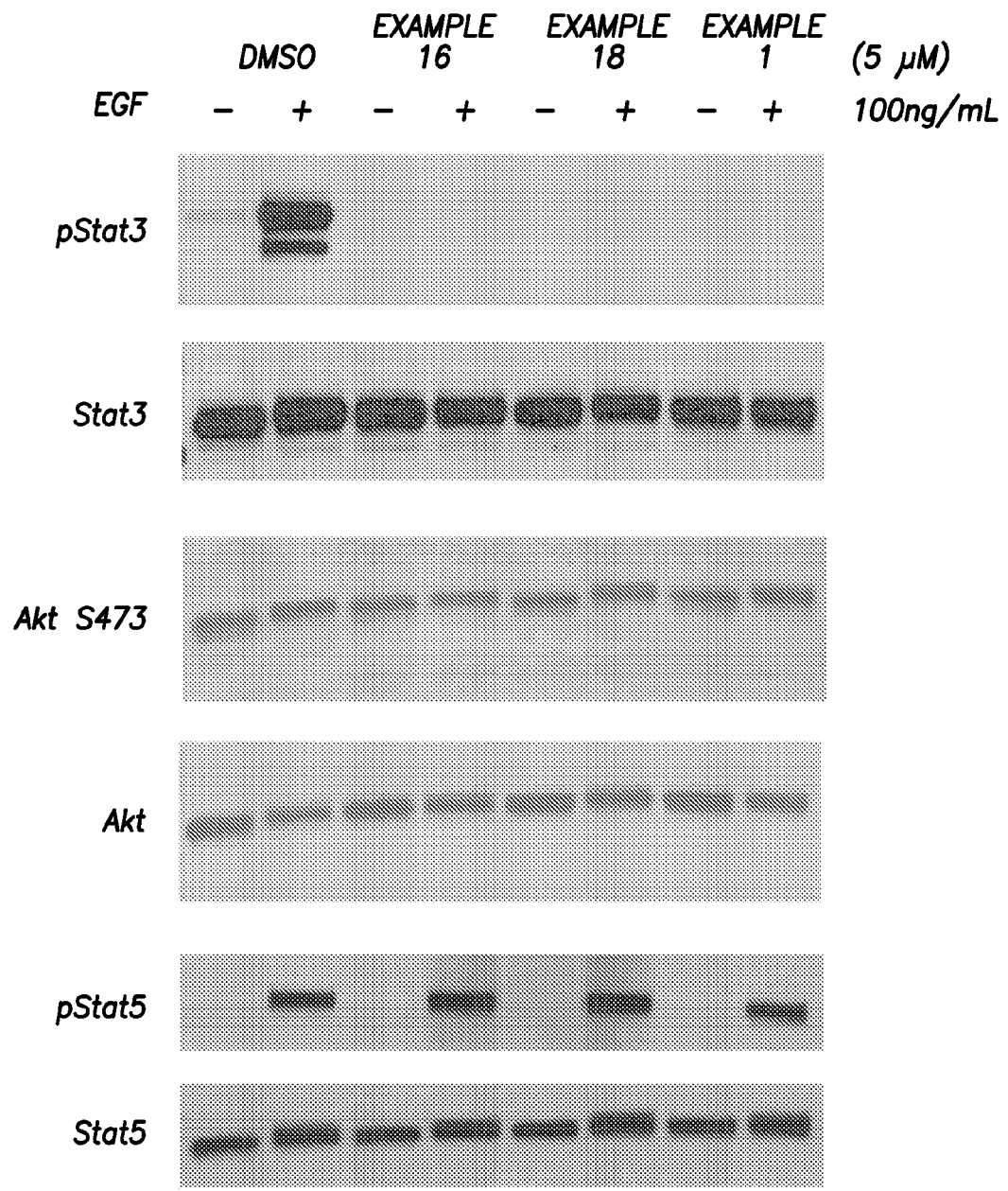
FIG. 17 shows the stimulation of cells with EGF, the compounds inhibit pSTAT3 but do not inhibit phosphorylation of Ser473 of Akt, or Tyr691 of STAT5.

Effect of prodrug on the phosphorylation of STAT3, STAT5 and Akt in response to Epidermal Growth Factor stimulation. MDA-MB-468 cells were prepared as above. Prodrugs were prepared as 10 mM stock solutions in DMSO and aliquots were added to the culture media to give the correct final concentrations. After 1.5 hr EGF was added at 100 ng/mL. After 30 minutes cells were collected and lysed and proteins were separated by PAGE and transferred to three PVDF filters as above. The first filter was blocked with 5% bovine serum albumin and probed for total and phosphoStat3 as above. The second filter was probed for phosphoSer473Akt and total Akt using appropriate antibodies and similar detection procedures to those used for STAT3. The third filter was probed for phosphoTyr699 Stat5 and total STAT5 using appropriate antibodies and similar detection procedures to those used for STAT3. FIG. 17 shows that the compounds from Examples 1, 16, and 18 are effective at inhibiting the increase in Stat3 phosphoryation but have no effect on Stat5 or Akt phosphorylation. Thus these compounds do not bind to the SH2 domains of Stat3 or p85, the regulatory subunit of phosphatidylinositol-3-kinase, the upstream effector of Akt signaling.

Figure 19:
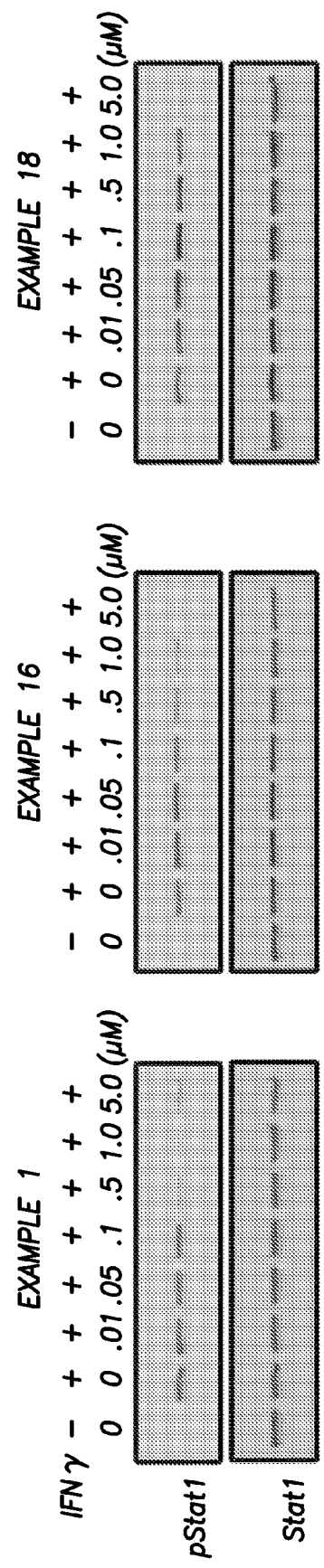
FIG. 19 shows the compounds of Example 1, 16 and 18 are about 10-fold less potent at inhibiting STAT1 than STAT3 in MDA-MB-468 cells.

Effect of Prodrug on the phosphorylation of STAT1 in MDA-MB-468 breast tumor cells. MDA-MB-468 cells were prepared as above. Prodrugs were prepared as 10 mM stock solutions in DMSO and aliquots were added to the culture media to give the correct final concentrations. After 1.5 hr interferonγ was added at 25 ng/mL. After 30 minutes cells were collected and lysed and proteins were separated by PAGE and transferred to PVDF filters as above. Filters were probed for phosphoTyr701 Stat 1 and total Stat1 using appropriate antibodies and similar detection procedures to those used for Stat3. As shown in FIG. 19, compounds from Examples 1, 16, and 18 were less effective at inhibiting Stat1 phosphorylation than Stat3 phosphorylation.

Figure 18:
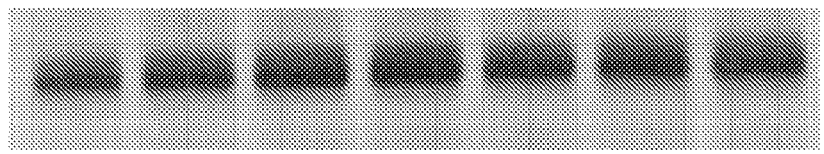
FIG. 18 shows the compounds of Examples 1, 16 and 18 do not inhibit phosphorylation of FAK Tyr861.
Figure 18:
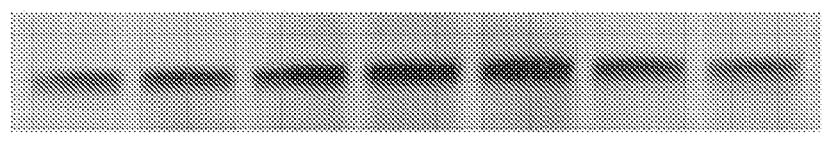
Figure 18:
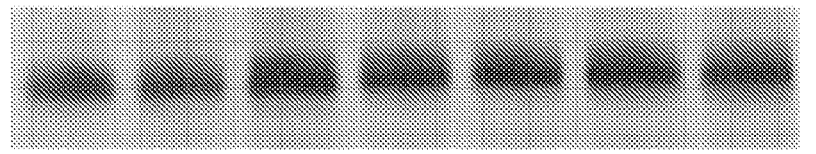
Figure 18:
Figure 18:
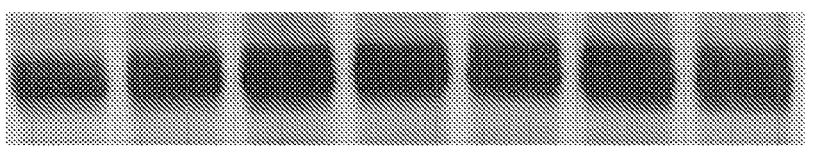
Figure 18:

Effect of Prodrug on the phosphorylation of Focal Adhesion Kinase (FAK) in MDA-MB-468 breast tumor cells. MDA-MB-468 cells express constitutive phosphorylation of Tyr861 of FAK (Laird, A. et al., *Src Family Kinase Activity is Required For Signal Tranducer and Activator of Transcription* 3 *and Focal Adhesion Kinase Phosphorylation and Vascular Endothelial Growth Factor Signaling In Vivo and For Anchorage-Dependent and Independent Growth Of Human Tumor Cells*, Mol Cancer Ther, 2, 461-9(2003). a unique substrate of Src upon recruitment via its SH2 domain (Calalb, M. B., et al, S. K. *Focal adhesion kinase tyrosine-*861 *is a major site of phosphorylation by Src*. Biochem Biophys Res Commun 1996, 228, 662-8 (1996.) To test for cross reactivity to the Src SH2 domain, MDA-MB-468 cell extracts were probed for phosphorylation of Tyr861 of FAK. FIG. 18 shows that after 2 hr treatment with the compounds from Examples 1, 16, and 18, no reduction of Tyr861 phosphorylation was observed. Thus these Stat3 inhibitors do not cross react with the SH2 domain of Stat3.

Figure 20:
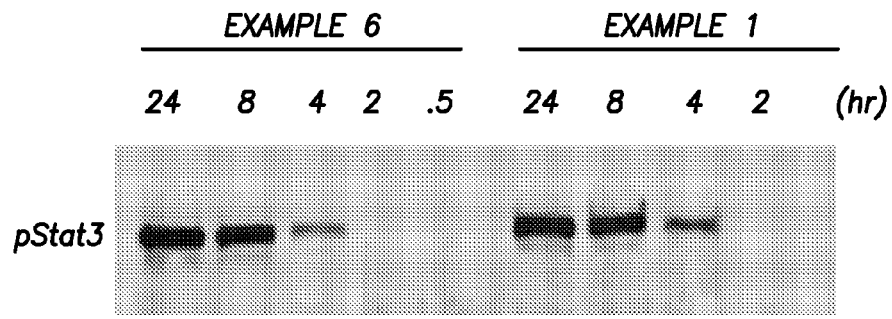
FIG. 20 shows that compounds of Example 6 and 1, both at 5 μM inhibit the phosphorylation of STAT3 in BT-20 breast tumor cells at the indicated time points.

Time course of inhibition of STAT3 phosphorylation in BT20 cells. BT20 cells were plated as above and treated with the compounds from Examples 1 and 6 and western blots were performed at varying time intervals. FIG. 20 shows that both compound inhibit STAT3 phosphorylation up to 8 h. The results suggest that phosphates, Example 8 (X=O) are as effective as difluoromethyl phosphonates Example 1 ($X=CF_2$)

Figure 21:
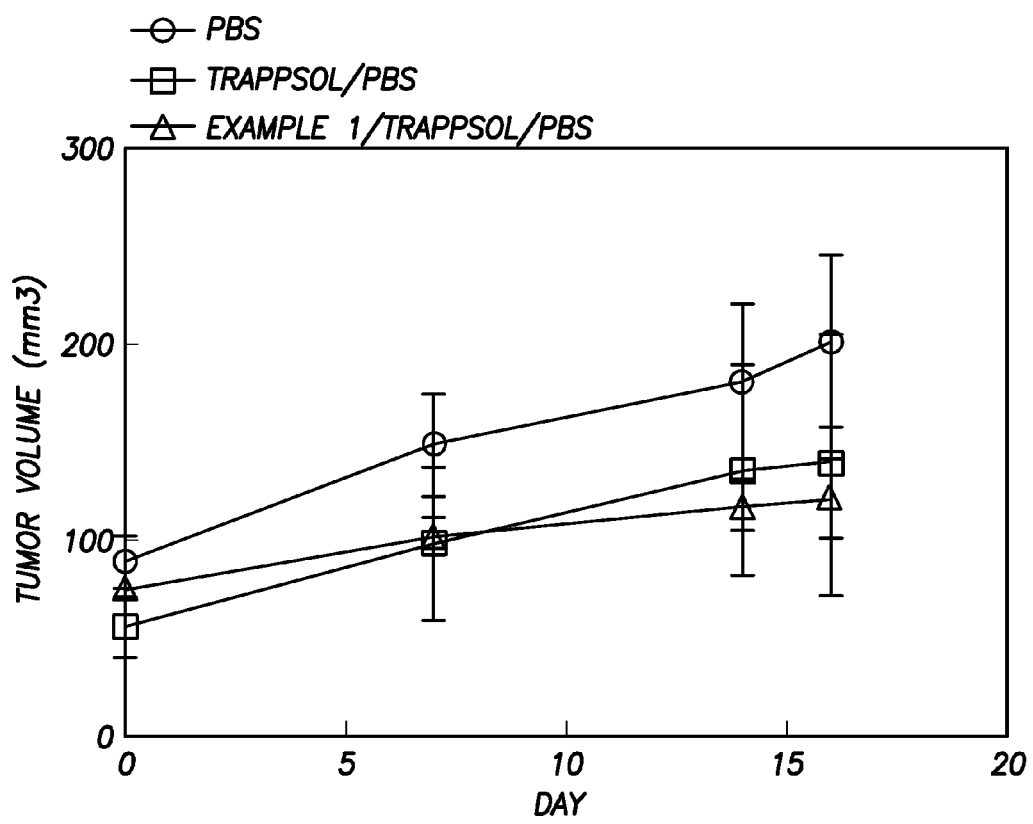
FIG. 21 shows that the compound of Example 1 inhibits the growth of a breast tumor xenograft in nude mice. After 15 days mice were separated into three groups. Group 1 received PBS, group 2 received 20% hydroxypropyl-β-cyclodextrin (Trappsol) in PBS and group 3 received 10 mM of the compound in 20% Trappsol/PBS. Injections of 50 μL were made directly into the tumors. PBS is a phosphate buffered saline having pH7. Mice were treated daily for 5 days, given two days of rest and were treated for 5 days. On day 16 mice were treated and two hours later tumors were harvested, divided into two parts. The first part was frozen and the other was fixed in formalin for immunohistochemistry. Average tumor volume increased 2.3 and 2.5-fold in PBS and Trappsol/PBS vehicle controls, respectively. However, tumors treated with the compound of Example 1 increased in size only 1.6 fold.
Figure 22:
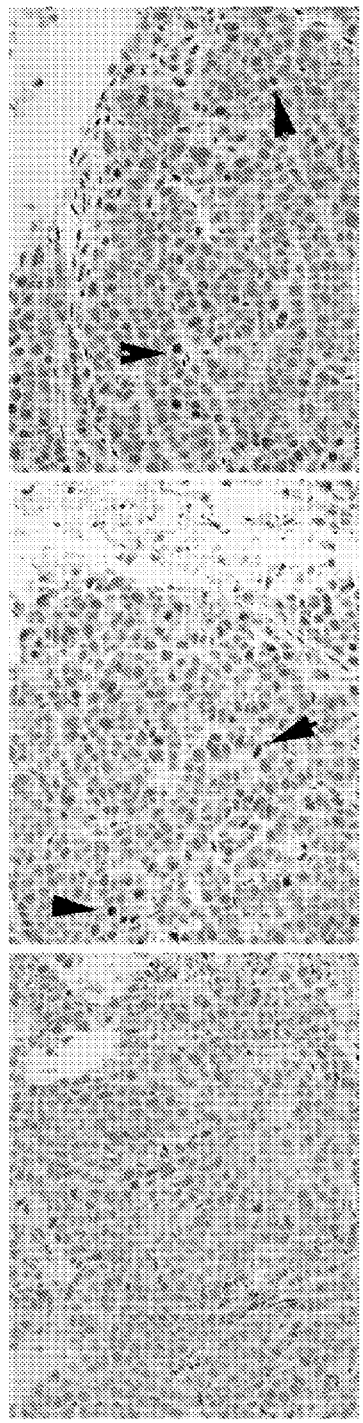
FIGS. 22 and 23 show that the compound of Example 1 strongly inhibited the phosphorylation of STAT3 in treated tumors, as compared to vehicle controls. Together the figures show that there was no apparent difference in CD31 staining in the tissue isolated from mice injected with PBS compared with Trappsol/PBS formulation mixture, suggesting that Trappsol had no effect on angiogenesis during growth of the xenografts. Giatromanolaki, A., et al., *Comparative Evaluation of Angiogenesis Assessment with Anti-Factor-VIII and Anti-CD31 Immunostaining in Non-Small Cell Lung Cancer*, Clin Cancer Res, 3, 2485-92 (1997). In contrast, the centers of tumors treated with the compound of Example 1 in PBS/Trappsol were avascular, with a significant decrease in the number and size of microvessels, as determined by the lack of CD31 staining. These results suggest that this compound has anti-angiogenic activity, potentially targeting angiogenic growth factors such as vascular endothelial growth factor. The centers of tumors treated with this compound were notably acellular, with abundant cellular debris and pyknotic nuclei, suggesting that the inhibitor also induced an apoptotic response. Treated tumors also exhibited a decrease in Ki-67 staining of cells undergoing proliferation, suggesting that the compound of Example 1 has a significant effect on tumor growth, consistent with inhibition of tumor volume in mice treated with this compound compared to mice treated with PBS or PBS/Trappsol. In comparison, there were numerous Ki-67 positive cells within the centers of tumor mass from mice treated with the vehicle controls.
Figure 23:
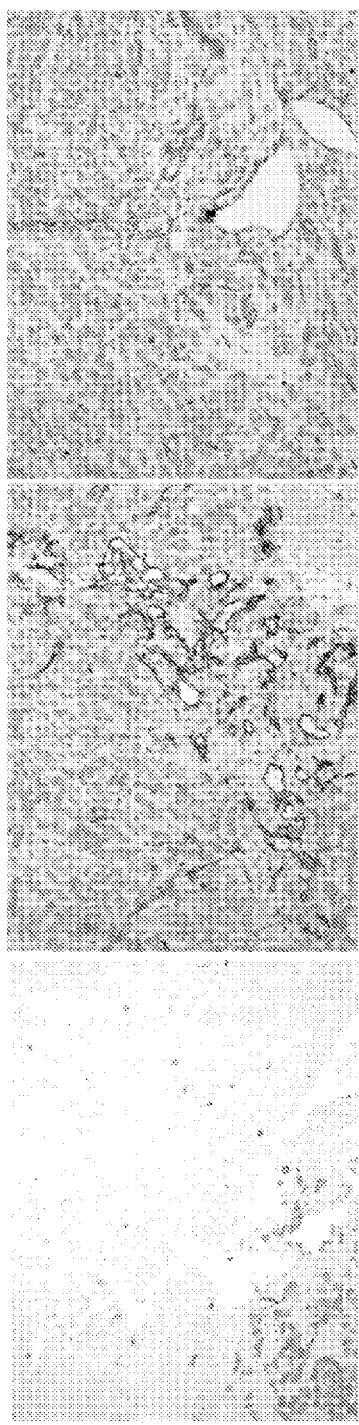

Efficacy of Compound of Example 1 in animal models. The compound of Example 1 was evaluated for inhibition of growth and STAT3 activation in xenografts of MDA-MB-468 cells in mice. See FIGS. 21 through 23. Nu/nu Nude mice were injected in the mammary fat pad with $2\times10^6$ MDA-MB-468 cells suspended in matrigel. After 15 days mice were separated into three groups. Group 1 received PBS, group 2 received 20% hydroxypropyl-β-cyclodextrin (Trappsol) in PBS and group 3 received 10 mM of the compound of Example 1 in 20% Trappsol/PBS. PBS is a phosphate buffered saline with pH7. Injections of 50 μL were made directly into the tumors. Mice were treated daily for 5 days, given two days of rest and were treated for 5 days. On day 16 mice were treated and two hours later tumors were harvested, divided into two parts. The first part was frozen and the other was fixed in formalin for immunohistochemistry. FIG. 21 shows that the rate of tumor growth in inhibited by the compound from Example 1 compared to those treated with the formulation components PBS or 20% Trappsol in PBS. FIG. 22 shows that the phosphorylation of Stat3 in the tumor periphery is reduced by the compound from Example 1 compared to those treated with the formulation components PBS or 20% Trappsol in PBS. FIG. 23 shows that the interior of the tumor was avascular, as evidenced by the lack CD31 staining and exhibited necrosis suggestive of reduced angiogenesis. In contrast tumors treated with the formulation components PBS or 20% Trappsol in PBS displayed high CD31 staining and blood vessel content. These result show that the compound from Example 1 has anti-tumor activity and is an anti-angiogenesis agent.

We claim:

1. A compound of structural Formula I

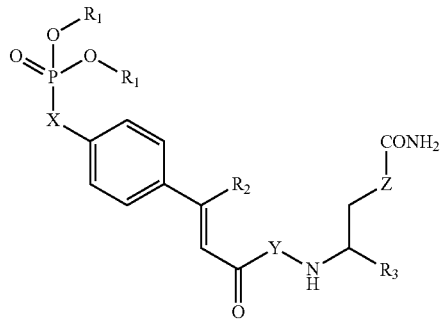

or a salt, ester or drug thereof, wherein:
X is selected from the group consisting of O, $CH_2$, $CF_2$, any of which may be optionally substituted;
Y is a dipeptide mimic selected from the group consisting of Haic (5-(amino)-1,2,4,5,6,7-hexahydro-4-oxo-(2S,5S)-azepino[3,2,1-hi]indole-2-carboxylic acid), or a dipeptide of the structure Aaa-Bbb in which Aaa is norleucine, leucine, or homophenylalanine and Bbb is proline, (2S,3R,4S)-cis-3,4-methanoproline, 4,4-difluoroproline, 4,4-dimethylproline, 4-hydroxyprolin, any of which may be optionally substituted;
Z is selected from the group consisting of $CH_2$, NH, or O, any of which may be optionally substituted;
$R_1$ is selected from the group consisting of a phenyl substituted group with one or more of the following: H, $CH_3$, F, CI, Br, $OCOCH_3$, $NO_2$, or CN; pivaloyloxymethyl; benzoyloxymethyl; benzoyloxymethyl in which the phenyl group is substituted with one or more of the following: H, $CH_3$, F, CI, Br, $OCOCH_3$, or $NO_2$; acetoxybenzyl; 2-pyridyl; 3-pyridyl; 4-pyridyl; or acyloxymethyl in which the acyl group possesses aliphatic or polyethylene glycol groups, $CH_2OCO(CH_2CH_2O)_n CH_2CH_3$ in which n≥1, $CH_2OCO(CH_2CH_2O)_n CH_3$ in which n≥1, any of which may be optionally substituted;
$R_2$ is selected from the group consisting of H or $CH_3$, any of which may be optionally substituted; and
$R_3$ is selected from the group consisting of H, $CH_3$, $CH(CH_3)_2$, $CH_2CH(CH_3)_2$, $CH_2CH_2CH_2CH_3$, $CH_2C_6C_4OH(para)$, $CH_2OCH_2C_6H_5$, $CH(CH_3)OCH_2C_6H_5$, $CH_2OH$, $CH_2OCOCH_3$, $CH(CH_3)OH$, $CH_2OCO(CH_2CH_2O)_n CH_3$ n=1-50, 1-piperidinomethyl, 4-morpholinomethyl, 1-methyl-4-piperazinomethyl, $CH_2NH_3$, $CH_2NHCOCH_3$, $CONHCH_2C_6H_5$, any of which may be optionally substituted,
and when $R_1$ is pivaloyloxymethyl, $R_2$ is not H and/or $R_3$ is not $CONHCH_2C_6H_5$.

2. A compound of structural Formula II

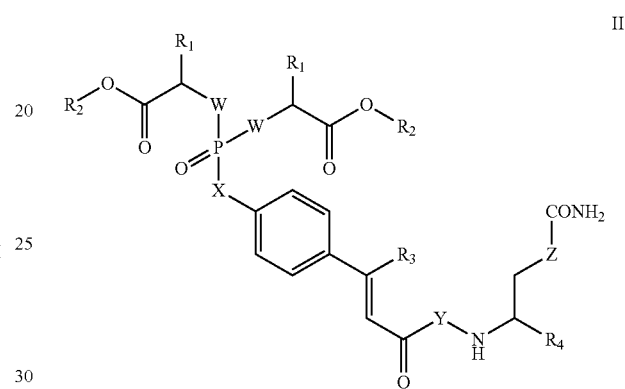

or a salt, ester or drug thereof, wherein:
X is selected from the group consisting of O, $CH_2$, or $CF_2$, any of which may be optionally substituted;
Y is selected from the group consisting of a dipeptide mimic such as Haic (5-(amino)-1,2,4,5,6,7-hexahydro-4-oxo-(2S,5S)-azepino[3,2,1-hi]indole-2-carboxylic acid), or a dipeptide of the structure Aaa-Bbb in which Aaa is norleucine, leucine, or homophenylalanine and Bbb is proline, (2S,3R,4S)-cis-3,4-methanoproline, 4,4-difluoroproline, 4,4-dimethylproline, 4-hydroxyproline, any of which may be optionally substituted;
Z is selected from the group consisting of $CH_2$, NH, or O, any of which may be optionally substituted;
W is selected from the group consisting of O, NH, or NH2, any of which may be optionally substituted;
$R_1$ is selected from the group consisting of H: $CH_3$, $CH_2C_6H_5$, $CH_2$-2-pyridyl, $CH_2$-3-pyridyl, $CH_2$-4-pyridyl, any of which may be optionally substituted;
$R_2$ is selected from the group consisting of $CH_3$, $CH_2CH_3$, $CH(CH_3)_2$, $C_6H_5$, $(CH_2CH_2O)_n CH_3$ in which n≥1, $CH_2OCO(CH_2CH_2O)_n CH_2CH_3$ in which N≥1, any of which may be optionally substituted;
$R_3$ is selected from the group consisting of H or $CH_3$, any of which may be optionally substituted; and
$R_4$ is selected from the group consisting of H, $CH_3$, $CH(CH_3)_2$, $CH_2CH(CH_3)_2$, $CH_2CH_2CH_2CH_3$, $CH_2C_6C_4OH(para)$, $CH_2OCH_2C_6H_5$, $CH(CH_3)OCH_2C_6H_5$, $CH_2OH$, $CH_2OCOCH_3$, $CH(CH_3)OH$, $CH_2OCO(CH_2CH_2O)_n CH_3$ n=1-50, $CH_2OCO(CH_2CH_2O)n CH_2CH_3$ n=1-50, 1-piperidinomethyl, 4-morpholinomethyl, 1-methyl-4-piperazinomethyl, $CH_2NH_3$, $CH_2NHCOCH_3$, $CONHCH_2C_6H_5$, any of which may be optionally substituted.

3. A compound of structural Formula III

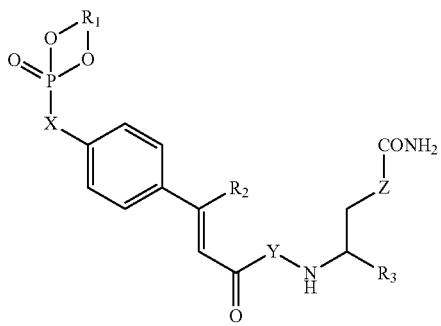

or a salt, ester or drug thereof, wherein:
X is selected from the group consisting of O, $CH_2$, and $CF_2$, any of which may be optionally substituted;
Y is a dipeptide mimic selected from the group consisting of Haic (5-(amino)-1,2,4,5,6,7-hexahydro-4-oxo-(2S,5S)-azepino[3,2,1-hi]indole-2-carboxylic acid), or a dipeptide of the structure Aaa-Bbb in which Aaa is nor-leucine, leucine, or homophenylalanine and Bbb is proline, (2S,3R,4S)-cis-3,4-methanoproline, 4,4-difluoroproline, 4,4-dimethylproline, 4-hydroxyproline, any of which may be optionally substituted;
Z is selected from the group consisting of $CH_2$, NH, or O, any of which may be optionally substituted;
$R_1$ is selected from the group consisting of bis methyleneoxy-1,2-phthaloyl, in which the phthaloyl can be substituted with one or more halogens, nitro groups, OH, $OCH_3$, $OCOR_4$ in which $R_4$ can be an aliphatic, aromatic, or heterocyclic group, $O(CH_2CH_2O)nOCH_3$ n=1-50, $O(CH_2CH_2O)$ $nOCH_2CH_3$ n=1-50, any of which may be optionally substituted;
$R_2$ is selected from the group consisting of H or $CH_3$, any of which may be optionally substituted; and
$R_3$ is selected from the group consisting of H, $CH_3$, $CH(CH_3)_2$, $CH_2CH(CH_3)_2$, $CH_2CH_2CH_2CH_3$, $CH_2C_6C_4OH(para)$, $CH_2OCH_2C_6H_5$, $CH(CH_3)OCH_2C_6H_5$, $CH_2OH$, $CH_2OCOCH_3$, $CH(CH_3)OH$, $CH_2OCO(CH_2CH_2O)_nCH_3$ n=1-50, 1-piperidinomethyl, 4-morpholinomethyl, 1-methyl-4-piperazinomethyl, $CH_2NH_3$, $CH_2NHCOCH_3$, $CONHCH_2C_6H_5$, any of which may be optionally substituted.

4. The compound of claim 1, wherein the compound is selected from the group consisting:
(2E)-3-[4-[[bis[(2,2-dimethyl-1-oxopropoxy)methoxyl] phosphinyl]difluoromethyl]phenyl]-but-2-enoyl-Haic-(R)-4-aminopentamide,
(2E)-3-[4-[[bis[(2,2-dimethyl-1-oxopropoxy)methoxyl] phosphinyl]difluoromethyl]phenyl]-but-2-enoyl-Haic-glutaminyl-benzylamide
(2E)-3-[4-[[bis[(2,2-dimethyl-1-oxopropoxy)methoxy] phosphinyl]difluoromethyl]phenyl]-but-2-enoyl-Haic -2-aminoethylcarbamate,
(2E)-3-[4-[[bis[(2,2-dimethyl-1-oxopropoxy)methoxyl] phosphinyl]difluoromethyl]phenyl]-but-2-enoyl-Haic -2- aminoethylurea,
(2E)-3-[4-[[bis[(2,2-dimethyl-1-oxopropoxy)methoxyl] phosphinyl]difluoromethyl]phenyll]-propenoyl-Haic-(R)-4-aminopentamide,
(2E)-3-[4-[[bis[(2,2-dimethyl-1- oxopropoxy)methoxyl] phosphinyl]oxy]phenyl]-but-2-enoyl -Haic-(R)-4-aminopentamide,
(2E)-3-[4-[(Diethoxyphosphinyl)difluoromethyl]phenyl]-but-2-enoyl-Haic-(R)-4-aminopentamide,
(E)-3-[4-[(Diphenoxyphosphinyl)difluoromethyl]phenyl]-but-2-enoyl-Haic-(R)-4-aminopentamide,
(2E)-3-[4-[[Bis[(4-fluorobenzoyloxy)methoxy]phosphinyl]difluoromethyl]phenyl]-but-2-enoyl-Haic-(R)-4-aminopentamide,
(2E)-3-[4-[[Bis[(benzoyloxy)methoxy]phosphinyl]difluoromethyl]phenyl]-but-2-enoyl-Haic-(R)-4-aminopentamide,
(2E)-3-4-[[phthaloylbis(oxymethoxy)]phosphinyl]difluoromethyl]phenyl]-but-2-enoyl-Haic-(R)-4-aminopentamide,
(2E)-3-[4-[[Bis[(piperonyloxy)methoxy]phosphinyl]difluoromethyl]phenyl]-but-2-enoyl-Haic-(R)-4-aminopentamide,
(E)-3-[4-[[Bis[(2-methylbenzoyloxy)methoxy]phosphinyl]difluoromethyl]phenyl]-but-2-enoyl-Haic-(R)-4-aminopentamide,
(2E)-3-[4-[[Bis[(2-chlorobenzoyloxy)methoxy]phosphinyl]difluoromethyl]phenyl]-but-2-enoyl-Haic-(R)-4-aminopentamide,
(2E)-3-[4-[[bis[(2,2-dimethyl-1-oxopropoxy)methoxy] phosphinyl]difluoromethyl]phenyl]-but-2-enoyl-norleucinyl-(2S,3R,4S)-methanoprolinyl-glutaminyl-benzylamide,
(2E)-3-[4-[[bis[(2,2-dimethyl-1-oxopropoxy)methoxy] phosphinyl]difluoromethyl]phenyl]-but-2-enoyl-norleucinyl-(2S,3R,4S)-methanoprolinyl-(4S,5R)-4-amino-5-benzyloxyhex amide,
(2E)-3-[4-[[bis[(2,2-dimethyl-1-oxopropoxy)methoxy] phosphinyl]difluoromethyl]phenyl]-but-2-enoyl-norleucinyl-(2S,3R,4S)-methanoprolinyl-(4S,5R)-4-amino-5-benzyloxyhex amide,
(2E)-3-[4-[[bis[(2,-dimethyl-1-oxopropoxy)methoxy] phosphinyl]difluoromethyl]phenyl]-but-2-enoyl-norleucinyl-(2S,3R,4S)-methanoprolinyl-(R)-4-aminopentamide,
(2E)-3-[4-[[bis [(2,2-dimethyl-1-oxopropoxy)methoxy] phosphinyl]difluoromethyl]phenyl]-but-2-enoyl-norleucinyl-(2R,3S,4R)-methanoprolinyl-(R)-4-aminopentamide,
(2E)-3-[4-[[bis[(2,2-dimethyl-1-oxopropoxy)methoxy] phosphinyl]difluoromethyl]phenyl]-but-2-enoyl-norleucinyl-(Rac)-methanoprolinyl-2-aminoethylurea,
(2E)-3-[4-[[bis[(2,2-dimethyl-1-oxopropoxy)methoxy] phosphinyl]difluoromethyl]phenyl]-but-2-enoyl-norleucinyl-(2S,3R,4S)-methanoprolinyl-2-aminoethylcarbamate,
(2E)-3-[4-[(Diphenoxyphosphinyl)difluoromethyl]phenyl]-but-2-enoyl-norleucinyl-(2S,3R,4S)-methanoprolinyl-(2S,3R,4S)-methanoprolinyl-(4S,5R)-4-amino-5-benzyloxyhexamide,
(2E)-3-[4-[[bis[(2,2-dimethyl-1-oxopropoxy)methoxy] phosphinyl]difluoromethyl]phenyl]-but-2-enoyl-norleucinyl-prolinyl-(R)-4-aminopentamide,
(2E)-3-[4-[[bis[(2,2-dimethyl-1-oxopropoxy)methoxy] phosphinyl]difluoromethyl]phenyl]-but-2-enoyl-norleucinyl-4,4-difluoroprolinyl-(R)-4-aminopentamide, and
(2E)-3-[4-[[bis[(2,2-dimethyl-1-oxopropoxy)methoxy] phosphinyl]difluoromethyl]phenyl]-but-2-enoyl-norleucinyl-4,4-dimethylprolinyl-(R)-4-aminopentamide.

5. A pharmaceutical composition comprising a compound as recited in claim 1 and pharmaceutically acceptable carrier.

6. A method of inhibition of STAT3 comprising contacting a cell with a compound as recited in claim 1.

7. A method for the treatment of breast cancer, comprising administering a therapeutically effective amount of a compound as recited in claim 1.

8. The compound of claim 1, wherein $R_2$ is $CH_3$.

9. The compound of claim 1, wherein X is $CF_2$.

10. The compound of claim 1, wherein $R_3$ is $CH_3$.

11. The compound of claim 1, wherein $R_3$ is $CH(CH_3)OCH_2C_6H_5$.

12. The compound of claim 1, wherein Z is $CH_2$.

13. The compound of claim 1, wherein Z is NH.

14. The compound of claim 1, wherein Y is Haic (5-(amino)-1,2,4,5,6,7-hexahydro-4-oxo-(2S,5S)-azepino[3,2,1-hi]indole-2-carboxylic acid).

15. The compound of claim 1, wherein Y is Aaa-Bbb wherein Aaa is norleucine and Bbb is proline, (2S,3R,4S)-cis-3,4-methanoproline, 4,4-difluoroproline, or 4,4-dimethylproline.

16. The compound of claim 1, wherein Bbb is (2S,3R,4S)-cis-3,4-methanoproline.

17. The compound of claim 1, wherein $R_1$ is pivaloyloxymethyl.

\* \* \* \* \*

UNITED STATES PATENT AND TRADEMARK OFFICE
CERTIFICATE OF CORRECTION

| | | |
|---|---|---|
| PATENT NO. | : 8,841,257 B2 | Page 1 of 1 |
| APPLICATION NO. | : 13/263815 | |
| DATED | : September 23, 2014 | |
| INVENTOR(S) | : John S. McMurray et al. | |

It is certified that error appears in the above-identified patent and that said Letters Patent is hereby corrected as shown below:

In the Claims

In claim 1, column 67, line 57, delete "CI" and insert --Cl-- therefor.
In claim 1, column 67, line 60, delete "CI" and insert --Cl-- therefor.
In claim 2, column 68, line 55, delete "N≥1" and insert --n≥1-- therefor.
In claim 4, column 69, line 50, delete "methoxyl" and insert --methoxy-- therefor.
In claim 4, column 69, line 53, delete "methoxyl" and insert --methoxy-- therefor.
In claim 4, column 69, line 59, delete "methoxyl" and insert --methoxy-- therefor.
In claim 4, column 69, line 62, delete "methoxyl" and insert --methoxy-- therefor.
In claim 4, column 69, line 63, delete "phenyll" and insert --phenyl-- therefor.
In claim 4, column 69, line 65, delete "methoxyl" and insert --methoxy-- therefor.
In claim 4, column 70, line 11, delete "(2E)-3-4-" and insert --(2E)-3-[4- -- therefor.
In claim 4, column 70, line 30, delete "benzyloxyhex amide" and insert --benzyloxyhexamide-- therefor.
In claim 4, column 70, line 33, delete "2S,3R,4S" and insert --2R,3S,4R-- therefor.
In claim 4, column 70, line 34, delete "benzyloxyhex amide" and insert --benzyloxyhexamide-- therefor.
In claim 4, column 70, line 35, delete "2,-dimethyl" and insert --2,2-dimethyl-- therefor.

Signed and Sealed this
Thirteenth Day of January, 2015

Michelle K. Lee
*Deputy Director of the United States Patent and Trademark Office*